United States Patent
Gohel et al.

(10) Patent No.: US 9,605,290 B2
(45) Date of Patent: *Mar. 28, 2017

(54) BIOCATALYTIC PROCESS FOR PREPARING ESLICARBAZEPINE AND ANALOGS THEREOF

(71) Applicant: Codexis, Inc., Redwood City, CA (US)

(72) Inventors: Anupam Gohel, Bekasi (ID); Derek J. Smith, Singapore (SG); Brian Wong, Singapore (SG); Joly Sukumaran, Singapore (SG); Wan Lin Yeo, Singapore (SG); Steven J. Collier, Concord, MA (US); Scott Novick, Palo Alto, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/150,686

(22) Filed: May 10, 2016

(65) Prior Publication Data

US 2016/0244792 A1    Aug. 25, 2016

Related U.S. Application Data

(60) Continuation of application No. 14/790,311, filed on Jul. 2, 2015, now Pat. No. 9,365,878, which is a division of application No. 14/110,964, filed as application No. PCT/US2012/033347 on Apr. 12, 2012, now Pat. No. 9,102,963.

(60) Provisional application No. 61/475,103, filed on Apr. 13, 2011.

(51) Int. Cl.
| | |
|---|---|
| C12N 9/04 | (2006.01) |
| C12N 9/02 | (2006.01) |
| C12N 15/63 | (2006.01) |
| C07H 21/04 | (2006.01) |
| C12P 17/10 | (2006.01) |
| C07D 223/22 | (2006.01) |
| C07D 223/28 | (2006.01) |
| C07D 453/02 | (2006.01) |
| C12P 41/00 | (2006.01) |

(52) U.S. Cl.
CPC ............ *C12P 17/10* (2013.01); *C07D 223/22* (2013.01); *C07D 223/28* (2013.01); *C07D 453/02* (2013.01); *C12N 9/0006* (2013.01); *C12P 41/002* (2013.01); *C12N 9/004* (2013.01); *C12Y 101/00* (2013.01); *Y02P 20/52* (2015.11)

(58) Field of Classification Search
CPC .... C12N 15/62; C12N 9/0004; C12Y 102/01; C12P 17/10
USPC .............................. 435/320.1, 189; 536/23.2
See application file for complete search history.

(56) References Cited

U.S. PATENT DOCUMENTS

| | | | |
|---|---|---|---|
| 3,324,113 | A | 6/1967 | Schindler et al. |
| 4,008,241 | A | 2/1977 | Gelbein et al. |
| 4,629,700 | A | 12/1986 | Prevatt et al. |
| 5,538,867 | A | 7/1996 | Durliat et al. |
| 5,753,646 | A | 5/1998 | Benes et al. |
| 5,808,058 | A | 9/1998 | Milanese |
| 6,071,901 | A | 6/2000 | Dorwald et al. |
| 6,117,679 | A | 9/2000 | Stemmer |
| 6,376,246 | B1 | 4/2002 | Crameri et al. |
| 6,495,023 | B1 | 12/2002 | Zeikus et al. |
| 6,537,746 | B2 | 3/2003 | Arnold et al. |
| 6,586,182 | B1 | 7/2003 | Patten et al. |
| 7,119,197 | B2 | 10/2006 | Learmonth |
| 7,705,036 | B2 | 4/2010 | Chou et al. |
| 2005/0095619 | A1 | 5/2005 | Davis et al. |
| 2005/0153417 | A1 | 7/2005 | Davis et al. |
| 2006/0195947 | A1 | 8/2006 | Davis et al. |
| 2008/0220990 | A1 | 9/2008 | Fox |
| 2008/0318295 | A1 | 12/2008 | Ching et al. |
| 2009/0093031 | A1 | 4/2009 | Liang et al. |
| 2009/0155863 | A1 | 6/2009 | Liang et al. |
| 2009/0162909 | A1 | 6/2009 | Campopiano et al. |
| 2009/0191605 | A1 | 7/2009 | Liang et al. |
| 2009/0312196 | A1 | 12/2009 | Colbeck et al. |
| 2010/0055751 | A1 | 3/2010 | Voladri et al. |
| 2010/0062499 | A1 | 3/2010 | Mundorff et al. |

FOREIGN PATENT DOCUMENTS

| | | |
|---|---|---|
| WO | 95/22625 A1 | 8/1995 |
| WO | 97/00078 A1 | 1/1997 |
| WO | 97/35966 A1 | 10/1997 |
| WO | 98/27230 A1 | 6/1998 |
| WO | 00/42651 A1 | 7/2000 |
| WO | 00/53731 A2 | 9/2000 |
| WO | 01/75767 A2 | 10/2001 |
| WO | 02/092572 A1 | 11/2002 |
| WO | 2005/018579 A2 | 3/2005 |
| WO | 2007012793 A1 | 2/2007 |
| WO | 2007/117166 A1 | 10/2007 |
| WO | 2008/151324 A1 | 12/2008 |
| WO | 2009/008908 A2 | 1/2009 |
| WO | 2010/025238 A2 | 3/2010 |

(Continued)

OTHER PUBLICATIONS

Altschul, S., et al., "Basic local alignment search tool," J. Mol. Biol., 215: 403-410 (1990).

(Continued)

*Primary Examiner* — Robert Mondesi
*Assistant Examiner* — Younus Meah
(74) *Attorney, Agent, or Firm* — Codexis, Inc.

(57) ABSTRACT

The present disclosure relates to biocatalysts and its uses for the efficient preparation of eslicarbazepine, eslicarbazepine acetate, and analogs thereof.

20 Claims, No Drawings

(56) References Cited

FOREIGN PATENT DOCUMENTS

| WO | 2010/025287 A2 | 3/2010 |
|---|---|---|
| WO | 2010/113179 A2 | 10/2010 |

OTHER PUBLICATIONS

Altschul, S.F., et al., "Gapped BLAST and PSI-BLAST: a new generation of protein database search programs," Nucleic Acids Res., 25(17):3389-3402 (1997).

Beaucage, S.L., et al., "Deoxynucleoside phosphoamidites—A new class of key intermediates for deoxypolynucleotide synthesis," Tetrahedron Letters, 22(20):1859-62 (1981).

Black, M.E., et al., "Creation of drug-specific herpes simplex virus type 1 thymidine kinase mutants for gene therapy," Proc Natl Acad Sci USA, 93:3525-3529 (1996).

Botstein, D., et al., "Strategies and applications of in vitro mutagenesis," Science, 229(4719):1193-1201 (1985).

Caldwell, R.C., et al., "Mutagenic PCR," PCR Methods Appl., 3:S136-S140 (1994).

Carter, P., "Site-directed mutagenesis," Biochem. J., 237:1-7 (1986).

Chen, A.G., et al., "Simultaneous determination of imipramine, desipramine and their 2- and 10-hydroxylated metabolites in human plasma and urine by high-performance liquid chromatography," J Chromatogr B, 693(1):153-8 (1997).

Christians, F.C., et al., "Directed evolution of thymidine kinase for AZT phosphorylation using DNA family shuffling," Nat. Biotechnol., 17:259-264 (1999).

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling,"Nat. Biotechnol., 14(3):315-319 (1996).

Crameri, A., et al., "Molecular evolution of an arsenate detoxification pathway by DNA shuffling," Nat. Biotechnol., 15(5):436-438 (1997).

Dale, S.J., et al., "Oligonucleotide-directed random mutagenesis using the phosphorothioate method," Methods Mol. Biol., 57:369-74 (1996).

Eisenberg, D., et al., "Analysis of Membrane and Surface Protein Sequences with the Hydrophobic Moment Plot," J. Mol. Biol., 179:125-142 (1984).

Henikoff, S.,et al., "Amino acid substitution matrices from protein blocks," Proc. Natl. Acad. Sci., 89:10915-10919 (1992).

Koszelewski, D., et al., "Immobilization of omega-transaminases by encapsulation in a sol-gel/celite matrix," Journal of Molecular Catalysis B: Enzymatic, 63: 39-44 (2010).

Kramer, B., et al., "Different base/base mismatches are corrected with different efficiencies by the methyl-directed DNA mismatch-repair system of E. coli," Cell, 38(3):879-887 (1984).

Ling, M., et al., "Approaches to DNA Mutagenesis:An Overview," Anal. Biochem., 254:157-78 (1997).

Martin, A.R., et al., "Characterization of free and immobilized (S)-aminotransferase for acetophenone production," Applied Microbiology and Biotechnology, 76(4): 843-851 (2007).

Mateo, C., et al., "Epoxy sepabeads: a novel epoxy support for stabilization of industrial enzymes via very intense multipoint covalent attachment," Biotechnology Progress 18(3):629-34 (2002).

Matthes, H.W.D., et al., "Simultaneous rapid chemical synthesis of over one hundred oligonucleotides on a microscale," EMBO J., 3(4):801-05 (1984).

Minshull, J., et al., "Protein evolution by molecular breeding," Curr. Op. Chem. Biol., 3(3):284-290 (1999).

Needleman, S., et al., "A general method applicable to the search for similarities in the amino acid sequence of two proteins," J. Mol. Biol. 48:443-453 (1970).

Nielsen, K.K., et al.,"High-performance liquid chromatography of imipramine and six metabolites in human plasma and urine," J. Chromatogr., 612(1):87-95 (1993).

Pearson, W.R., "Improved tools for biological sequence comparison," Proc. Nat'l. Acad. Sci. USA, 85:2444-2448 (1988).

Puigbo, P., et al., "Optimizer: a web server for optimizing the codon usage of DNA sequences," Nucleic Acids Res., 35 (Web Server issue): W126-31 (2007).

Rauchenzauner, M., et al., "Update on treatment of partial onset epilepsy: role of eslicarbazepine," Neuropsychiatr Dis Treat., 6: 723-730 (2010).

Smith, M., "In Vitro mutagenesis," Ann. Rev. Genet., 19:423-462 (1985).

Smith, T., et al., "Comparison of Biosequences," Adv. Appl. Math, 2:482-489 (1981).

Stemmer, W., "DNA Shuffling by Random Fragmentation and Reassembly: In Vitro Recombination for Molecular Evolution," Proc. Natl. Acad. Sci. USA, 91:10747-10751 (1994).

Stemmer, W.P.C., "Rapid evolution of a protein in vitro by DNA shuffling", Nature, 370:389-391 (1994).

Truppo, M.D., et al., "Development of an Improved Immobilized CAL-B for the Enzymatic Resolution of a Key Intermediate to Odanacatib," Organic Process Research & Development, 15:1033-1035 (2011).

Wells, J.A., et al., "Cassette mutagenesis: an efficient method for generation of multiple mutations at defined sites," Gene, 34:315-323 (1985).

Yi, S., et al., "Covalent immobilization of omega-transaminase from *Vibrio fluvialis* JS17 on chitosan beads," Process Biochemistry 42(5): 895-898 (2007).

Zhang, J-H., et al., "Directed evolution of a fucosidase from a galactosidase by DNA shuffling and screening ,"Proc. Nat. Acad. Sci., U.S.A., 94:4504-4509 (1997).

Zhao, H., et al., "Molecular evolution by staggered extension process (StEP) in vitro recombination," Nat. Biotechnol., 16:258-261 (1998).

Genbank Accession No. AAP94029.1; GI: 33112056—dated Apr. 1, 2004; downloaded May 19, 2010.

Disclosed Anonymously, "Process for the preparation of (10S)-10-hydroxy-10,11-dihydro-5H-dibenzo[b,f]azepine-5-carboxamine," IP.com, pp. 1-3 [2010].

BIOCATALYTIC PROCESS FOR PREPARING ESLICARBAZEPINE AND ANALOGS THEREOF

1. CROSS-RELATED APPLICATIONS

The present application is a Continuation of U.S. patent application Ser. No. 14/790,311, filed Jul. 2, 2015, now U.S. Pat. No. 9,365,878 which is a Divisional of U.S. patent application Ser. No. 14/110,964, filed Dec. 5, 2013, now U.S. Pat. No. 9,102,963 which is a national stage application filed under 35 USC §371 and claims priority of the international application PCT/JS2012/033347, filed Apr. 12, 2012, and U.S. provisional patent applications 61/475,103, filed Apr. 13, 2011, each of which is hereby incorporated by reference herein.

2. TECHNICAL FIELD

The present disclosure relates to biocatalyst-mediated processes for producing chiral compounds and biocatalysts used in the processes.

3. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "CX2-085WO1_ST25.txt", a creation date of Apr. 12, 2012, and a size of 65,605 bytes. The Sequence Listing filed via EFS-Web is part of the specification and is hereby incorporated in its entirety by reference herein.

4. BACKGROUND

Oxcarbazepine (10-oxo-10,11-dihydro-5H-dibenzo[b,f]azepine-5-carboxamide) is a 10-keto analogue of carbamazepine (dibenzo[V]azepine-5-carboxamide). The structurally similar compounds

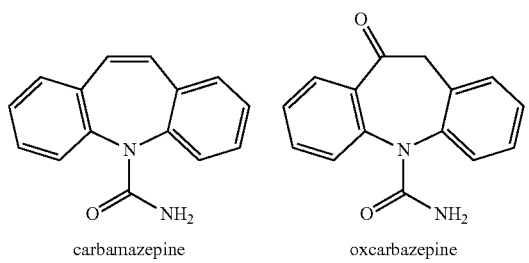

carbamazepine        oxcarbazepine are known to block voltage-gated sodium channel activity and indicated for use in the treatment of epilepsy. Oxcarbazepine was designed to avoid the oxidative metabolic transformation of carbamazepine. Oxcarbazepine itself undergoes rapid conversion in vivo to a mixture of (S)-10-hydroxy-10,11-dihydro-5H-dibenzo[b,f]axepine-5-carboxamide (S-licarbazepine or eslicarbazepine) and (R)-10-hydroxy-10,11-dihydro-5H-dibenzo[b,f]azepine-5-carboxamide (R-licarbazepine)

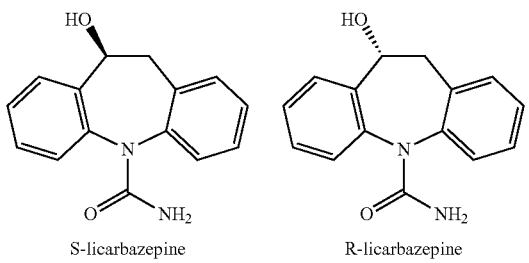

S-licarbazepine          R-licarbazepine

Based on the active metabolites of oxcarbazepine, eslicarbazepine acetate, chemically known as (S)-5-carbamoyl-10,11-dihydro-5H-dibenzo[b,f]azepin-10-yl acetate (structure shown below),

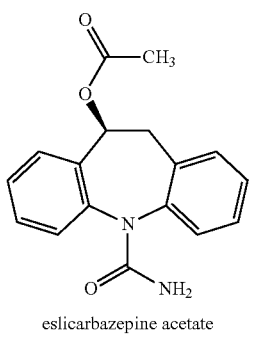 [SMILES: CC(=O)O[C@H]1Cc2ccccc2N(C(N)=O)c2ccccc21]

eslicarbazepine acetate was developed on the view that the S-isomer would be a more physiologically effective, have fewer adverse effects, and cross the blood brain barrier more efficiently than R-licarbazepine. Eslicarbazepine acetate prodrug is efficiently absorbed in the gastrointestinal tract and is metabolized to eslicarbazepine by hydrolysis of the acetate group (Rauchenzauner, M. and Luef, G., 2010, Neuropsychiatr Dis Treat. 6: 723-730).

Chemical preparation of eslicarbazepine acetate is described in US2007119197, WO02092572, WO2007117166, WO2007012793, and WO2010113179. One process involves preparing a racemic mixture, resolving the (S) and (R) enantiomers of licarbazepine from the racemic mixture and using the intermediates to form the S- and R-licarbazepine acetate. Another process involves reduction of oxcarbazepine in the presence of a catalyst and a hydride source to form S-licarbazepine in enantiomeric excess. Eslicarbazepine acetate can also be prepared directly by asymmetric hydrogenation of the enol acetate of oxcarbazepine. See, e.g., WO2007117166.

Publication IPCOM000193904D describes carbonyl reductase (ketoreductase) mediated conversion of oxcarbazepine to S- or R-licarbazepine. The ketoreductases produced either R- or S-licarbazepine in enantiomeric excess, thus indicating differences in stereoselectivity, depending on the type of carbonyl reductase used. The reaction conditions, which included a temperature of 30° C. and time of 18-24 h or a temperature of 40° C. and a time of 18 to 24 h resulted in conversion of only about 6% to about 21% to product (defined as EsCBZ purity).

It is desirable to have efficient and cost-effective processes for synthesis of eslicarbazepine and eslicarbazepine acetate, for example processes that result in conversion of >90% of starting compound to eslicarbazepine in >98% enantiomeric excess. Particularly desirable are efficient processes capable of high percent production of eslicarbazepine with high loading of starting compound (e.g., ≥100 g/L of oxcarbazepine).

5. SUMMARY

The present disclosure provides processes for the biocatalytic conversion of oxcarbazepine (compound (2c), 10-oxo-10,11-dihydro-5H-dibenzo[b,f]azepine-5-carboxamide and structural analogs thereof to chiral alcohol eslicarbazepine (compound (1c), 5S-5-hydroxy-5,6-dihydrobenzo[b][1]benzazepine-11-carboxamide) or corresponding chiral alcohol analogs in enantiomeric excess, as illustrated in Scheme 1, Scheme 1

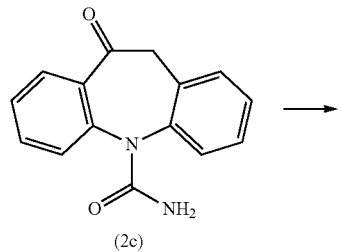

(2c)

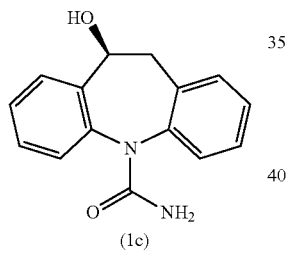

(1c)

polypeptides that mediate the conversion, polynucleotides encoding the polypeptides, and methods of making the polypeptides for use in the processes.

The biocatalysts are ketoreductases derived from *Lactobacillus*, particularly non-naturally occurring ketoreductases engineered for mediating the conversion with increased activity, high enantiomeric excess, high percent conversion in the presence of high substrate loading, and capable of regenerating the cofactor by its in situ activity as an alcohol dehydrogenase.

Accordingly, in some embodiments, the process for preparing compound (1c) in enantiomeric excess comprises contacting compound (2c) with a ketoreductase described herein, particularly a non-naturally occurring or engineered polypeptides of the present disclosure in the presence of NADPH or NADH cofactor under suitable reaction conditions.

In another aspect, a structural analog of compound (1c) can be prepared in enantiomeric excess using the ketoreductases described herein. In some embodiments, the structural analog are encompassed by structural formula (1)

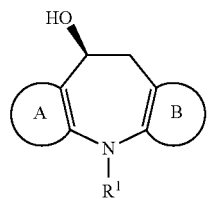

wherein
each ring A and B is independently an optionally substituted monocyclic aryl or heteroaryl,
$R^1$ is selected from hydrogen, hydroxy, halo, cyano, carboxy, and an optionally substituted alkyl, aminoalkyl, cycloalkyl, heterocycloalkyl, alkyloxycarbonyl, aminocarbonyl, aminothiocarbonyl, aminosulfonyl, and sulfonyl. In some embodiments, $R^1$ is selected from H, —OH, —CN, —C(O)OR$^a$, —(C1-C4)alkyl-NR$^b$R$^c$, —C(O)NR$^b$R$^c$, —C(S)NR$^b$R$^c$, —SO$_2$NR$^b$R$^c$, —SO$_2$R$^b$, bicycloalkyl and heterobicycloalkyl, wherein R$^a$, R$^b$ and R$^c$ are each independently selected from H and an optionally substituted alkyl, alkenyl, alkynyl, cycloalkyl, heterocycloalkyl, aryl, and heteroaryl. In some embodiments, $R^1$ is —C(O)NH$_2$, dimethylaminopropyl, methylaminopropyl, and quinuclidinyl. Other chiral alcohol compounds of structural formula (1) that can be prepared are further described in the detailed description.

In some embodiments, the method for preparing a compound of structural formula (1) comprises contacting a compound of structural formula (2)

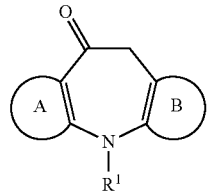

wherein rings A and B, and $R^1$ are defined above, with any of the ketoreductases of the present disclosure, in presence of NADH or NADPH under suitable reaction conditions.

Suitable reactions conditions for the conversion of compound (2c) to compound (1c) and compounds of structural formula (2) to compounds of structural formula (1) in enantiomeric excess employing ketoreductases are provided in greater detail in the description below, including but not limited to ranges of pH, temperature, buffer, solvent system, substrate loading, polypeptide loading, cofactor loading, and reaction time.

In some embodiments, the improvements in enzyme properties of the non-natural, engineered ketoreductases allow the process to be carried out in, by way of example, a pH range of about 6 to about 12, a temperature of about 20° C. to about 60° C., and a NADPH or NADH cofactor concentration of about 0.03 g/L to about 1 g/L. The engineered polypeptides with improved enzyme properties can be used at lower concentrations to reduce the amount of protein residue that must be removed in subsequent workup of the product, and can vary, by way of example and not limitation, from 0.1 g/L to about 10 g/L, about 0.1 g/L to about 5 g/L, about 0.1 g/L to about 2 g/L, or about 0.1 g/L to about 1.0 g/L. The substrate loading, particularly with reference to compound (2c) can be from, by way of example, from about 1 g/L to 100 g/L or greater. In some embodiments, the process can be carried out, wherein the engineered ketoreductase is immobilized on a solid support.

In some embodiments, the process for preparing compound (1c) or compounds of structural formula (1) can further comprise a cofactor regeneration system capable of converting NADP+ to NADPH, or NAD+ to NADH. A cofactor recycling system can enhance the efficiency of conversion while lowering the amount of cofactor required in the reaction. The cofactor recycling system comprises a dehydrogenase and a corresponding substrate, for example, glucose dehydrogenase and glucose, glucose phosphate dehydrogenase and glucose-6-phosphate, formate dehydrogenase and formate, and a ketoreductase/alcohol dehydrogenase and a secondary alcohol, e.g., isopropanol (IPA). In some embodiments, the ketoreductases capable of converting compound (2c) to compound (1c) is also capable of acting as a cofactor recycling system by converting a secondary alcohol, for example isopropanol, to its corresponding ketone. Accordingly, a secondary alcohol, particularly isopropanol, can be used in a co-solvent system in the process with the engineered ketoreductases of the disclosure to convert compound (2c) or compounds of structural formula (2) to compound (2c) or compounds of structural formula (1), respectively, and also regenerate the cofactor, particularly NADPH, using IPA as the substrate.

In some embodiments, the processes can be used to convert at least about 91%, 92%, 93%, 94%, 95%, 96%, 97%, 98%, 99% or greater of compound (2c) to compound (1c) in 24 h or less.

In some embodiments, the process can be used to convert compound (2c) to compound (1c) enantiomeric excess of at least about 91%, 92%, 93%, 94%, 95%, 96%, 97%, 98%, 99% or greater of compound (1c) in 24 h or less.

In the embodiments herein, the ketoreductases for use in the process are derived from *Lactobacillus*, particularly *Lactobacillus kefir*. In some embodiments, the ketoreductases are non-natural, engineered ketoreductases that have residue differences as compared to the naturally occurring ketoreductase of *L. kefir* represented by SEQ ID NO:2. These differences occur at residue positions that can affect enzyme activity, stereoselectivity, thermostability, solvent stability, polypeptide expression, co-factor affinity, or various combinations thereof. In particular, the engineered polypeptides can have one or more residue difference as compared to SEQ ID NO:2 at the following residue positions: X17, X25, X29, X40, X43, X64, X71, X76, X80, X87, X94, X95, X96, X131, X144, X145, X147, X150, X152, X153, X157, X173, X190, X194, X195, X196, X199, X200, X226, X233, and X249. Guidance on amino acid residues that can be present at these positions as well as combinations of residue differences useful for generating enzymes with improved properties are described in detail in the descriptions herein.

In some embodiments, the engineered ketoreductase polypeptides capable of converting compound (2c) or a structural analog thereof to compound (1c) or corresponding structural analog in enantiomeric excess, comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide selected from SEQ ID NO:6, 8, 10, 12, 14, 16, 18, 20, 22, 24, 26, 28, 30, 32, 34, 36, and 38.

in some embodiments, the non-naturally occurring ketoreductase polypeptide for use in the processes disclosed herein and capable of converting compound (2c) or structural analog thereof to compound (1c) or corresponding structural analog in enantiomeric excess with activity that is equal to or with at least 2-fold, at least 10-fold, at least 15-fold, at least 20-fold, at least 25-fold, at least 30-fold, or at least 35-fold or more activity of the polypeptide of SEQ ID NO:4 comprises an amino acid sequence that has at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, or 38, with the proviso that the amino acid sequence comprises any one of the set of residue differences as compared to SEQ ID NO: 2 contained in any one of the polypeptide sequences of SEQ ID NO:4 to SEQ ID NO:38 listed in Table 3. In some embodiments, in addition to the set of amino acid residue differences of any one of the non-naturally occurring polypeptides of SEQ ID NO: 4 to SEQ ID NO: 38, the sequence of the non-naturally occurring polypeptide can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the SEQ ID NO: 2. In some embodiments, the residue differences can comprise conservative substitutions and non-conservative substitutions as compared to SEQ ID NO: 2.

In some embodiments, the ketoreductase capable of converting compound (2c) or structural analog thereof to compound (1c) or corresponding structural analog in enantiomeric excess and having the specified sequence identity to any of the reference polypeptides described herein, has an amino acid sequence that comprises at least the following features: X80 is T; X96 is V or R; X145 is L; X153 is T; X190 is P; X196 is L or M; and X226 is V.

In some embodiments, the ketoreductase amino acid sequence with the specified features at residue positions X80, X96, X145, X153, X190, X196, and X226, further comprises one or more of the following features: X71 is P or G; X87 is L; and X131 is C.

In some embodiments, the ketoreductase amino acid sequence with the specified features at residue positions X80, X96, X145, X153, X190, X196, and X226, and X71, X87, and X131 above can further comprise one or more of the following features: X17 is H or M; X29 is T; X40 is R; X43 is R or V; X64 is V; X94 is G; X95 is Y or M; X147 is Q or M; X152 is L or A; X173 is L; X199 is M; and X200 is P.

In some embodiments, the ketoreductase amino acid sequence with the specified features at the residue positions indicated above can further comprise one or more of the following features: X25 is T; X76 is A; X144 is V; X150 is L; X157 is C or S; X194 is R; X233 is G; and X249 is W or F.

In some embodiments, the ketoreductase capable of converting compound (2c) or structural analog to compound (1c) or corresponding structural analog in enantiomeric excess and having the specified sequence identity to any of the reference polypeptides, has an amino acid sequence that comprises at least the following features: X64 is V; X71 is P; X80 is T; X87 is L; X94 is A or G; X96 is V; X145 is L; X147 is Q or M; X153 is T; X173 is L; X190 is P; X196 is M; X199 is M; and X226 is V.

In some embodiments, the ketoreductase amino acid sequence with the specified features at residue positions X64, X71, X80, X87, X94, X96, X145, X147, X153, X173, X190, X196, X199 and X226, further comprises one or more of the following features: X17 is M or H; X29 is T; X40 is R; X43 is R or V; X95 is M or Y; X131 is C; X152 is L or A; and X200 is P.

In some embodiments, the ketoreductase amino acid sequence with the specified features at the residue positions indicated above can further comprise one or more of the following features: X25 is T; X76 is A; X144 is V; X150 is L; X157 is C or S; X194 is R; X233 is G; and X249 is W or F.

In some embodiments, the ketoreductase capable of converting compound (2c) or structural analog to compound (1c) or corresponding structural analog in enantiomeric excess and having the specified sequence identity to any of the reference polypeptides, has an amino acid sequence that comprises at least the following features: X17 is H or M; X25 is T; X29 is T; X40 is R; X43 is R or V; X64 is V; X71 is G or P; X80 is T; X87 is L; X94 is G; X95 is Y or M; X96 is R or V; X131 is C; X145 is L; X147 is Q or M; X152 is A or L; X153 is T; X157 is S or C; X173 is L; X190 is P; X196 is M or L; X199 is M; X200 is P; and X226 is V.

In some embodiments, the ketoreductase with the preceding specified features can further comprise one or more of the following features: X76 is A; X144 is V; X150 is L; X194 is R; X233 is G; and X249 is W or F.

In some embodiments, the non-naturally occurring ketoreductase polypeptides capable of converting compound (2c) or structural analog thereof to compound (1c) or corresponding structural analog, comprises an amino acid sequence selected from SEQ ID NO: 6, 8, 10, 12, 14, 16, 18, 20, 22, 24, 26, 28, 30, 32, 34, 36, and 38.

In another aspect, an engineered ketoreductase polypeptide comprises an amino acid sequence that has at least 80%, 80%, 85%, 86%, 87%, 88%, 89%, 90%, 91%, 92%, 93%, 94%, 95%, 96%, 97%, 98%, or 99% sequence identity to the reference polypeptide of SEQ ID NO:2 and comprises at least one or more residue differences as compared to SEQ ID NO:2 at residue positions X71, X87 and X131, wherein the polypeptide has ketoreductase activity.

In another aspect, the present disclosure provides polynucleotides encoding the ketoreductase polypeptide capable of converting compound (2c) to compound (1c) in enantiomeric excess, expression vectors comprising the polynucleotides, and host cells capable of expressing the polynucleotides encoding the engineered polypeptides.

In a further aspect, the present disclosure also provides method of manufacturing the engineered ketoreductase polypeptides, where the method comprises culturing a host cell capable of expressing the engineered ketoreductase polypeptide under culture conditions suitable for expression of the polypeptide. The method can further comprise isolating the expressed polypeptide.

6. DETAILED DESCRIPTION

The synthesis of eslicarbazepine, also known S-licarbazepine and having the chemical name (S)-10-hydroxy-10,11-dihydro-5h-dibenzo[b,f]azepine-5-carboxamide, has been carried out using chemical procedures, such as by chiral separation of S-licarbazepine from R-licarbazepine or by chiral synthesis of S-licarbazepine. See, e.g., US2007119197, WO02092572, WO2007117166, WO2007012793, and WO2010113179. As noted above, chemical synthesis can be circumvented by employing carbonyl reductases (e.g., ketoreductases) to enzymatically reduce oxcarbazepine to the corresponding chiral alcohol. However, some ketoreductases produce R-licarbazepine in enantiomeric excess while other ketoreductases produce S-licarbazepine in enantiomeric excess (see Publication IPCOM000193904D). The reference IPCOM000193904D did not describe the features that distinguish a ketoreductase with stereoselectivity for S-licarbazepine from ketoreductases with stereoselectivity for R-licarbazepine. It is now shown herein that ketoreductases derived from a ketoreductase of *Lactobacillus* are capable of converting oxcarbazepine to eslicarbazepine in enantiomeric excess. Based on this finding, other engineered ketoreductases have been developed that are capable of efficiently converting oxcarbazepine to eslicarbazepine in ≥90% enantiomeric excess, including engineered ketoreductases capable of >90% conversion of oxcarbazepine at a substrate loading of about 50 to about 100 g/L to eslicarbazepine in ≥99% enantiomeric excess within 24 h.

For the descriptions herein and the appended claims, the singular forms "a", "an" and "the" include plural referents unless the context clearly indicates otherwise. Thus, for example, reference to "a polypeptide" includes more than one polypeptide, and reference to "a compound" refers to more than one compound.

It is to be further understood that where descriptions of various embodiments use the term "comprising," those skilled in the art would understand that in some specific instances, an embodiment can be alternatively described using language "consisting essentially of" or "consisting of."

Also, the use of "or" means "and/or" unless stated otherwise. Similarly, "comprise," "comprises," "comprising" "include," "includes," "including," "has," "have," and "having" are interchangeable and not intended to be limiting.

The foregoing general description and the detailed description are exemplary and explanatory only and are not restrictive of this disclosure.

6.1 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Protein," "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Non-naturally occurring" or "engineered" or "recombinant" when used in the present disclosure with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Reference sequence" refers to a defined sequence to which another sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity. The term "reference sequence" is not intended to be limited to wild-type sequences, and can include engineered or altered sequences. For example, in some embodiments, a "reference sequence" can be a previously engineered or altered amino acid sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned. As used herein, a reference to a residue position, such as "Xn' as further described below, is to be construed as referring to "a residue corresponding to", unless specifically denoted otherwise.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate, e.g., compound (2c), to its corresponding chiral alcohol product, e.g., compound (1c), with at least about 85% stereomeric excess.

"Increased enzymatic activity" or "increased activity" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of ketoreductase) as compared to a reference enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. The ketoreductase activity can be measured by any one of standard assays used for measuring ketoreductases, such as change in substrate or product concentration, or change in concentration of the cofactor (in absence of a cofactor regenerating system). Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a ketoreductase polypeptide can be expressed as "percent conversion" of the substrate to the product.

"Thermostable" or "thermal stable" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (e.g., more than 60% to 80% for example) after exposure to elevated temperatures.

"Solvent stable" refers to the ability of a polypeptide to maintain similar activity (e.g., more than e.g., 60% to 80%) after exposure to varying concentrations (e.g. 5-99%) of solvent (e.g., isopropylalcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include Glu (E) and Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include Arg (R) and Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include Pro (P), Ile (I), Phe (F), Val (V), Leu (L), Trp (W), Met (M), Ala (A) and Tyr (Y).

"Aromatic Amino Acid or Residue" refers to a hydrophilic or hydrophobic amino acid or residue having a side chain that includes at least one aromatic or heteroaromatic ring. Genetically encoded aromatic amino acids include Phe (F), Tyr (Y) and Trp (W). Although owing to the its heteroaromatic ring side chain His (H) is classified as an aromatic residue, it may also be classified as a basic residue owing to pKa of its heteroaromatic nitrogen atom.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include Gly (G), Leu (L), Val (V), Ile (I), Met (M) and Ala (A).

"Aliphatic Amino Acid or Residue" refers to a hydrophobic amino acid or residue having an aliphatic hydrocarbon side chain. Genetically encoded aliphatic amino acids include Ala (A), Val (V), Leu (L) and Ile (I).

The amino acid Cys (C) is unique in that it can form disulfide bridges with other Cys (C) amino acids or other sulfanyl- or sulfhydryl-containing amino acids. The ability of Cys (and other amino acids with —SH containing side chains) to exist in a polypeptide in either the reduced free —SH or oxidized disulfide-bridged form affects whether it contributes net hydrophobic or hydrophilic character to the polypeptide. While Cys exhibits a hydrophobicity of 0.29 according to the normalized consensus scale of Eisenberg (Eisenberg et al., 1984, supra), it is to be understood that for purposes of the present disclosure, Cys is classified into its own unique group.

The amino acid Pro (P) has a conformationally constrained nature. Although it has hydrophobic properties, as used herein, Pro (P) or other similar residues is classified as a "conformationally constrained."

"Hydroxyl-containing Amino Acid or Residue" refers to an amino acid or residue containing a hydroxyl (—OH) moiety. Genetically-encoded hydroxyl-containing amino acids include Ser (S) and Thr (T). While L-Tyr (Y) contains a hydroxyl moiety, it is classified herein as an aromatic amino acid or residue.

"Amino acid difference" or "residue difference" refers to a change in the residue at a specified position of a polypeptide sequence when compared to a reference sequence. For example, a residue difference at position X80, where the reference sequence has an alanine, refers to a change of the residue at position X80 to any residue other than alanine. As disclosed herein, an enzyme can include one or more residue differences relative to a reference sequence, where multiple residue differences typically are indicated by a list of the specified positions where changes are made relative to the reference sequence. The residue differences can be non-conservative changes or conservative changes. In some embodiments, the residue differences can be conservative substitutions, non-conservative substitutions, or a combination of non-conservative and conservative substitutions. For the descriptions of the non-naturally occurring polypeptides herein, the amino acid residue position in the reference sequence is determined in the ketoreductase polypeptide beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The polypeptide sequence position at which a particular amino acid or amino acid change ("residue difference") is present is sometimes described herein as "Xn", or "position n", where n refers to the residue position with respect to the reference sequence. Where applicable, a specific substitution mutation, which is a replacement of the specific residue in a reference sequence with a different specified residue may be denoted by the conventional notation "X(number)Y", where X is the single letter identifier of the residue in the reference sequence, "number" is the residue position in the reference sequence, and Y is the single letter identifier of the residue substitution in the engineered sequence.

"Conservative amino acid substitutions" refer to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1.

TABLE 1

| Residue | Possible Conservative Substitutions |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |

TABLE 1-continued

| Residue | Possible Conservative Substitutions |
| --- | --- |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the polypeptide while retaining enzymatic activity and/or retaining the improved properties of an engineered enzyme. Deletions can be directed to the internal portions and/or terminal portions of the polypeptide. In various embodiments, the deletion can comprise a continuous segment or can be discontinuous.

"Insertion" refers to modification of the polypeptide by addition of one or more amino acids to the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can typically have about 80%, 90%, 95%, 98%, and 99% of the full-length ketoreductase polypeptide, for example the polypeptide of SEQ ID NO:4.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the engineered ketoreductase polypeptides of the present disclosure can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure engineered ketoreductase polypeptide composition will comprise about 60% or more, about 70% or more, about 80% or more, about 90% or more, about 95% or more, and about 98% or more of all macromolecular species by mole or % weight present in the composition. Solvent species, small molecules (<500 Daltons), and elemental ion species are not considered macromolecular species. In some embodiments, the isolated improved ketoreductase polypeptide is a substantially pure polypeptide composition.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. In some embodiments, the polynucleotides encoding the ketoreductase enzymes may be codon optimized for optimal production from the host organism selected for expression.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Cofactor regeneration system" or "cofactor recycling system" refers to a set of reactants that participate in a reaction that reduces the oxidized form of the cofactor (e.g., NADP+ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from NAD+ or NADP+, respectively, are known in the art and may be used in the methods described herein.

"Glucose dehydrogenase" and "GDH" are used interchangeably herein to refer to an NAD+ or NADP+-dependent enzyme that catalyzes the conversion of D-glucose and NAD+ or NADP+ to gluconic acid and NADH or NADPH, respectively.

"Secondary alcohol dehydrogenase" is used herein to refer to an NAD+ or NADP+-dependent enzyme that catalyzes the conversion of a secondary alcohol (e.g., isopropanol) and NAD+ or NADP+ to a ketone and NADH or NADPH, respectively.

"Suitable reaction conditions" refers to those conditions in the biocatalytic reaction solution (e.g., ranges of enzyme loading, substrate loading, cofactor loading, temperature, pH, buffers, co-solvents, etc.) under which a ketoreductase polypeptide of the present disclosure is capable of converting compound (2c) to compound (1c). Exemplary "suitable reaction conditions" are provided in the present disclosure and illustrated by the Examples.

"Loading", such as in "compound loading" or "enzyme loading" refers to the concentration or amount of a component in a reaction mixture at the start of the reaction.

"Structural analog" refers to a chemical compound having a structure similar to that of a reference compound but differing in one or more atoms, functional groups or substructures.

"Substrate" in the context of a biocatalyst mediated process refers to the compound or molecule acted on by the biocatalyst. For example, an exemplary substrate for the ketoreductase biocatalyst in the process disclosed herein is compound (2c).

"Product" in the context of a biocatalyst mediated process refers to the compound or molecule resulting from the action of the biocatalyst. For example, an exemplary product for the ketoreductase biocatalyst in the process disclosed herein is compound (1c).

"Alkyl" refers to groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., (C1-C4)alkyl refers to an alkyl of 1 to 4 carbon atoms.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Exemplary aryls include phenyl, pyridyl, naphthyl and the like.

"Arylalkyl" refers to aryl -alkyl- groups preferably having from 1 to 6 carbon atoms inclusively in the alkyl moiety and from 6 to 14 carbon atoms inclusively in the aryl moiety. Such arylalkyl groups are exemplified by benzyl, phenethyl and the like.

"Cycloalkyl" refers to cyclic alkyl groups of from 3 to 12 carbon atoms inclusively having a single cyclic ring or multiple condensed rings which can be optionally substituted with from 1 to 3 alkyl groups. such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

"Cycloalkylalkyl" refers to cycloalkyl -alkyl- groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Bridged ring system" refers to a bicyclic or polycyclic ring system in which at least two rings have more than two common atoms. Such a system may contain isolated or conjugated unsaturation.

"Amino" refers to the group —$NH_2$. Substituted amino refers to the group —NHR', NR'R', and NR'R'R', where each $R^1$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylsulfonylamino, furanyl-oxy-sulfamino, and the like.

"Alkylamino" refers to a —NHR' group, where R is an alkyl, an N-oxide derivative, or a protected derivative thereof, e.g., methylamino, ethylamino, n-propylamino, iso-propylamino, n-butylamino, iso-butylamino, tert-butylamino, or methylamino-N-oxide, and the like.

"Aminoalkyl" refers to an alkyl group in which one or more of the hydrogen atoms is replaced with an amino group as defined herein, including a substituted amino group.

"Carboxy" refers to —COOH.

"Carbonyl" refers to —C(O)—, which may have a variety of substituents to form different carbonyl groups including acids, acid halides, aldehydes, amides, esters, and ketones.

"Alkyloxycarbonyl" refers to —C(O)OR', where $R^1$ is an alkyl, which can be optionally substituted.

"Aminocarbonyl" refers to —C(O)$NH_2$. Substituted aminocarbonyl refers to —C(O)NR'R', where the amino group NR'$R^1$ is as defined herein.

"Thiocarbonyl" refers to —C(S)—. Substituted thiocarbonyl refers to —C(S)R', where $R^1$ is a suitable substituent as described below.

"Aminothiocarbonyl" refers to a —C(S)NR'R', where the amino group —NR'$R^1$ is as defined herein.

"Halogen" or "halo" refers to fluoro, chloro, bromo and iodo.

"Hydroxy" refers to —OH.

"Cyano" refers to —CN.

"Sulfonyl" refers to —$SO_2$—. Substituted sulfonyl refers to —$SO_2$R', where $R^1$ is a suitable substituent as described below.

"Aminosulfonyl" refers to —$SO_2NH_2$. Substituted aminosulfonyl refers to —$SO_2$NR'R', where the amino group —NR'$R^1$ is as defined herein.

"Haloalkyl" refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1 C2) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl -alkyl- groups preferably having from 1 to 6 carbon atoms inclusively in the alkyl moiety and from 6 to 10 atoms inclusively in the heteroaryl moiety. Such heteroarylalkyl groups are exemplified by pyridylmethyl and the like.

"Heteroarylalkenyl" refers to heteroaryl -alkenyl- groups preferably having from 2 to 6 carbon atoms inclusively in the alkenyl moiety and from 6 to 10 atoms inclusively in the heteroaryl moiety.

"Heteroarylalkynyl" refers to heteroaryl -alkynyl- groups preferably having from 2 to 6 carbon atoms inclusively in the alkynyl moiety and from 6 to 10 atoms inclusively in the heteroaryl moiety.

"Heterocycle" and interchangeably "heterocycloalkyl" refer to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Bicycloalkyl" refers to two saturated or partially unsaturated fused or bridged polycyclic ring system with two or more common atoms. A "bridged bicycloalkyl ring system" refers to two saturated or partially unsaturated rings with more than two common atoms.

"Heterobicycloalkyl" refers to a bicycloalkyl in which 1 to 4 atoms within the ring is a heteroatom, inclusively selected from nitrogen, sulfur or oxygen. A "bridged heterobicycloalkyl ring system" refers to a heterobicycloalkyl with more than two common atoms.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

6.2 Processes and Ketoreductase Polypeptides

Generally, enzymes belonging to the ketoreductase (KRED) or carbonyl reductase class (EC1.1.1.184) are useful for the synthesis of optically active alcohols from the corresponding prostereoisomeric ketone substrates and by stereoselective reduction of corresponding aldehyde and ketone substrates. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED use a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP+) for the oxidation reaction. NADH and NADPH serve as electron donors, while NAD+ and NADP+ serve as electron acceptors. KREDs and other alcohol dehydrogenases can accept either the phosphorylated or the non-phosphorylated co-factor (in its oxidized and reduced state).

In one aspect, the present disclosure relates to a process for the conversion of compound (2c) to compound (1c) in enantiomeric excess, as shown in Scheme 1 above, by using a ketoreductase derived from *Lactobacillus*.

In some embodiments, the process for preparing compound (1c) in enantiomeric excess,

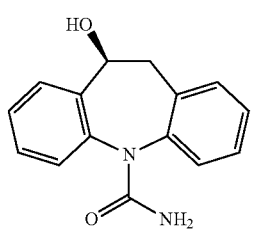
(1c)

comprises contacting compound (2c)

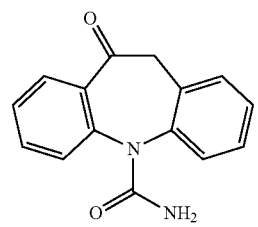
(2c)

with a ketoreductase polypeptide from *Lactobacillus*, wherein the ketoreductase is capable of converting compound (2c) to compound (1c) in enantiomeric excess, in presence of NADH or NADPH under suitable reaction conditions. In some embodiments, the ketoreductase is a non-naturally occurring ketoreductase derived from the ketoreductase of SEQ ID NO:2, as further described below.

In some embodiments, any of the processes for the conversion of compound (2c) to compound (1c) can be carried out for conversion of a structural analog of compound (2c) with an engineered polypeptide of the present disclosure (e.g., as described in Table 3 and elsewhere herein) in the presence of NADPH under suitable reaction conditions, thereby resulting in the preparation of the chiral alcohol of the corresponding analog of product compound (1c) in enantiomeric excess. Suitable reaction conditions for the conversion of analogs of compound (2c) to the chiral alcohol of the corresponding analogs of compound (1c) can be the same as used for compound (2c) or determined by the ordinary artisan based on the known properties of the analog compounds and routine experimentation in view of the guidance provided herein.

Accordingly, in some embodiments, the ketoreductases can be used to prepare in enantiomeric excess a chiral alcohol that is within the class of compounds represented by structural formula (1)

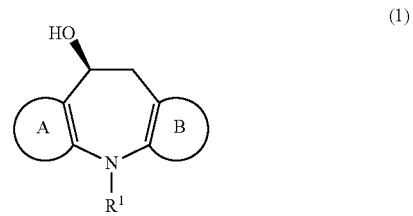
(1)

wherein
each ring A and B is independently an optionally substituted monocyclic aryl or heteroaryl,
$R^1$ is selected from hydrogen, hydroxy, halo, cyano, carboxy, and an optionally substituted alkyl, aminoalkyl, cycloalkyl, heterocycloalkyl, alkyloxycarbonyl, aminocarbonyl, aminothiocarbonyl, aminosulfonyl, and sulfonyl.

In some embodiments, $R^1$ is selected from H, —OH, —CN, —C(O)OR$^a$, —(C1-C4)alkyl-NR$^b$R$^c$, —C(O)NR$^b$R$^c$, —C(S)NR$^b$R$^c$, —SO$_2$NR$^b$R$^c$, —SO$_2$R$^b$, bicycloalkyl and heterobicycloalkyl, wherein R$^a$, R$^b$ and R$^c$ are each independently selected from H and an optionally substituted alkyl, alkenyl, alkynyl, cycloalkyl, heterocycloalkyl, aryl, and heteroaryl. Exemplary $R^1$ groups include, among others, —C(O)NH$_2$, dimethylaminopropyl, methylaminopropyl, and quinuclidinyl.

In some embodiments, the aryl or heteroaryl groups for rings A and B are selected from optionally substituted phenyl, pyridyl, or thienyl. Optional substituents on rings A and B include, but are not limited to —²H, —OH, —SH, halo, and optionally substituted alkyl, alkenyl, alkynyl, aryl, heteroaryl, alkoxy, and amino groups. Optional substituents on $R^1$ groups, where applicable, include but are not limited to, alkyl, alkenyl, alkynyl, cycloalkyl, heterocycloalkyl, aryl, and heteroaryl groups, which may be further optionally substituted. Compounds of structural formula (1) encompass structural analogs of compound (1c).

Thus, in some embodiments, the process for preparing a compound of structural formula (1) in enantiomeric excess, comprises contacting a compound of structural formula (2)

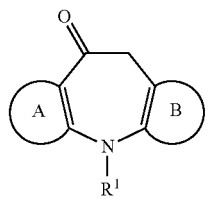

(2)

wherein rings A and B, and $R^1$ are defined above, with any of the ketoreductases described herein, wherein the ketoreductase is capable of converting compound (2) to compound (1) in enantiomeric excess, in presence of NADH or NADPH under suitable reaction conditions.

In some embodiments, the ketoreductases can be used to prepare in enantiomeric excess a chiral alcohol of the class of compounds represented by structural formula (1a),

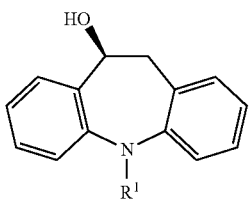

(1a)

wherein $R^1$ is selected from hydrogen, hydroxy, halo, cyano, carboxy, and an optionally substituted alkyl, aminoalkyl, cycloalkyl, heterocycloalkyl, alkyloxycarbonyl, aminocarbonyl, aminothiocarbonyl, aminosulfonyl, and sulfonyl.

In some embodiments, $R^1$ of structural formula (1a) is selected from —OH, —CN, —C(O)OR$^a$, —(C1-C4)alkyl-NR$^b$R$^c$, —C(O)NR$^b$R$^c$, —C(S)NR$^b$R$^c$, —SO$_2$NR$^b$R$^c$, —SO$_2$R$^b$, bicycloalkyl and heterobicycloalkyl, wherein R$^a$, R$^b$ and R$^c$ are each independently selected from H and an optionally substituted alkyl, alkenyl, alkynyl, cycloalkyl, heterocycloalkyl, aryl, and heteroaryl.

Accordingly, in some embodiments, the process for preparing a compound of structural formula (1a) in enantiomeric excess, comprises contacting a compound of structural formula (2a)

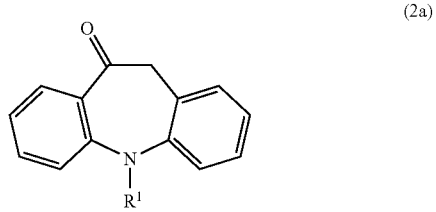

(2a)

wherein $R^1$ is defined above, with any of the ketoreductases described herein, wherein the ketoreductase is capable of converting compound (2a) to compound (1a) in enantiomeric excess, in presence of NADH or NADPH under suitable reaction conditions.

In some embodiments, a structural analog of compound (1c) is represented by structural formula (1b);

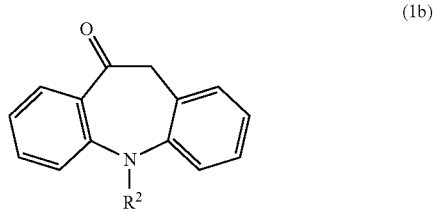

(1b)

wherein $R^2$ is selected from —OH, —C(O)OR$^d$, —C(O)NH$_2$, —CN, dimethylaminopropyl, methylaminopropyl, and quinuclidinyl, where R$^d$ is (C1-C4) alkyl.

Thus, in some embodiments, the process for preparing a compound of structural formula (1b) in enantiomeric excess, comprises contacting a compound of structural formula (2b)

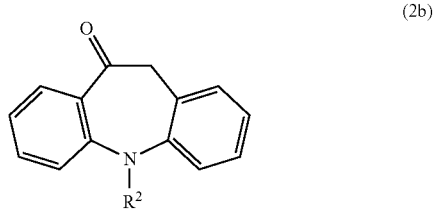

(2b)

wherein $R^2$ is defined above, with any of the ketoreductases described herein, wherein the ketoreductase is capable of converting compound (2b) to compound (1b) in enantiomeric excess, in presence of NADH or NADPH under suitable reaction conditions.

In some embodiments, the $R^2$ group for the compound of structural formula (2b) is —CN, such that the process results in the preparation of an enantiomeric excess of compound (1d)

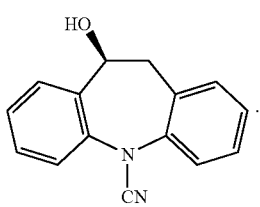
(1d)

While the processes using the ketoreductase can be used to directly convert compound (2c) to compound (1c), compound (1d) can also be used to prepare compound (1c) as shown in Scheme 2:

Scheme 2

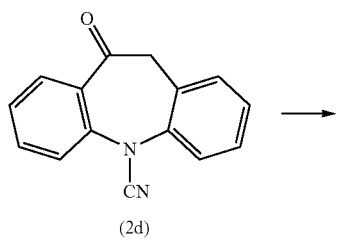
(2d)

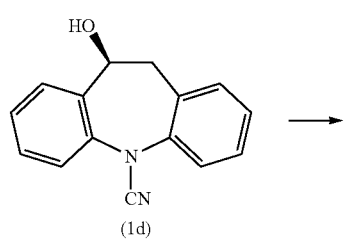
(1d)

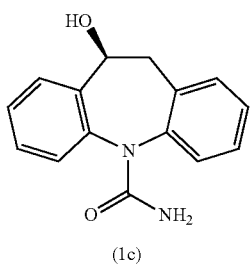
(1c)

Accordingly, the present disclosure also provides a process for preparing compound (1c) in enantiomeric excess by contacting compound (2d) with a ketoreductase under suitable reactions to form compound (1d) in enantiomeric excess; and converting compound (1d) to compound (1c). The conversion of compound (1d) to compound (1c) can use conventional techniques, such as hydrolysis of the cyano group to the amide (see, e.g., U.S. Pat. No. 4,008,241 and U.S. Pat. No. 4,629,700).

In some embodiments, the $R^2$ group for the compound of structural formula (2b) is—dimethylaminopropyl or methylaminopropyl, such that the process results in preparation of an enantiomeric excess of compound (1e)

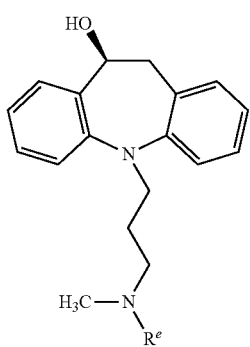
(1e)

where $R^e$ is H or methyl. Accordingly, in some embodiments, a process for preparing compound (1e) in enantiomeric excess comprises contacting compound (2e)

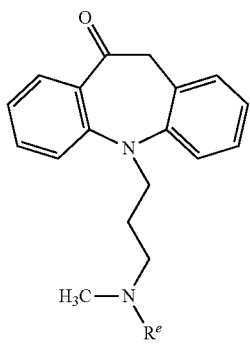
(2e)

where $R^e$ is defined above, with any of the ketoreductases described herein, wherein the ketoreductase is capable of converting compound (2e) to compound (1e) in enantiomeric excess, in presence of NADH or NADPH under suitable reaction conditions.

In some embodiments, the $R^2$ group for the compound of structural formula (2b) is—quinuclidinyl such that the process results in the preparation of an enantiomeric excess of compound (1f)

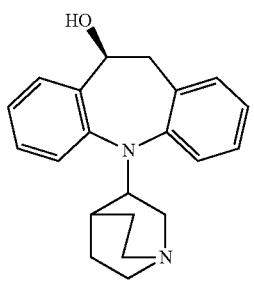
(1f)

Accordingly, in some embodiments, a process for preparing compound (1f) in enantiomeric excess comprises contacting compound (2f)

(2f)

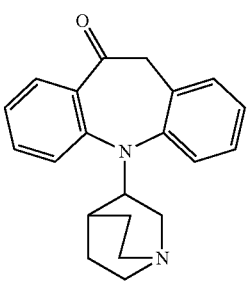

with any of the ketoreductases described herein, wherein the ketoreductase is capable of converting compound (2f) to compound (1f) in enantiomeric excess, in presence of NADH or NADPH under suitable reaction conditions. As will be apparent to the person of ordinary skill in the art, compound (1f) and compound (1e) are metabolites of Imipramine and Quinupramine, respectively (see, e.g., Chen et al., 1997, J Chromatogr B Biomed Sci Appl. 693(1):153-8; Nielsen et al., 1993, J Chromatogr. 612(1):87-95), which are tricyclic antidepressants used for treatment of depression and enuresis. Imipramine and Quinupramine have the following structures:

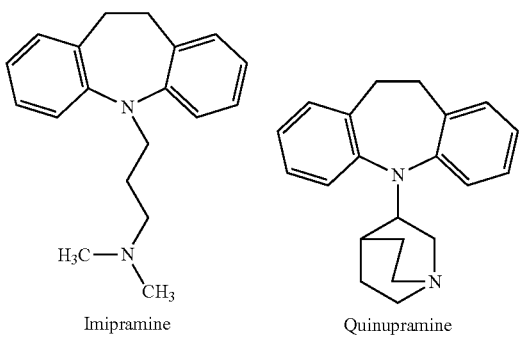

Imipramine            Quinupramine

In some embodiments, the process for the conversion of a structural analog of compound (2c) to the corresponding chiral alcohol can be carried out, wherein the analog of compound (2c) is a deuterated version of the compound (2c) (i.e., a molecule having the same structure as compound (2c) but with one or more the hydrogen atoms of compound (2c) substituted with a deuterium atom) (see, e.g., U.S. Pat. No. 7,705,036 B2). Similarly, the processes for the conversion of an analog of compound (2c) to an analog of compound (1c) can be carried out with the deuterated version of any of the above described compounds of formula (2), compounds of formula (2a), compounds of formula (2b), compounds of formula (2d), compounds of formula (2e), and compounds of formula (2f) described above.

As noted herein, the process for conversion of the prostereoisomeric ketone to the corresponding chiral alcohol uses a ketoreductase from *Lactobacillus*. In some embodiments, the ketoreductase comprises a non-naturally occurring, engineered polypeptide with improved enzymatic properties for the conversion of compound (2c) or a structural analog thereof to compound (1c) or the corresponding structural analog, relative to the naturally occurring ketoreductase polypeptide of SEQ ID NO: 2, including, among others, increased conversion rates, high stereoselectivity, increased solvent stability, and increased thermal stability.

In some embodiments, the non-naturally occurring, engineered ketoreductase polypeptides disclosed herein are capable of carrying out the conversion with high enantiomeric excess (e.g., at least about 99% e.e.), increased activity (e.g., at least about 10-fold increased activity relative to the reference polypeptide SEQ ID NO:4 or 6), high percent conversion (e.g., at least about 90% conversion in 24 h), in the presence of high substrate loadings (e.g., at least about 50 g/L to 100 g/L of compound (2c)).

In some embodiments of the process, the ketoreductase capable of converting compound (2c) or structural analog thereof to compound (1c) or corresponding structural analog in enantiomeric excess comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide selected from SEQ ID NO: 6, 8, 10, 12, 14, 16, 18, 20, 22, 24, 26, 28, 30, 32, 34, 36, and 38, as further described below.

In some embodiments, the ketoreductase is a non-naturally occurring ketoreductase polypeptide comprising an amino acid sequence that has at least 80%, 85%, 86%, 87%, 88%, 89%, 90%, 91%, 92%, 93%, 94%, 95%, 96%, 97%, 98%, or 99% sequence identity to the reference polypeptide of SEQ ID NO:10.

In some embodiments, the ketoreductase is a non-naturally occurring ketoreductase polypeptide comprising an amino acid sequence that has at least 80%, 85%, 86%, 87%, 88%, 89%, 90%, 91%, 92%, 93%, 94%, 95%, 96%, 97%, 98%, or 99% sequence identity to the reference polypeptide of SEQ ID NO:16.

In some embodiments, the ketoreductase is a non-naturally occurring ketoreductase polypeptide comprising an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide of SEQ ID NO:36.

Exemplary embodiments of ketoreductases that can be used in the process are disclosed in more detail below, including the ketoreductase polypeptides disclosed in Table 3, and it is to be understood that any of the ketoreductases disclosed herein is applicable to any of the process described in this section.

In the present disclosure, the processes are carried out under suitable reaction conditions, and contemplate ranges of suitable reaction conditions that can be used in the conversion reactions. These include, but are not limited to, ranges of polypeptide loading, conditions with the polypeptide immobilized on a solid support, substrate loading, cofactor loading, pH, temperature, buffer, solvent system, atmospheric pressure, and reaction time. The present disclosure also contemplates that the methods comprising the biocatalytic conversion described above using an engineered polypeptide of the disclosure can further comprise chemical steps of compound (1c) product, or corresponding structural analog work-up, extraction, isolation, purification, and/or crystallization, each of which can be carried out under a range of conditions.

In the processes herein, the ketoreductase is used in an amount capable of producing the desired amount of product, e.g., compound (1c), or desired percent conversion of substrate to product under the reaction condition used. As will be apparent to the skilled artisan, non-natural, engineered ketoreductases with increased enzymatic activity and higher percentage conversion efficiency allows the use of lower concentrations of the engineered polypeptide. The use of lower concentration of engineered polypeptide in turn reduces the amount of residual protein that may need to be removed in subsequent steps for purification of the product compound. In some embodiments, the processes of the present disclosure can be carried out wherein the reaction conditions comprise an engineered polypeptide concentration of about 0.1 g/L to about 10 g/L, about 0.1 g/L to about 5 g/L, about 0.1 g/L to about 2 g/L, or about 0.1 g/L to about 1.0 g/L. In some embodiments, the ketoreductase polypeptide concentration is at about 10 g/L, about 5 g/L, about 4 g/L, about 2 g/L, about 1 g/L, about 0.5 g/L, about 0.2 g/L or about 0.1 g/L. In some embodiments, the reaction conditions for the biocatalytic conversion processes disclosed herein, include conditions wherein the ketoreductase polypeptide is immobilized on a solid support. Such immobilization can allow for reuse of the polypeptide.

In some embodiments, the processes can be carried out under reaction conditions comprising a compound (2c) loading of about 1 g/L to about 400 g/L, about 10 g/L to about 400 g/L, about 20 g/L to about 400 g/L, about 40 g/L to about 400 g/L, about 50 g/L to about 400 g/L. about 75 g/L to about 400 g/L, about 100 g/L to about 400 g/L, about 125 g/L to about 400 g/L, about 150 g/L to about 400 g/L, about 175 g/L to about 400 g/L, about 200 g/L to about 400 g/L, or even greater. In some embodiments, the reaction conditions comprise a compound (2c) loading of about 1 g/L to about 200 g/L, about 10 g/L to about 200 g/L, about 20 g/L to about 200 g/L, about 40 g/L to about 200 g/L, about 50 g/L to about 200 g/L. about 75 g/L to about 200 g/L, about 100 g/L to about 200 g/L, or about 50 g/L to about 150 g/L. In some embodiments, the reaction conditions comprise a compound (2c) loading of about 1 g/L, about 10 g/L, about 20 g/L, about 40 g/L, about 50 g/L, about 75 g/L, about 100 g/L, about 125 g/L, about 150 g/L, about 175 g/L, about 200 g/L, about 300 g/L, or about 400 g/L. While the values for substrate loadings provided herein are based on the molecular weight of compound (2c), it also is contemplated that the equivalent molar amounts of various hydrates and salts of compound (2c) as well as structural analogs, e.g., compounds encompassed by structural formula (2), structural formula (2a), structural formula (2b), structural formula (2d), structural formula (2e) and structural formula (2f), also can be used in the processes. The substrate loading used in the processes herein can take into account, among others, substrate solubility in the reaction solvent, tolerability of the biocatalyst to the substrate loading, and the percent conversion under the reaction conditions used.

In the embodiments herein, the reaction conditions comprise a temperature suitable for activity of the biocatalyst and desired conversion of substrate to product. In some embodiments, the use of engineered polypeptides having increased thermal stability relative to the naturally occurring ketoreductase polypeptide of SEQ ID NO: 2 allows the processes, e.g., conversion of compound (2c) to compound (1c), to be carried out at higher temperatures, which can result in increased conversion rates and improved substrate solubility characteristics. One of skill in the art can assess the advantages of carrying out the reaction at a higher temperature and the potential disadvantages of product degradation and enzyme inactivation at the higher temperatures. In some embodiments, the processes can be carried out under reaction conditions comprising a temperature of about 20° C. to about 60° C., about 25° C. to about 60° C., about 30° C. to about 60° C., about 35° C. to about 60° C., about 40° C. to about 60° C., about 45° C. to about 60° C., about 45° C. to about 55° C., or about 50° C. to about 55° C. In some embodiments, the temperature during the enzymatic reaction can be maintained at ambient (e.g., 25° C.), 27° C., 30° C., 32° C., 35° C., 37° C., 40° C.; 45° C., 50° C., 55° C. or 60° C. or in some embodiments adjusted over a temperature profile during the course of the reaction.

In some embodiments, the processes herein for preparing compound (1c) and structural analogs thereof are carried out under reaction conditions at a desired pH or within a desired pH range by the addition of an acid or a base. In some embodiments, this may be done during the course of the reaction. In some embodiments, the pH of the reaction mixture may change or be changed during the course of the reaction. Thus, in some embodiments the pH may be controlled by using an aqueous solvent that comprises a buffer. Suitable buffers to maintain desired pH ranges are known in the art and include, but are not limited to, phosphate buffer, triethanolamine (TEA) buffer, and the like. Combinations of buffering and acid or base addition may also be used.

In some embodiments, the processes for preparing compound (1c) or structural analogs thereof can be carried out under reaction conditions comprising a pH of about 6 to about 12, a pH or about 6 to about 11, a pH of about 7 to about 11, a pH of about 7 to about 10, a pH of about 8 to about 10, a pH of about 9 to about 10, a pH of about 8 to about 9.5, or a pH of about 8 to about 9. In some embodiments, the reaction conditions comprise a pH of about 6, a pH of about 6.5, a pH of about 7, a pH of about 7.5, a pH of about 8, a pH of about 8.5, a pH of about 9, a pH of about 9.5, a pH of about 10, a pH of about 10.5, a pH of about 11, a pH of about 11.5 or a pH of about 12. A person of ordinary skill in the art can use an appropriate pH or a range of pH by considering, by way of example and not limitation, stability and activity of the ketoreductase, stability of substrate and product, and stability of the cofactor.

Generally, the processes of the present disclosure are carried out in a solvent. Suitable solvents include water, aqueous buffer solutions, organic solvents, and/or co-solvent systems, which generally comprise aqueous solvents and organic solvents.

In some embodiments, the processes can be carried out under reaction conditions comprising an aqueous buffer solution, an organic solvent, or a co-solvent system. In some embodiments, the buffer solution is selected from TEA, for example, of about 0.025 M to about 0.25 M TEA, and potassium phosphate, for example, about 0.025 M to about 0.25 M phosphate. In some embodiments, the co-solvent system comprises about 95% (v/v) to about 5% (v/v) of an aqueous buffer solution (e.g., about 0.1 M TEA), and about 5% (v/v) to about 95% (v/v) of an organic solvent solution (e.g., IPA). In some embodiments, the co-solvent system comprises about 30% (v/v) to about 70% (v/v) of an aqueous buffer solution (e.g., about 0.1 M TEA) and about 70% (v/v) to about 30% (v/v) of an organic solvent solution (e.g., IPA). In some embodiments, the reaction conditions comprise water as a suitable solvent with no buffer present.

In some embodiments, the co-solvent system comprises an aqueous buffer solution and IPA, wherein the IPA concentration is about 5% (v/v) to about 95% (v/v), about 10% (v/v) to about 90%, (v/v) about 15% (v/v) to about 90% (v/v), about 20% (v/v) to about 90% (v/v), about 25% (v/v) to about 80% (v/v), about 25% (v/v) to about 75% (v/v), about 35% (v/v) to about 75% (v/v), about 45% (v/v) to about 75% (v/v), about 55% (v/v) to about 75% (v/v), about 60% (v/v) to about 70% (v/v), or about 60% (v/v) to about 65% (v/v). In some embodiments, the IPA concentration is at least about 25% (v/v), at least about 35% (v/v), at least about 45% (v/v), at least about 55% (v/v), about 60% (v/v), about 65% (v/v), about 70% (v/v), about 75% (v/v), about 80%, about 85% (v/v), about 90% (v/v) or about 95% (v/v). In some embodiments, the reaction conditions comprise a co-solvent system of 0.1 M TEA buffer and about 60% (v/v) to about 70% (v/v) IPA. In some embodiments, the reaction conditions comprise a co-solvent system of about 0.1 M TEA buffer and about 95% (v/v), about 0.1 M TEA buffer and about 90% (v/v) IPA, about 0.1 M TEA buffer and about 85% (v/v) IPA, about 0.1 M TEA buffer and about 80% (v/v) IPA, about 0.1 M TEA buffer and about 75% (v/v) IPA, about 0.1 M TEA buffer and about 70% (v/v) IPA, about 0.1 M TEA buffer and about 65% (v/v) IPA, about 0.1 M TEA buffer and about 65% (v/v) IPA, or about 0.1 M TEA buffer and about 60% (v/v) IPA.

Generally, in the processes of the present disclosure, an electron donor is used in the reduction reaction carried out by the ketoreductase. In some embodiments, the electron donor is a cofactor. Suitable cofactors include, but are not limited to, NADP (nicotinamide adenine dinucleotide phosphate), NADPH (the reduced form of NADP$^+$), NAD (nicotinamide adenine dinucleotide) and NADH (the reduced form of NAD$^+$). Generally, the reduced form of the cofactor is added to the reaction mixture. Accordingly, in some embodiments, the processes are carried out in presence of an electron donor selected from NADPH cofactor or NADH cofactor. In some embodiments, the electron donor is NADPH cofactor. In some embodiments, the process can be carried out wherein the reaction conditions comprise an NADH or NADPH cofactor concentration of about 0.03 to about 1 g/L, 0.03 to about 0.8 g/L, about 0.03 to about 0.5 g/L, about 0.05 to about 0.3 g/L, about 0.05 to about 0.2 g/L, or about 0.1 to about 0.2 g/L. In some embodiments, the process is carried out under NADH or NADPH cofactor concentration of about 1 g/L, about 0.8 g/L, about 0.5 g/L, about 0.3 g/L, about 0.2 g/L, about 0.1 g/L, about 0.05 g/L, or about 0.03 g/L.

In some embodiments of the process, an optional cofactor recycling system, also referred to as a cofactor regeneration system, can be used to regenerate cofactor NADPH/NADH from NADP+/NAD+ produced in the enzymatic reaction. A cofactor regeneration system refers to a set of reactants that participate in a reaction that reduces the oxidized form of the cofactor (e.g., NADP to NADPH). Cofactors oxidized by the polypeptide reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst, that catalyzes the reduction of the oxidized form of the cofactor by the reductant. Cofactor regeneration systems to regenerate NADH or NADPH from NAD$^+$ or NADP$^+$, respectively, are known in the art and can be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either NADP$^+$/NADPH or NAD$^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) may also be suitable. See, e.g., PCT publication WO 2000/053731, which is incorporated herein by reference.

In some embodiments, the cofactor recycling system comprises glucose dehydrogenase (GDH), which is a NAD$^+$ or NADP$^+$-dependent enzyme that catalyzes the conversion of D-glucose and NAD$^+$ or NADP$^+$ to gluconic acid and NADH or NADPH, respectively. Glucose dehydrogenases suitable for use in the practice of the processes described herein include naturally occurring glucose dehydrogenases as well as non-naturally occurring glucose dehydrogenases. Naturally occurring glucose dehydrogenase encoding genes have been reported in the literature, e.g., the *Bacillus subtilis* 61297 GDH gene, *B. cereus* ATCC 14579 and *B. megaterium*. Non-naturally occurring glucose dehydrogenases generated using, for example, mutagenesis, directed evolution, and the like and are provided in PCT publication WO 2005/018579, and US publication Nos. 2005/0095619 and 2005/0153417. All of these sequences are incorporated herein by reference.

In some embodiments, the co-factor regenerating system comprises a formate dehydrogenase, which is a NAD$^+$ or NADP$^+$-dependent enzyme that catalyzes the conversion of formate and NAD$^+$ or NADP$^+$ to carbon dioxide and NADH or NADPH, respectively. Formate dehydrogenases suitable for use as cofactor regenerating systems in the ketoreductase reactions described herein include naturally occurring and non-naturally occurring formate dehydrogenases. Suitable formate dehydrogenases are described in PCT publication WO 2005/018579, incorporated herein by reference. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. A base or buffer may be used to provide the desired pH.

In some embodiments, the co-factor regenerating system comprises a secondary alcohol dehydrogenase, which is an NAD$^+$ or NADP$^+$-dependent enzyme that catalyzes the conversion of a secondary alcohol and NAD$^+$ or NADP$^+$ to a ketone and NADH or NADPH, respectively. Secondary alcohol dehydrogenases suitable for use as cofactor regenerating systems in the processes described herein include naturally occurring and non-naturally occurring ketoreductases. Naturally occurring secondary alcohol dehydrogenases include known alcohol dehydrogenases from, by way of example and not limitation, *Thermoanerobium brockii*, *Rhodococcus erythropolis*, *Lactobacillus kefir*, and *Lactobacillus brevis*, and non-naturally occurring secondary alcohol dehydrogenases include engineered alcohol dehydrogenases derived therefrom. In some embodiments, non-naturally occurring ketoreductases engineered for thermo- and solvent stability can be used. Such ketoreductases are described in the present application and the patent publications US 20080318295A1; US 20090093031A1; US 20090155863A1; US 20090162909A1; US 20090191605A1; US 20100055751A1; WO/2010/025238A2; WO/2010/025287A2; and US 20100062499A1; each of which are incorporated by reference herein.

As will be apparent from this disclosure, the engineered ketoreductase polypeptides described herein are capable of converting IPA to acetone to regenerate the cofactor NADH/NADPH for NAD+/NADP+, respectively. Thus, in some embodiments of the processes for carrying out the conversion of compound (2c) or structural analogs thereof to compound (1c) or its corresponding structural analogs, the ketoreductase of the cofactor regeneration system is the engineered ketoreductase polypeptides of present disclosure, and used with a secondary alcohol as a reductant to recycle the NADPH or NADH cofactor in the reaction mixture.

Suitable secondary alcohols useful in cofactor regenerating systems include lower secondary alkanols and aryl-alkyl carbinols. Exemplary lower secondary alcohols include, but are not limited to, isopropanol, 2-butanol, 3-methyl-2-butanol, 2-pentanol, 3-pentanol, 3,3-dimethyl-2-butanol, and the like. In some embodiments, the secondary alcohol is isopropanol (IPA). Suitable aryl-alkyl carbinols include unsubstituted and substituted 1-arylethanols.

In some embodiments, the processes can be carried out without adding NADPH or NADH cofactor during the reaction and without any other enzyme systems present (e.g., glucose dehydrogenase, or formate dehydrogenase).

In some embodiments, the processes of the disclosure can be carried out wherein no cofactor recycling enzyme is present other than the engineered polypeptide. For example, the reaction conditions can comprise an IPA concentration of about 55-75% (v/v), an NADPH or NADH cofactor loading of about 0.03-0.5 g/L, and wherein no cofactor recycling enzyme is present other than the engineered ketoreductase polypeptide.

In some embodiments where the cofactor recycling system produces a volatile product, such as acetone from isopropanol, the volatile product can be removed by sparging the reaction solution with a non-reactive gas or by applying a vacuum to lower the reaction pressure and removing the volatile present in the gas phase. A non-reactive gas is any gas that does not react with the reaction components. Various non-reactive gases include nitrogen and noble gases (e.g., inert gases). In some embodiments, the non-reactive gas is nitrogen gas. For example, acetone formed by oxidation of isopropanol can be removed by sparging the reaction solution with nitrogen gas or applying a vacuum to the reaction solution and removing the acetone from the gas phase by an acetone trap, such as a condenser or other cold trap.

In the embodiments herein, the polypeptides carrying out the conversion of compound (2c) or structural analog thereof to compound (1c) or corresponding structural analog, and any additional enzymes of the optional cofactor regeneration system, may be added to the reaction mixture in the form of the purified enzymes, whole cells transformed with gene(s) encoding the enzymes, and/or cell extracts and/or lysates of such cells.

In some embodiments, the gene(s) encoding the ketoreductase polypeptides and the optional cofactor regeneration enzymes can be transformed into host cells separately or together into the same host cell for expression of the enzymes. Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semisolid (e.g., a crude paste). In some embodiments, the transformed cells, cell extracts, lysates, or isolated enzyme, can be immobilized on a solid support and the conversion reactions carried by contacting the solid support with the substrate compound.

Generally, the order of addition of reactants (e.g., substrate, cofactor, polypeptide, etc.) is not critical to the processes of the present disclosure. The reactants may be added together at the same time to a solvent (e.g., monophasic solvent, biphasic aqueous co-solvent system, and the like), or alternatively, some of the reactants may be added separately, and some together at different time points.

In some embodiments, the process for preparing the compound (1c) or structural analogs thereof can be carried out using any combination of a mixture and reaction conditions disclosed above or elsewhere herein. Accordingly, in some embodiments, the processes described herein comprise the following reaction condition: (a) the ketoreductase polypeptide is at about 0.1 g/L to about 1 g/L; (b) compound (2c) is at a loading of about 100 g/L to about 200/g/L; (c) NADP(H) is about 0.1 g/L to about 0.01 g/L; (d) a co-solvent solution of an aqueous buffer, and IPA of about 50% to about 70% (v/v), and (e) a temperature of about 45° C. to about 60° C.

In some embodiments, the processes described herein comprise the following reaction conditions: (a) the ketoreductase polypeptide is at about 1 g/L to about 3 g/L; (b) compound (2c) is at a loading concentration of about 50 g/L to about 175 g/L; (c) NADP(H) is about 0.1 g/L to about 0.5 g/L; (d) a co-solvent solution of an aqueous buffer and IPA of about 50% to about 70% (v/v), and (e) a temperature of about 45° C. to about 60° C.

In some embodiments, the processes described herein comprise the following reaction conditions: (a) the ketoreductase polypeptide is at about 1 g/L to about 3 g/L to about 10 g/L; (b) compound 2(c) is at a loading concentration of about 50 g/L to about 175 g/L; (c) NADP(H) is about 0.5 g/L to about 1 g/L; (d) a co-solvent solution of an aqueous buffer and IPA of about 50% to about 70% (v/v), and (e) a temperature of about 45° C. to about 60° C.

In some embodiments, in the process for the conversion of compound (2c) to compound (1c), compound (2c) is at a loading of about 50 g/L to about 200 g/L and the process results in at least about 91%, 92%, 93%, 94%, 95%, 96%, 97%, 98%, 99% or greater conversion of compound (2c) to compound (1c) in 24 h or less.

In some embodiments, in the process for the conversion of compound (2c) to compound (1c), compound (2c) is at a loading of about 50 g/L to about 200 g/L and the process results in enantiomeric excess of at least about 91%, 92%, 93%, 94%, 95%, 96%, 97%, 98%, 99% or greater of compound (1c) in 24 h or less.

As noted throughout this disclosure, eslicarbazepine acetate is the prodrug form of eslicarbazepine (i.e., compound (1c)). Upon oral administration, eslicarbazepine acetate is efficiently absorbed in the gastrointestinal tract and metabolized to eslicarbazepine. Hence, the processes described herein for efficient synthesis of eslicarbazepine also provides an improved method for preparation of eslicarbazepine acetate and its structural analogs.

Accordingly, in some embodiments, a method for preparing compound (3) or structural analog thereof in enantiomeric excess,

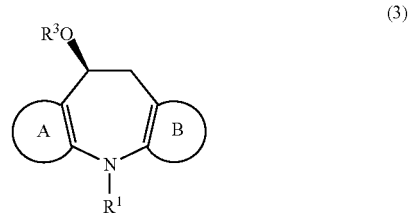

(3)

wherein,
rings A and B are as defined for structural formula (1) above;

$R^1$ is selected from hydrogen, hydroxy, halo, cyano, carboxy, and an optionally substituted alkyl, aminoalkyl, cycloalkyl, heterocycloalkyl, alkyloxycarbonyl, aminocarbonyl, aminothiocarbonyl, aminosulfonyl, and sulfonyl; and $R^3$ is a hydroxyl protecting group or —C(O)$R^4$, wherein $R^4$ is selected from H, alkyl, aminoalkyl, haloalkyl, aralkyl, cycloalkyl, cycloalkylalkyl, alkoxy, aryl, substituted phenyl or pyridyl, comprises a step of converting compound (2) to compound (1) by any of the processes described herein for preparing compound (1).

As noted above, in some embodiments, $R^1$ of structural formula (3) can be selected from —OH, —CN, —C(O)O$R^a$, —(C1-C4)alkyl-N$R^b R^c$, —C(O)N$R^b R^c$, —C(S)N$R^b R^c$, —SO$_2$N$R^b R^c$, —SO$_2 R^b$, bicycloalkyl, and heterobicycloalkyl, wherein $R^a$, $R^b$ and $R^c$ are each independently selected from H and an optionally substituted alkyl, alkenyl, alkynyl, cycloalkyl, heterocycloalkyl, aryl, and heteroaryl.

A protecting group when attached to a reactive functional group in a molecule, masks, reduces or prevents the reactivity of the functional group. Examples of hydroxyl protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative hydroxyl protecting groups include, but are not limited to, lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

In some embodiments, a method for preparing compound (4) or structural analog thereof in enantiomeric excess,

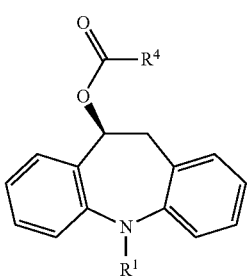

(4)

wherein $R^1$ is as defined above; and $R^4$ is selected from H, alkyl, aminoalkyl, haloalkyl, aralkyl, cycloalkyl, cycloalkylalkyl, alkoxy, aryl, particularly an optionally substituted phenyl or pyridyl, comprises a step of converting compound (2a) to compound (1a) by any of the processes described herein for preparing compound (1a).

In some embodiments, a method for preparing compound (5) or structural analog thereof in enantiomeric excess,

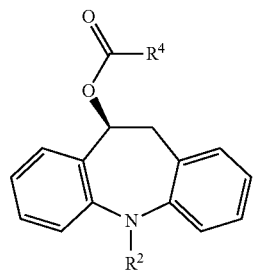

(5)

wherein $R^2$ is selected from —OH, —C(O)O$R^d$, —C(O)NH$_2$, —CN, dimethylaminopropyl, methylaminopropyl, and quinuclidinyl, where $R^d$ is (C1-C4) alkyl; and $R^4$ is selected from H, alkyl, aminoalkyl, haloalkyl, aralkyl, cycloalkyl, cycloalkylalkyl, alkoxy, aryl, particularly an optionally substituted phenyl or pyridyl;

comprises a step of converting compound (2b) to compound (1b) by any of the processes described herein for preparing compound (1b).

In some embodiments, a method for preparing compound (6) in enantiomeric excess,

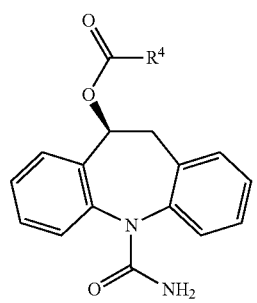

(6)

wherein $R^4$ is selected from H, alkyl, aminoalkyl, haloalkyl, aralkyl, cycloalkyl, cycloalkylalkyl, alkoxy, aryl, particularly an optionally substituted phenyl or pyridyl;

comprises a step of converting compound (2c) to compound (1c) in enantiomeric excess by any of the processes described above for preparing compound (1c).

In some embodiments, a method for preparing compound (6) in enantiomeric excess, wherein $R^4$ is methyl (i.e., compound (6a)),

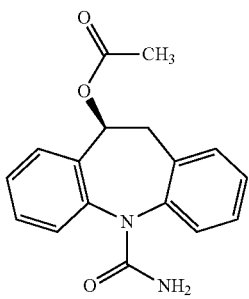

(6a)

comprises a step of converting compound (2c) to compound (1c) in enantiomeric excess by any of the processes described herein for preparing compound (1c) in enantiomeric excess.

In some embodiments, the method for preparing compound (6a) in enantiomeric excess can further comprise a step of converting compound (1c) to compound (6a). In some embodiments, preparing compound (6a) from compound (1c) is by use of an acylating agent (see, e.g., U.S. Pat. No. 5,753,646, incorporated herein by reference).

In the processes of the present disclosure, the conversion reactions are mediated by ketoreductases from *Lactobacillus*. In some embodiments, the ketoreductases are non-natural, engineered ketoreductases that have residue differences as compared to the naturally occurring ketoreductase of *L. kefir* represented by SEQ ID NO:2. These differences occur at residue positions that can affect enzyme activity, stereoselectivity, thermostability, solvent stability, polypeptide expression, co-factor affinity, or various combinations thereof. Table 2 provides a correlation of amino acid residue positions and the associated role in enzyme properties.

TABLE 2

Structural locations useful for engineered ketoreductase polypeptides

| Position | Structural location | Associated functional properties |
|---|---|---|
| X17 | NADPH-Binding Site | Activity/Thermostability |
| X21 | Surface | Thermostability |
| X25 | Surface | Thermostability/Solvent stability |
| X29 | Surface | Thermostability/Solvent stability |
| X40 | NADPH-Binding Site | Tight binding of NADPH to enzyme |
| X43 | Surface | Thermostability |
| X64 | NADPH-Binding Site | Interacts with NADPH Adenine ring |
| X71 | Surface | Thermostability/Solvent stability |
| X76 | Surface | Solvent stability |
| X80 | Surface | Solvent stability |
| X87 | Tetramer interface | Activity/Thermostability/Solvent stability |
| X93 | Second sphere active site | Thermostability |
| X94 | Second sphere active site | Thermostability |
| X95 | Second sphere active site | Activity/Thermostability/Solvent Stability |
| X96 | Second sphere active site | Activity/Thermostability/Solvent Stability |
| X99 | Dimer-tetramer interface | Thermostability/Solvent stability |
| X108 | Dimer-tetramer interface | Thermostability/Solvent stability |
| X117 | Core | Thermostability/Solvent stability |
| X127 | Second sphere active site | Thermostability/Solvent stability |
| X131 | Surface | Activity/Thermostability |
| X144 | Active site | Activity |
| X145 | Active site | Activity |
| X147 | Dimer-tetramer interface/core | Activity/Thermostability/Solvent stability |
| X148 | Dimer-tetramer interface | Thermostability/Solvent stability |
| X150 | Active site | Activity |
| X152 | Second sphere active site | Activity |
| X153 | Second sphere active site | Activity |
| X155 | Position interacting with 95 | Activity |
| X157 | Core | Activity/Thermostability/Solvent Stability |
| X173 | Dimer interface | Activity/Thermostability/Solvent Stability |
| X190 | Active site | Activity |
| X194 | Surface | Activity |
| X195 | Second sphere active site | Thermostability |
| X196 | Active site | Activity |
| X199 | Active site | Activity |
| X200 | Surface | Thermostability |
| X201 | Active site | Activity |
| X202 | Flexible loop | Activity |
| X203 | Flexible loop | Activity |
| X204 | Flexible loop | Activity |

TABLE 2-continued

Structural locations useful for engineered ketoreductase polypeptides

| Position | Structural location | Associated functional properties |
|---|---|---|
| X205 | Flexible loop | Activity |
| X206 | Flexible loop | Activity |
| X207 | Flexible loop | Activity |
| X211 | Second sphere active site | Activity |
| X221 | Surface | Thermostability/Solvent stability |
| X223 | Core | Thermostability/Solvent stability |
| X226 | Dimer-tetramer interface | Thermostability/Solvent stability |
| X233 | Surface | Activity |
| X249 | Active site | Activity |

The structure-function information was obtained by identifying engineered ketoreductases active in the conversion of compound (2c) to compound (1c), where the identified ketoreductases have various residue differences from the reference polypeptide of SEQ ID NO:2 and displayed certain desirable properties, including among others, desirable changes in enzyme activity, stereoselectivity, thermostability, solvent stability, co-factor affinity, polypeptide expression, or various combinations thereof. The odd numbered sequence identifiers (i.e., SEQ ID NOs) refer to the nucleotide sequence encoding the amino acid sequence provided by the even numbered SEQ ID NOs, and the sequences are provided in the electronic Sequence Listing file accompanying this disclosure, which is hereby incorporated by reference herein. The amino acid residue differences are based on comparison to the reference sequence of SEQ ID NO: 2. The activity of each engineered polypeptide relative to the reference polypeptide of SEQ ID NO: 4 was determined as conversion of substrate of compound (2c) to product of compound (1c) over a 24 h period at room temperature in a high-throughput (HTP) 96-well plate format assay of cell lysates containing the engineered polypeptides. General HTP assay protocol and reaction conditions were as follows: a total 200 µL reaction volume in a deep-well 96-well plates containing 10 µL of polypeptide clear lysate, 0.05 g/L NADP+, 70% isopropyl alcohol (IPA), 0% to 1% acetone, 5.0 g/L to 100 g/L substrate, and 0% to 5% DMSO. Specific modifications of the HTP assay protocols at different rounds of evolution are as noted in Table 3. Additional assay protocols and experimental details useful for determining engineered polypeptide activities are provided in the Examples. The levels of activity (i.e., "+" "++" "+++" etc.) are defined as follows: "+" indicates at least equal to but less than 2 times the activity of SEQ ID NO: 4; "++" indicates at least 2 times but less than 10 times the activity of SEQ ID NO: 4; "+++" indicates at least 10 times but less than 25 times the activity of SEQ ID NO: 4; "++++" indicates at least 25 times the activity of SEQ ID NO: 4.

TABLE 3

| SEQ ID NO (NT/AA) | RESIDUE DIFFERENCES (RELATIVE SEQ ID NO: 2) | ACTIVITY (RELATIVE TO SEQ ID NO: 4) |
|---|---|---|
| 1/2 | — | −[1] |
| 3/4 | A80T; A94G; S96V; E145L; L153T; Y190P; V196L; I226V; Y249W; | +[1] |
| 5/6 | A80T; A94G; S96V; E145L; L153T; Y190P; V196L; I226V; Y249W | +[1] |
| 7/8 | A80T; A94G; S96V; E145L; F147Q; L153T; Y190P; V196L; I226V; Y249W | ++[1] |
| 9/10 | A80T; A94G; S96V; E145L; L153T; Y190P; V196L; I226V; | +[1] |
| 11/12 | A80T; A94G; S96V; E145L; D150L; L153T; Y190P; V196M; L199M; I226V | ++[1] |
| 13/14 | A80T; S96V; I144V; E145L; L153T; Y190P; V196M; L199M; I226V; Y249F | ++[1] |
| 15/16 | A80T; A94G; S96V; E145L; F147Q; L153T; Y190P; V196M; L199M; I226V | ++[1] |
| 17/18 | A80T; A94G; V95M; S96V; I144V; E145L; F147Q; L153T; Y190P; V196M; I226V; Y249F | ++[1] |
| 19/20 | A80T; A94G; V95M; S96V; I144V; E145L; L153T; Y190P; V196L; L199M; I226V | ++[1] |
| 21/22 | L17M; A80T; A94G; S96V; I144V; E145L; F147M; D150L; L153T; Y190P; P194R; V196M; L199M; I226V | +++[2] |
| 23/24 | V43R; A64V; T71P; A80T; V87L; A94G; S96V; E145L; F147Q; L153T; D173L; Y190P; V196M; L199M; I226V | +++[1] |
| 25/26 | V43R; A64V; A80T; A94G; S96V; E145L; F147Q; L153T; D173L; Y190P; V196M; L199M; I226V; D233G | +++[1] |
| 27/28 | H40R; V43R; A64V; T71P; A80T; V87L; A94G; S96V; E145L; F147Q; L153T; D173L; Y190P; V196M; L199M; I226V; | +++[2] |
| 29/30 | E29T; H40R; V43R; A64V; T71P; T76A; A80T; V87L; A94G; V95Y; S96V; E145L; F147Q; T152L; L153T; N157C; D173L; Y190P; V196M; L199M; E200P; I226V | +++[3] |
| 31/32 | E29T; H40R; V43R; A64V; T71P; A80T; V87L; A94G; V95Y; S96R; N131C; E145L; F147Q; T152A; L153T; D173L; Y190P; V196M; L199M; I226V | +++[3] |
| 33/34 | E29T; H40R; A64V; T71P; A80T; V87L; A94G; V95Y; S96R; N131C; E145L; F147Q; T152A; L153T; D173L; Y190P; V196M; L199M; E200P; I226V | ++++[3] |
| 35/36 | L17H; D25T; E29T; H40R; A64V; T71G; A80T; V87L; A94G; V95Y; S96R; N131C; E145L; F147Q; T152A; L153T; N157S; D173L; Y190P; V196M; L199M; E200P; I226V | ++++[3] |
| 37/38 | L17H; E29T; H40R; A64V; T71P; A80T; V87L; A94G; V95Y; S96R; N131C; E145L; F147Q; T152A; L153T; N157S; D173L; Y190P; V196M; L199M; E200P; I226V | ++++[3] |

[1]Substrate: 5 g/L; DMSO: 5% (v/v); Polypeptide: 10 µL; IPA: 70% (v/v); buffer: 20% (v/v) of 0.1M TEA-HCl with 1 mM MgSO$_4$ (pH 9.0); plates heat sealed and shaken (570-575 rpm) overnight at 40° C.
[2]Substrate: 100 g/L; no DMSO added; Polypeptide: 10 µL; IPA: 70% (v/v); buffer: 25% (v/v) of 0.1M TEA-HCl with 1 mM MgSO$_4$ (pH 9.0); plates heat sealed and shaken (575 rpm) overnight at 50° C.
[3]Substrate: 100 g/L; no DMSO added; Polypeptide: 10 µL; IPA: 70% (v/v); buffer: 24% (v/v) of 0.1M TEA-HCl with 1 mM MgSO$_4$ (pH 9.0); plates heat sealed and shaken (575 rpm) overnight at 57° C.

Additional information on the functional role of residue positions of the *Lactobacillus* ketoreductase of SEQ ID NO:2 can be found in references US 20080318295A1; US 20090093031A1; US 20090155863A1; US 20090162909A1; US 20090191605A1; US 20100055751A1; WO/2010/025238A2; WO/2010/025287A2; US 20100062499A1; and WO 2008/151324A1.

Of particular relevance for conversion of compound (2c) or a structural analog thereof to compound (1c) or corresponding structural analog are ketoreductases with an amino acid sequence comprising one or more residue differences as compared to SEQ ID NO:2 at the following residue positions: X17, X25, X29, X40, X43, X64, X71, X76, X80, X87, X94, X95, X96, X131, X144, X145, X147, X150, X152, X153, X157, X173, X190, X194, X195, X196, X199, X200, X226, X233, and X249. The amino acid differences at these residue positions are based on locations or regions in the structure of reference polypeptide (e.g., SEQ ID NO: 2) and/or the associated functional properties as identified in the exemplary engineered ketoreductases of Table 3 above.

Further, in some embodiments, the non-naturally occurring engineered ketoreductases, in addition to converting compound (2c) to compound (1c), can also function as a secondary alcohol dehydrogenase of a co-factor recycling system, as described above, and thereby recycle the co-factor NADP+ or NAD+ to NADPH or NADH, respectively, in presence of a secondary alcohol. This property provides increases in efficiency of conversion of compound (2c) to compound (1c).

Accordingly, in some embodiments, a non-naturally occurring or engineered ketoreductase polypeptide of the present disclosure can include an amino acid substitution at a particular residue at a location in the structure of the reference polypeptide as identified in Table 2, particularly residue positions X17, X25, X29, X40, X43, X64, X71, X76, X80, X87, X94, X95, X96, X131, X144, X145, X147, X150, X152, X153, X157, X173, X190, X194, X195, X196, X199, X200, X226, X233, and X249, with exemplary substitutions at each of the relevant locations identified in Table 3.

Moreover, while the exemplary ketoreductases disclosed herein are based on the ketoreductase represented by SEQ ID NO:2 from *Lactobacillus kefir*, it is to be understood that non-naturally occurring ketoreductases can be based on the ketoreductase polypeptides from other *Lactobacillus* species, where the naturally occurring ketoreductase has at least 80%, 85%, 86%, 87%, 88%, 89%, 90%, 91%, 92%, 93%, 94%, 95%, 96%, 97%, 98%, or 99% sequence identity to the polypeptide of SEQ ID NO:2, such as the ketoreductase of *Lactobacillus brevis* (Genbank Acc. No. 1NXQ_A; GI: 30749782).

In view of the foregoing, in some embodiments, the ketoreductase capable of converting compound (2c) or a structural analog thereof to compound (1c) or corresponding structural analog in enantiomeric excess, comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide selected from SEQ ID NO:6, 8, 10, 12, 14, 16, 18, 20, 22, 24, 26, 28, 30, 32, 34, 36, and 38.

In some embodiments, the ketoreductase capable of converting compound (2c) or a structural analog thereof to compound (1c) or corresponding structural analog in enantiomeric excess, is a non-naturally occurring ketoreductase that comprises an amino acid sequence that has at least 80%, 85%, 86%, 87%, 88%, 89%, 90%, 91%, 92%, 93%, 94%, 95%, 96%, 97%, 98%, or 99% sequence identity to the reference polypeptide of SEQ ID NO: 10.

In some embodiments, the ketoreductase capable of converting compound (2c) or a structural analog thereof to compound (1c) or corresponding structural analog in enantiomeric excess, is a non-naturally occurring ketoreductase that comprises an amino acid sequence that has at least 80%, 85%, 86%, 87%, 88%, 89%, 90%, 91%, 92%, 93%, 94%, 95%, 96%, 97%, 98%, or 99% sequence identity to the reference polypeptide of SEQ ID NO: 16.

In some embodiments, the ketoreductase capable of converting compound (2c) or a structural analog thereof to compound (1c) or corresponding structural analog in enantiomeric excess, is a non-naturally occurring ketoreductase that comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide of SEQ ID NO:36. In some embodiments, the ketoreductase polypeptide comprises an amino acid sequence that has at least 93% sequence identity to SEQ ID NO: 36.

In some embodiments, the ketoreductase useful in the processes herein and having the specified sequence identity to any of the reference polypeptides, is capable of converting compound (2c) to compound (1c) with activity equal to or with at least 2-fold, at least 10-fold, at least 15-fold, at least 20-fold, at least 25-fold, at least 30-fold, or at least 35-fold or more increased activity relative to the activity of the polypeptide of SEQ ID NO: 4.

In some embodiments, the ketoreductase capable of converting compound (2c) or a structural analog thereof to compound (1c) or corresponding structural analog in enantiomeric excess and having the specified sequence identity to any of the reference polypeptides, is capable of converting compound (2c) to compound (1c) in at least 90%, 91%, 92%, 93%, 94%, 95%, 96%, 97%, 98%, or 99% enantiomeric excess.

In some embodiments, the ketoreductase capable of converting compound (2c) or a structural analog thereof to compound (1c) or corresponding structural analog in enantiomeric excess and having the specified sequence identity above to any of the reference polypeptides, has an amino acid sequence that comprises one or more of the following features: X17 is H or M; X29 is T; X40 is R; X43 is R or V; X64 is V; X71 is P or G; X80 is T; X87 is L; X94 is G; X95 is Y or M; X96 is V or R; X131 is C; X145 is L; X147 is Q or M; X152 is L or A; X153 is T; X173 is L; X190 is P; X196 is L or M; X199 is M; X200 is P and X226 is V.

In some embodiments, the present disclosure provides a non-naturally occurring polypeptide having ketoreductase activity and the specified sequence identity to any of the reference polypeptides disclosed herein, which also has one or more of the following substitutions not previously known in ketoreductase polypeptides derived from naturally occurring *Lactobacillus* ketoreductases: L17H; E29T; V43R; T71P or G; V87L; V95Y; N131C; D173L; or L199M. In particular, it was not known that non-naturally occurring polypeptides having ketoreductase activity could be derived from naturally occurring *Lactobacillus* ketoreductases while including substitutions at the following positions: T71 (or X71), V87 (X87), or N131 (X131). Accordingly, in some embodiments, the present disclosure provides a non-naturally occurring polypeptide having ketoreductase activity which comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide selected from SEQ ID NO:6, 8, 10, 12, 14, 16, 18, 20, 22, 24, 26, 28, 30, 32, 34, 36, and 38, and which further comprises an amino acid sequence that comprises one or more of the following features: X17 is H; X29 is T; X43 is R; X71 is P or G; X87 is L; X95 is Y; X131 is C; X173 is L; and X199 is M. Further, in some embodiments, the non-naturally occurring polypeptide having ketoreductase activity comprising one or more of the following features: X17 is H; X29 is T; X43 is R; X71 is P or G; X87 is L; X95 is Y; X131 is C; X173 is L; and X199 is M, also is capable of converting compound (2c) or a structural analog thereof to compound (1c) or corresponding structural analog in enantiomeric excess.

In some embodiments, the present disclosure provides a non-naturally occurring polypeptide having ketoreductase activity which comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide selected from SEQ ID NO:6, 8, 10, 12, 14, 16, 18, 20, 22, 24, 26, 28, 30, 32, 34, 36, and 38, and which further comprises an amino acid sequence that comprises an amino acid difference at one or more of the following positions: X17, X87, or X131. In some embodiments, the amino acid differences are selected from: X17 is H; X87 is L; or X131 is C. Further, in some embodiments, the non-naturally occurring polypeptide having ketoreductase activity comprising an amino acid difference at one or more of the following positions X17, X87, or X131 is capable of converting compound (2c) or a structural analog thereof to compound (1c) or corresponding structural analog in enantiomeric excess.

In some embodiments of the process, the ketoreductase capable of converting compound (2c) or a structural analog thereof to compound (1c) or corresponding structural analog in enantiomeric excess and having the specified sequence identity to any of the reference polypeptides, has an amino acid sequence that comprises one or more of the following features: X80 is T; X96 is V or R; X145 is L; X153 is T; X190 is P; X196 is L or M; and X226 is V.

In some embodiments, the amino acid sequence with one or more of the specified features at residue positions X80, X96, X145, X153, X190, X196, and X226, further comprises one or more of the following features: X17 is H or M; X29 is T; X40 is R; X43 is R or V; X64 is V; X71 is P or G; X87 is L; X94 is G; X95 is Y or M; X131 is C; X147 is Q or M; X152 is L or A; X173 is L; X199 is M; and X200 is P.

In some embodiments, any of the ketoreductase amino acid sequences above further comprises one or more of the following features: X25 is T; X76 is A; X144 is V; X150 is L; X157 is C or S; X194 is R; X233 is G; and X249 is W or F.

In another aspect, in accordance with the above, the present disclosure further relates to engineered ketoreductase polypeptides that can be used in the processes described herein and having enzymatic activity in converting compound (2c) or structural analog thereof to compound (1c) or corresponding structural analog that is equal to or at least 2-fold, at least 10-fold, at least 15-fold, at least 20-fold, at least 25-fold, at least 30-fold, or at least 35-fold or more relative to the activity of the polypeptide of SEQ ID NO: 4. In these embodiments, the ketoreductase polypeptides are also capable of producing compound (1c) in at least 90%, 91%, 92%, 93%, 94%, 95%, 96%, 97%, 98%, or 99% enantiomeric excess.

Accordingly, in some embodiments, the non-naturally occurring ketoreductase polypeptide for use in the processes disclosed herein and capable of converting compound (2c) or structural analog thereof to compound (1c) or corresponding structural analog in enantiomeric excess with activity that is equal to or with at least 2-fold, at least 10-fold, at least 15-fold, at least 20-fold, at least 25-fold, at least 30-fold, or at least 35-fold or more activity of the polypeptide of SEQ ID NO:4 comprises an amino acid sequence that has at least 80%, 85%, 86%, 87%, 88%, 89%, 90%, 91%, 92%, 93%, 94%, 95%, 96%, 97%, 98%, or 99% identity to a reference amino acid sequence selected from any one of SEQ ID NO: 4, 6, 8, 10, 12, 14, 16, 18, 20, 22, 24, 26, 28, 30, 32, 34, 36, or 38, with the proviso that the amino acid sequence comprises any one of the set of residue differences as compared to SEQ ID NO: 2 contained in any one of the polypeptide sequences of SEQ ID NO:4 to SEQ ID NO:38 listed in Table 3.

In some embodiments, the non-naturally occurring ketoreductase capable of converting compound (2c) or structural analog thereof to compound (1c) or corresponding structural analog in enantiomeric excess with activity that is equal to or with at least 2-fold, at least 10-fold, at least 15-fold, at least 20-fold, at least 25-fold, at least 30-fold, or at least 35-fold or more activity of the polypeptide of SEQ ID NO:4 comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide SEQ ID NO: 10, and further comprises a set of amino acid residue differences as compared to SEQ ID NO:2 of any one of SEQ ID NO: 6, 8, 10, 12, 14, 16, 18, 20, 22, 24, 26, 28, 30, 32, 34, 36, and 38.

In some embodiments, the ketoreductase capable of converting compound (2c) or a structural analog thereof to compound (1c) or corresponding structural analog in enantiomeric excess, is a non-naturally occurring ketoreductase that comprises an amino acid sequence that has at least 80%, 85%, 86%, 87%, 88%, 89%, 90%, 91%, 92%, 93%, 94%, 95%, 96%, 97%, 98%, or 99% sequence identity to the reference polypeptide SEQ ID NO: 16, and further comprises a set of amino acid residue differences as compared to SEQ ID NO:2 of any one of SEQ ID NO: 6, 8, 10, 12, 14, 16, 18, 20, 22, 24, 26, 28, 30, 32, 34, 36, and 38.

In some embodiments, the ketoreductase capable of converting compound (2c) or a structural analog thereof to compound (1c) or corresponding structural analog in enantiomeric excess, is a non-naturally occurring ketoreductase that comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide of SEQ ID NO: 36 and further comprises a set of amino acid residue differences as compared to SEQ ID NO:2 of any one of SEQ ID NO: 6, 8, 10, 12, 14, 16, 18, 20, 22, 24, 26, 28, 30, 32, 34, 36, and 38. In some embodiments, the ketoreductase polypeptide comprises an amino acid sequence that has at least 93% sequence identity to SEQ ID NO: 36, and further comprises a set of amino acid residue differences as compared to SEQ ID NO:2 of any one of SEQ ID NO: 6, 8, 10, 12, 14, 16, 18, 20, 22, 24, 26, 28, 30, 32, 34, 36, and 38.

In some embodiments, in addition to the set of amino acid residue differences of any one of the non-naturally occurring polypeptides of SEQ ID NO: 4 through SEQ ID NO: 38 in the embodiments above, the sequence of the non-naturally occurring polypeptide can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40 residue differences at other amino acid residue positions as compared to the SEQ ID NO: 2. In some embodiments, the residue differences can comprise conservative substitutions and non-conservative substitutions as compared to SEQ ID NO: 2.

In some embodiments, the ketoreductase capable of converting compound (2c) or structural analog thereof to compound (1c) or corresponding structural analog in enantiomeric excess and having the specified sequence identity to any of the reference polypeptides described herein, has an amino acid sequence that comprises at least the following features: X80 is T; X96 is V or R; X145 is L; X153 is T; X190 is P; X196 is L or M; and X226 is V.

In some embodiments, the ketoreductase amino acid sequence with the specified features at residue positions X80, X96, X145, X153, X190, X196, and X226, further comprises one or more of the following features: X71 is P or G; X87 is L; and X131 is C.

In some embodiments, the ketoreductase amino acid sequence with the specified features at residue positions X80, X96, X145, X153, X190, X196, and X226, and X71, X87, and X131 above can further comprise one or more of the following features: X17 is H or M; X29 is T; X40 is R; X43 is R or V; X64 is V; X94 is G; X95 is Y or M; X147 is Q or M; X152 is L or A; X173 is L; X199 is M; and X200 is P.

In some embodiments, the ketoreductase amino acid sequence with the specified features at the residue positions indicated above can further comprise one or more of the following features: X25 is T; X76 is A; X144 is V; X150 is L; X157 is C or S;
X194 is R; X233 is G; and X249 is W or F.

In some embodiments, the ketoreductase capable of converting compound (2c) or structural analog to compound (1c) or corresponding structural analog in enantiomeric excess and having the specified sequence identity to any of the reference polypeptides, has an amino acid sequence that comprises at least the following features: X64 is V; X71 is P; X80 is T; X87 is L; X94 is A or G; X96 is V; X145 is L; X147 is Q or M; X153 is T; X173 is L; X190 is P; X196 is M; X199 is M; and X226 is V.

In some embodiments, the ketoreductase amino acid sequence with the specified features at residue positions X64, X71, X80, X87, X94, X96, X145, X147, X153, X173, X190, X196, X199 and X226, further comprises one or more of the following features: X17 is M or H; X29 is T; X40 is R; X43 is R or V; X95 is M or Y; X131 is C; X152 is L or A; and X200 is P.

In some embodiments, the ketoreductase amino acid sequence with the specified features at the residue positions indicated above can further comprise one or more of the following features: X25 is T; X76 is A; X144 is V; X150 is L; X157 is C or S; X194 is R; X233 is G; and X249 is W or F.

In some embodiments, the ketoreductase capable of converting compound (2c) or structural analog to compound (1c) or corresponding structural analog in enantiomeric excess and having the specified sequence identity to any of the reference polypeptides, has an amino acid sequence that comprises at least the following features: X17 is H or M; X25 is T; X29 is T; X40 is R; X43 is R or V; X64 is V; X71 is G or P; X80 is T; X87 is L; X94 is G; X95 is Y or M; X96 is R or V; X131 is C; X145 is L; X147 is Q or M; X152 is A or L; X153 is T; X157 is S or C; X173 is L; X190 is P; X196 is M or L; X199 is M; X200 is P; and X226 is V.

In some embodiments, the ketoreductase with the preceding specified features can further comprise one or more of the following features: X76 is A; X144 is V; X150 is L; X194 is R; X233 is G; and X249 is W or F.

In some embodiments, the non-naturally occurring ketoreductase polypeptides capable of converting compound (2c) or structural analog thereof to compound (1c) or corresponding structural analog, comprises an amino acid sequence selected from SEQ ID NO: 6, 8, 10, 12, 14, 16, 18, 20, 22, 24, 26, 28, 30, 32, 34, 36, and 38.

In a further aspect, engineered ketoreductase polypeptides of more general applicability to conversion of protostereomeric ketones to the corresponding chiral alcohols can be made in view of the structure-function information provided herein. In some embodiments, the polypeptides useful for conversion of a ketone to a corresponding alcohol comprises an amino acid sequence having residue differences as compared to SEQ ID NO:2 at one or more residue positions selected from X71, X87 and X131, where the polypeptide has ketoreductase activity. The structure-function information indicates that residues X71 and X131 occupy the surface of the enzyme while residue X87 is at the interface between the subunits of the tetrameric enzyme. Residues changes as compared to the wild-type sequence of SEQ ID NO:2 at the specified positions affects solvent stability and/or thermostability, indicating general application to other engineered ketoreductases.

Accordingly, in some embodiments, an engineered ketoreductase polypeptide comprises an amino acid sequence that has at least 80%, 80%, 85%, 86%, 87%, 88%, 89%, 90%, 91%, 92%, 93%, 94%, 95%, 96%, 97%, 98%, or 99% sequence identity to the reference polypeptide of SEQ ID NO:2 and comprises at least one or more residue differences as compared to SEQ ID NO:2 at residue positions X71, X87 and X131, wherein the polypeptide has ketoreductase activity.

In some embodiments, an engineered ketoreductase polypeptide comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide selected from SEQ ID NO:6, 8, 10, 12, 14, 16, 18, 20, 22, 24, 26, 28, 30, 32, 34, 36, and 38 and comprises at least one or more residue differences as compared to SEQ ID NO:2 at residue positions X71, X87 and X131, wherein the polypeptide has ketoreductase activity.

In some embodiments, the engineered ketoreductase polypeptide comprises an amino acid sequence having any of the specified percent identity described above and comprising one or more of the following features: X71 is P or G; X87 is L; and X131 is C.

As will be apparent to the skilled artisan, the residues differences at residue positions X71, X87, and X131 can be combined with other residue changes that affect various enzyme properties, including among others, enzyme activity, stereoselectivity, thermostability, solvent stability, polypeptide expression, co-factor affinity, or various combinations thereof. These residue differences include those described in the present disclosure (i.e., X17, X25, X29, X40, X43, X64, X71, X76, X80, X87, X94, X95, X96, X131, X144, X145, X147, X150, X152, X153, X157, X173, X190, X194, X195, X196, X199, X200, X226, X233, and X249) and those described in references disclosing engineered variants of SEQ ID NO:2, including features disclosed in references 20080318295A1; US 20090093031A1; US 20090155863A1; US 20090162909A1; US 20090191605A1; US 20100055751A1; WO/2010/025238A2; WO/2010/025287A2; and US 20100062499A1, all of which are incorporated herein by reference.

In some embodiments, the polypeptides can comprise deletions of the engineered ketoreductase polypeptides described herein. Thus, for each and every embodiment of the polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids of the polypeptides, as long as the functional activity of the polypeptide is present, particularly with respect to the conversion of compound (2c) to compound (1c). In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, or 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35, or 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

In some embodiments, the polypeptides can comprise fragments of the engineered polypeptides described herein. In some embodiments, the fragments can have about 80%, 90%, 95%, 98%, and 99% of the full-length polypeptide, e.g., the polypeptide of SEQ ID NO:4, as long as the functional activity of the polypeptide with respect to the conversion of compound (2c) to compound (1c) is present.

In some embodiments, the polypeptides of the disclosure can be in the form of fusion polypeptides in which the engineered polypeptides are fused to other polypeptides, such as, by way of example and not limitation, antibody tags (e.g., myc epitope), purifications sequences (e.g., His tags for binding to metals), and cell localization signals (e.g., secretion signals). Thus, the engineered polypeptides described herein can be used with or without fusions to other polypeptides.

As will be understood by the skilled artisan, the polypeptides described herein are not restricted to the genetically encoded amino acids. In addition to the genetically encoded amino acids, the polypeptides may be comprised, either in whole or in part, of naturally-occurring and/or synthetic non-encoded amino acids. Certain commonly encountered non-encoded amino acids of which the polypeptides described herein may be comprised include, but are not limited to: the D-enantiomers of the genetically-encoded amino acids; 2,3-diaminopropionic acid (Dpr); α-aminoisobutyric acid (Aib); ε-aminohexanoic acid (Aha);

δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Oct); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Oct); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered ketoreductase polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having ketoreductase activity of the present disclosure can be immobilized on a solid support such that they retain their improved activity, stereoselectivity, and/or other improved properties relative to the reference polypeptide of SEQ ID NO: 4. In such embodiments, the immobilized polypeptides can facilitate the biocatalytic conversion of the substrate of compound (2c) or structural analogs thereof to the product of compound (1c) or corresponding structural analogs (e.g., as shown in the process of Scheme 1 described herein), and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the engineered ketoreductase polypeptides of the present disclosure can be carried out using the same engineered ketoreductase polypeptides bound or immobilized on a solid support.

Methods of enzyme immobilization are well-known in the art. The engineered ketoreductase polypeptide can be bound non-covalently or covalently. Various methods for conjugation and immobilization of enzymes to solid supports (e.g., resins, membranes, beads, glass, etc.) are well known in the art and described in e.g.: Yi et al., "Covalent immobilization of ω-transaminase from *Vibrio fluvialis* JS17 on chitosan beads," *Process Biochemistry* 42(5): 895-898 (May 2007); Martin et al., "Characterization of free and immobilized (5)-aminotransferase for acetophenone production," *Applied Microbiology and Biotechnology* 76(4): 843-851 (September 2007); Koszelewski et al., "Immobilization of ω-transaminases by encapsulation in a sol-gel/celite matrix," *Journal of Molecular Catalysis B: Enzymatic*, 63: 39-44 (April 2010); Truppo et al., "Development of an Improved Immobilized CAL-B for the Enzymatic Resolution of a Key Intermediate to Odanacatib," *Organic Process Research & Development*, published online: dx.doi.org/10.1021/op200157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," *Biotechnology Progress* 18(3):629-34 (2002); and Bioconjugation Protocols: Strategies and Methods, In Methods in Molecular Biology, C. M. Niemeyer ed., Humana Press (2004); the disclosures of each which are incorporated by reference herein. Solid supports useful for immobilizing the engineered ketoreductases of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered ketoreductases of the present disclosure include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the engineered ketoreductase polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the polypeptide described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the polypeptides can be provided on a substrate. In some embodiments, the polypeptides can be provided in the form of an array in which the polypeptides are arranged in positionally distinct locations. The array can be used to test a variety of aryl alkyl sulfides for conversion by the polypeptides. "Substrate," "support," "solid support," "solid carrier," or "resin" in the context of arrays refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

In some embodiments, the kits of the present disclosure include arrays comprising a plurality of different engineered ketoreductase polypeptides at different addressable position, wherein the different polypeptides are different variants of a reference sequence each having at least one different improved enzyme property. Such arrays comprising a plurality of engineered polypeptides and methods of their use are described in, e.g., WO2009/008908A2.

6.3 Ketoreductase Encoding Polynucleotides, Expression Vectors and Host Cells In another aspect, the present disclosure provides polynucleotides encoding the non-naturally occurring polypeptides described herein. These polynucleotides may be operatively linked to one or more heterologous regulatory sequences that control gene expression to create a recombinant polynucleotide capable of expressing the ketoreductase polypeptide. Expression constructs containing a heterologous polynucleotide encoding the engineered ketoreductase polypeptide can be introduced into appropriate host cells to express the corresponding polypeptide.

Because of the knowledge of the codons corresponding to the various amino acids, availability of a protein sequence provides a description of all the polynucleotides capable of encoding the subject. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide described herein, including the amino acid sequences presented in Table 3.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the ketoreductases (e.g., because the natural sequence can have preferred codons and because use of preferred codons may not be required for all amino acid residues), codon optimized polynucleotides encoding the ketoreductase polypeptides may contain preferred codons at about 40%, 50%, 60%, 70%, 80%, or greater than 90% of codon positions of the full length coding region.

In some embodiments, the polynucleotide encodes a non-naturally occurring polypeptide capable of converting compound (2c) or a structural analog thereof to compound (1c) or corresponding structural analog in enantiomeric excess, where the polypeptide comprises an amino acid sequence having at least 80%, 85%, 86%, 87%, 88%, 89%, 90%, 91%, 92%, 93%, 94%, 95%, 96%, 97%, 98%, or 99% identity to a reference polypeptide selected from any one of SEQ ID NO: 4, 6, 8, 10, 12, 14, 16, 18, 20, 22, 24, 26, 28, 30, 32, 34, 36, and 38.

In some embodiments, the polynucleotide encodes a non-naturally occurring ketoreductase polypeptide capable of converting compound (2c) or a structural analog thereof to compound (1c) or corresponding structural analog in enantiomeric excess, wherein the ketoreductase polypeptide comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide SEQ ID NO: 10.

In some embodiments, the polynucleotide encodes a non-naturally occurring ketoreductase polypeptide capable of converting compound (2c) or a structural analog thereof to compound (1c) or corresponding structural analog in enantiomeric excess, wherein the ketoreductase polypeptide comprises an amino acid sequence that has at least 80%, 85%, 86%, 87%, 88%, 89%, 90%, 91%, 92%, 93%, 94%, 95%, 96%, 97%, 98%, or 99% sequence identity to the reference polypeptide of SEQ ID NO: 16.

In some embodiments, the polynucleotide encodes a non-naturally occurring ketoreductase polypeptide capable of converting compound (2c) or a structural analog thereof to compound (1c) or corresponding structural analog in enantiomeric excess, wherein the ketoreductase polypeptide comprises an amino acid sequence that has at least 80%, 85%, 86%, 87%, 88%, 89%, 90%, 91%, 92%, 93%, 94%, 95%, 96%, 97%, 98%, or 99% sequence identity to a reference polypeptide of SEQ ID NO: 36. In some embodiments, the polynucleotide encodes a ketoreductase polypeptide comprising an amino acid sequence that has at least 93% sequence identity to SEQ ID NO: 36.

In some embodiments, the polynucleotide encodes a non-naturally occurring polypeptide capable of converting compound (2c) to compound (1c) with activity equal to or at least 2-fold, at least 10-fold, at least 15-fold, at least 20-fold, at least 25-fold, at least 30-fold, or at least 35-fold increased relative to the activity of the polypeptide of SEQ ID NO: 4, wherein the polypeptide comprises an amino acid sequence having at least 80%, 85%, 86%, 87%, 88%, 89%, 90%, 91%, 92%, 93%, 94%, 95%, 96%, 97%, 98%, or 99% identity to a reference polypeptide selected from any one of SEQ ID NO: 4, 6, 8, 10, 12, 14, 16, 18, 20, 22, 24, 26, 28, 30, 32, 34, 36, or 38, with the proviso that the amino acid sequence comprises any one of the set of residue differences as compared to SEQ ID NO: 2 contained in any one of the polypeptide sequences of SEQ ID NO: 4 to SEQ ID NO: 38 listed in Table 3. As discussed herein, in some embodiments, the reference polypeptide is SEQ ID NO: 10, 16 or 36.

In some embodiments, the polynucleotide encodes a non-naturally occurring, engineered ketoreductase polypeptide capable of converting compound (2c) or a structural analog thereof to compound (1c) or corresponding structural analog in enantiomeric excess, and having any of the specified sequence identity to any of the reference polypeptides described herein, and comprises one or more residue differences as compared to SEQ ID NO:2 at the following residue positions: X17, X25, X29, X40, X43, X64, X71, X76, X80, X87, X94, X95, X96, X131, X144, X145, X147, X150, X152, X153, X157, X173, X190, X194, X195, X196, X199, X200, X226, X233, and X249. As such, in some embodiments, the polynucleotides encode the ketoreductase polypeptides having any of the specified sequence identity to the reference polypeptides described above and comprising the specified features at the foregoing residue positions, including sets of residue positions, as provided in the present disclosure.

In some embodiments, the polynucleotides encoding the polypeptides are selected from SEQ ID NO: 3, 5, 7, 9, 11, 13, 15, 17, 19, 21, 23, 25, 27, 29, 31, 33, 35, and 37.

In some embodiments, the polynucleotides are capable of hybridizing under highly stringent conditions to a polynucleotide comprising SEQ ID NO: 3, 5, 7, 9, 11, 13, 15, 17, 19, 21, 23, 25, 27, 29, 31, 33, 35, or 37, or a complement thereof, where the highly stringently hybridizing polynucleotides encode a non-naturally occurring polypeptide capable of converting compound (2c) to compound (1c) with activity equal to or with at least 2-fold, at least 10-fold, at least 15-fold, at least 20-fold, at least 25-fold, at least 30-fold, or at least 35-fold increased activity relative to the activity of the polypeptide of SEQ ID NO: 4.

In some embodiments, the polynucleotides encode the polypeptides described herein but have about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase polypeptides described herein. In some embodiments, the reference polynucleotide is selected from SEQ ID NO: 3, 5, 7, 9, 11, 13, 15, 17, 19, 21, 23, 25, 27, 29, 31, 33, 35, and 37.

An isolated polynucleotide encoding a non-naturally occurring polypeptide of the present disclosure may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2006.

In some embodiments, the control sequences include among others, promoters, leader sequence, polyadenylation sequence, propeptide sequence, signal peptide sequence, and transcription terminator. Suitable promoters can be selected based on the host cells used. Exemplary bacterial promoters include *E. coli* lac operon, *E. coli* trp operon, bacteriophage □, *Streptomyces coelicolor* agarase gene (dagA), *Bacillus subtilis* levansucrase gene (sacB), *Bacillus licheniformis* alpha-amylase gene (amyL), beta-lactamase gene, and tac promoter; exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease, and mutant, truncated, and hybrid promoters thereof, and exemplary yeast cell promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase.

In some embodiments, the control sequence may also be a signal peptide coding region that codes for an amino acid sequence linked to the amino terminus of a polypeptide and directs the encoded polypeptide into the cell's secretory pathway. The signal sequence typically depends on the type of host cells being used to express the polypeptide. Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Exemplary signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase.

Other control sequences, such as leader sequences, polyadenylation sequences, and transcription terminator sequences can use those available in the art (see Sambrook, supra, and Current Protocols in Molecular Biology, supra).

In another aspect, the present disclosure is also directed to a recombinant expression vector comprising a polynucleotide encoding an engineered ketoreductase polypeptide, and one or more expression regulating regions such as a promoter and a terminator, a replication origin, etc., depending on the type of hosts into which they are to be introduced. The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The expression vector preferably contains one or more selectable markers, which permit easy selection of transformed cells. A selectable marker is a gene the product of which provides for biocide or viral resistance, resistance to heavy metals, prototrophy to auxotrophs, resistance to chemical agents (e.g., antibiotics) and the like.

In another aspect, the present disclosure provides a host cell comprising a polynucleotide encoding an engineered ketoreductase polypeptide of the present disclosure, the polynucleotide being operatively linked to one or more control sequences for expression of the ketoreductase polypeptide in the host cell. Host cells for use in expressing the ketoreductase polypeptides encoded by the expression vectors of the present invention are well known in the art and include but are not limited to, bacterial cells, such as *E. coli, Lactobacillus, Streptomyces* and *Salmonella typhimurium* cells; fungal cells, such as yeast cells; insect cells such as *Drosophila* S2 and *Spodoptera* Sf9 cells; animal cells such as CHO, COS, BHK, 293, and Bowes melanoma cells; and plant cells. Exemplary host cells are *Escherichia coli* BL21 and W3110.

Appropriate culture mediums and growth conditions for the above-described host cells are well known in the art. Polynucleotides for expression of the ketoreductase may be introduced into host cells by various methods known in the art (e.g., electroporation, biolistic particle bombardment, liposome mediated transfection, calcium chloride transfection, and protoplast fusion).

In the embodiments herein, the non-naturally occurring or engineered ketoreductase polypeptides and nucleotides encoding such polypeptides can be prepared using methods commonly used by those skilled in the art. As noted above, the naturally-occurring amino acid sequence and corresponding polynucleotide encoding the ketoreductase enzyme of *Lactobacillus kefir* for use in generating engineered ketoreductases are available as Genbank Acc. No. AAP94029.1; GI: 33112056. In some embodiments, the parent polynucleotide sequence is codon optimized to enhance expression of the ketoreductase in a specified host cell.

The engineered ketoreductase polypeptides can be obtained by subjecting the polynucleotide encoding the naturally occurring ketoreductase to mutagenesis and/or directed evolution methods (see, e.g., Stemmer, 1994, Proc Natl Acad Sci USA 91:10747-10751; PCT Publ. Nos. WO 95/22625, WO 97/0078, WO 97/35966, WO 98/27230, WO 00/42651, and WO 01/75767; U.S. Pat. Nos. 6,537,746; 6,117,679; 6,376,246; and 6,586,182; and U.S. Pat. Publ. Nos. 20080220990A1 and 20090312196A1; each of which is hereby incorporated by reference herein).

Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, Methods Mol. Biol. 57:369-74; Smith, 1985, Ann. Rev. Genet. 19:423-462; Botstein et al., 1985, Science 229:1193-1201; Carter, 1986, "Site-directed mutagenesis," Biochem. J. 237:1-7; Kramer et al., 1984, Cell 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; and Stemmer, 1994, Nature 370:389-391. All publications are incorporated herein by reference.

In some embodiments, the clones obtained following mutagenesis treatment are screened for non-naturally occurring ketoreductases having a desired enzyme property. Measuring ketoreductase enzyme activity from the expression libraries can be performed using standard techniques, such as separation of the product (e.g., by HPLC or GC) and detection of the product by measuring UV absorbance of the separated substrate and products and/or by detection using tandem mass spectroscopy (e.g., MS/MS). Clones containing a polynucleotide encoding the desired engineered polypeptides are then isolated, sequenced to identify the nucleotide sequence changes (if any), and used to express the enzyme in a host cell. Exemplary assays are provided below in Example 3.

Where the sequence of the polypeptide is known, the polynucleotides encoding the enzyme can be prepared by standard solid-phase methods, according to known synthetic methods, e.g., the classical phosphoramidite method described by Beaucage et al., 1981, Tet Lett 22:1859-69, or the method described by Matthes et al., 1984, EMBO J. 3:801-05. In some embodiments, fragments of up to about 100 bases can be individually synthesized, then joined (e.g., by enzymatic or chemical litigation methods, or polymerase mediated methods) to form any desired continuous sequence.

In some embodiments, the present disclosure also provides methods for preparing or manufacturing the non-naturally occurring polypeptides capable of converting compound (2c) to compound (1c), wherein the methods comprise culturing a host cell capable of expressing a polynucleotide encoding the non-naturally occurring polypeptide under conditions suitable for expression of the polypeptide. In some embodiments, the method for preparing or manufacturing the non-naturally occurring ketoreductase polypeptide further comprises the step of isolating the polypeptide from the host cell. The non-naturally occurring polypeptides can be expressed in appropriate cells, as described above, and isolated (or recovered) from the host cells and/or the culture medium using any one or more of the well known techniques used for protein purification, including, among others, lysozyme treatment, sonication, filtration, salting-out, ultra-centrifugation, and chromatography.

Chromatographic techniques for isolation of the ketoreductase polypeptide include, among others, reverse phase chromatography high performance liquid chromatography, ion exchange chromatography, gel electrophoresis, and affinity chromatography.

In some embodiments, the non-naturally occurring polypeptide of the disclosure can be prepared and used in various isolated forms including but not limited to crude extracts (e.g., cell-free lysates), powders (e.g., shake-flask powders), lyophilizates, and substantially pure preparations (e.g., DSP powders), as further illustrated in the Examples below.

In some embodiments, the non-naturally occurring polypeptide of the disclosure can be prepared and used in purified form. Generally, conditions for purifying a particular enzyme will depend, in part, on factors such as net charge, hydrophobicity, hydrophilicity, molecular weight, molecular shape, etc., and will be apparent to those having skill in the art. To facilitate purification, it is contemplated that in some embodiments the engineered ketoreductase polypeptides of the present disclosure can be expressed as fusion proteins with purification tags, such as His-tags having affinity for metals, or antibody tags for binding to antibodies, e.g., myc epitope tag.

7. EXAMPLES

Various features and embodiments of the disclosure are illustrated in the following representative examples, which are intended to be illustrative, and not limiting.

Example 1

Wild-Type Ketoreductase Gene Acquisition and Construction of Expression Vectors

The wild-type ketoreductase gene from *L. kefir* (SEQ ID NO: 1) was designed for expression in *E. coli* using standard codon optimization. (Codon-optimization software is reviewed in e.g., "OPTIMIZER: a web server for optimizing the codon usage of DNA sequences," Puigbò et al., Nucleic Acids Res. 2007 July; 35(Web Server issue): W126-31. Epub 2007 Apr. 16.) Genes were synthesized using oligonucleotides composed of 42 nucleotides and cloned into expression vector pCK110900 (vector depicted as FIG. 3 in US Patent Application Publication 20060195947, which is hereby incorporated by reference herein) under the control of a lac promoter. The expression vector also contained the P15a origin of replication and the chloramphenicol resistance gene. Resulting plasmids were transformed into *E. coli* W3110 (fhu−) using standard methods. Polynucleotides encoding the engineered ketoreductase polypeptides were also cloned into vector pCK110900 for expression in *E. coli* W3110.

The engineered ketoreductase polypeptide of SEQ ID NO: 4 was obtained by directed evolution of a codon-optimized gene encoding the wild-type ketoreductase of *Lactobacillus kefir* (Genbank acc. No. AAP94029.1; GI: 33112056). SEQ ID NO: 4 has 9 amino acid residue differences relative to the WT ketoreductase (A80T, A94G, S96V, E145L, L153T, Y190P, V196L, I226V, and Y249W) of SEQ ID NO:2. The polypeptide of SEQ ID NO: 4 was found to be able to convert compound (2c) to compound (1c) in >99% e.e. and with about 25% conversion rate in 24 h under initial screening conditions (100 g/L compound (2a) substrate; 0.5 g/L NADP, 100 mM TEA, pH 9.0, 1 mM MgSO$_4$, 40° C.). The polypeptide SEQ ID NO: 4 was used as the starting backbone for subsequent rounds of evolution. Multiple rounds of directed evolution of the gene encoding SEQ ID NO: 4 (i.e., SEQ ID NO: 3) were carried out. Each round used the gene encoding the most improved engineered polypeptide from each round as the parent "backbone" sequence for the subsequent round of evolution. The resulting engineered ketoreductase polypeptide sequences and specific mutations and relative activities are listed in Table 3.

Example 2

Production of Engineered Polypeptides

The engineered ketoreductase polypeptides of the disclosure were produced in *E. coli* W3110 as an intracellular protein expressed under the control of the lac promoter. The polypeptide accumulates primarily as a soluble cytosolic active enzyme. A shake-flask procedure is used to generate engineered polypeptide powders that can be used in activity assays or biocatalytic process disclosed herein.

Fermentation for Shake Flask Powders.

A single microbial colony of *E. coli* containing a plasmid encoding an engineered ketoreductase of interest is inoculated into 50 mL Luria Bertani broth containing 30 µg/ml chloramphenicol and 1% glucose. Cells are grown overnight (at least 16 hours) in an incubator at 30° C. with shaking at 250 rpm. The culture is diluted into 250 mL Terrific Broth (12 g/L bacto-tryptone, 24 g/L yeast extract, 4 mL/L glycerol, 65 mM potassium phosphate, pH 7.0, 1 mM MgSO$_4$) containing 30 µg/ml chloramphenicol, in a 1 liter flask to an optical density at 600 nm (OD600) of 0.2 and allowed to grow at 30° C. Expression of the ketoreductase gene is induced by addition of isopropyl-β-D-thiogalactoside ("IPTG") to a final concentration of 1 mM when the OD600 of the culture is 0.6 to 0.8. Incubation is then continued overnight (at least 16 hours). Cells are harvested by centrifugation (5000 rpm, 15 min, 4° C.) and the supernatant discarded.

Production of Ketoreductase Shake-Flask Powders:

The cell pellet is resuspended with an equal volume of cold (4° C.) 100 mM phosphate buffer, pH 9.0 (optionally including 2 mM MgSO$_4$), and harvested by centrifugation as above. The washed cells are resuspended in two volumes of the cold phosphate buffer and passed through a French Press twice at 12,000 psi while maintained at 4° C. Cell debris is removed by centrifugation (9000 rpm, 45 minutes, 4° C.). The clear lysate supernatant was collected and stored at −20° C. Lyophilization of frozen clear lysate provides a dry shake-flask powder of crude ketoreductase polypeptide. Alternatively, the cell pellet (before or after washing) can be stored at 4° C. or −80° C.

Fermentation for Production Downstream Process (DSP) Powders.

Larger-scale (~100-120 g) fermentation of the engineered ketoreductases for production of DSP powders can be carried out as a short batch followed by a fed batch process according to standard bioprocess methods. Briefly, ketoreductase expression is induced by addition of IPTG to a final concentration of 1 mM. Following fermentation, the cells are harvested and resuspended in 100 mM triethanolamine-H$_2$SO$_4$ buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 3

High Throughput (HTP) Assay Protocols

High-Throughput Growth & Expression.

Cells were picked and grown using standard KRED protocol for W3110 with direct induction: (1) Master growth=single colonies picked from agar Q-trays by Q-bot and grown overnight in LB media containing 1% glucose and 30 μg/mL chloramphenicol (CAM), 30° C., 200 rpm, 85% humidity. (2) Subculture=20 μL of overnight growth transferred to a deep well plate containing 380 μL 2×YT growth media containing 30 μg/mL CAM, 1 mM IPTG, 1 mM MgSO$_4$, and incubated for ~18 h at 30° C., 200 rpm, 85% humidity. Subculture TB media was made up of TB media (380 μL/well), 30 μg/mL CAM, 1 mM MgSO$_4$, and 1 mM IPTG. Cell culture was centrifuged at 4000 rpm, 4° C. for 10 min., and the media discarded. Cell pellets were resuspended in 200-400 μL lysis buffer (0.1 M triethanolamine (TEA) buffer, pH 9.0, containing 1 mM MgSO$_4$, 400 μg/mL PMBS and 500 μg/mL Lysozyme).

HTP Screening Procedure.

Standard HTP reaction assays were carried out on 200 μL reaction volume scales in 96-wells deep well plates (reaction assay blocks). The reaction mixtures in each well typically consisted of: 5.0 g/L substrate oxcarbazepine prepared in DMSO or approximately 80 g/L solid substrate oxcarbazepine; 0.05 g/L NADP$^+$; 70% isopropyl alcohol (IPA); 0, 0.5 or 1% acetone; and 10 μL, 20 μL or 50 μL of clear lysates, as further specified below. Generally, reaction reagents were added using automated HTP robotics, such as Biomek NX. Lysis volumes were fixed at 150 μL or 300 μL. In later rounds, lysates were diluted 2× or 0.6× after lysis.

Assay Protocols I and II.

Cell lysates were prepared by one of two methods. Cell pellets were lysed with 300 μL/well lysis buffer (1.0 mg/mL lysozyme, 0.5 mg/mL PMBS in 0.1M TEA-HCl with 1 mM MgSO$_4$, pH 9.0) for plates grown using TB medium as subculture media. 150 μL/well or 300 μL/well lysis buffer was used for plates grown using 2×YT medium as subculture media. Lysates were also prepared by lysing cell pellets with 300 μL/well lysis buffer for plates grown using TB medium as subculture media and then 2× diluted with 0.1M TEA-HCl with 1 mM MgSO$_4$ (pH 9.0) buffer.

Plates were then left to shake at speed of 1.5-2.5 g on a titre-plate shaker, room temperature, for 1.5 hrs. Plates containing lysed cells were centrifuged at 4000 rpm for 10 min at 4° C. Plates with lysates were stored at 4° C. if they were not immediately used.

The reaction condition comprised oxcarbazepine, 5 g/L (5% v/v DMSO); NADP$^+$, 0.05 g/L; IPA 70% v/v; and lysate, 10 μL or 20 μL. Assay was carried out by adding into reaction assay blocks 10 μL/well of 100 g/L warmed substrate in DMSO (freshly prepared), 140 μL/well of isopropyl alcohol (IPA), and 40 μL/well of 0.25 g/L NADP$^+$, prepared in 0.1M TEA-HCl with 1 mM MgSO$_4$ (pH 9.0). Clear lysates (10 μL/well) from lysate plates were transferred to their reaction mixtures. Plates were heat sealed and left to shake overnight at 40° C. and 570-575 rpm.

For reactions in which cells were lysed in 150 μL/well lysis buffer, 10 μL/well of 100 g/L warmed substrate in DMSO, freshly prepared, were added into reaction assay blocks. This was followed by the addition of 30 μL/well of 0.33 g/L NADP+ prepared in 0.1M TEA-HCl with 1 mM MgSO$_4$ (pH 9.0) followed by 140 μL/well of isopropyl alcohol (IPA). Clear lysates (20 μL/well) from lysate plates were respectively transferred to their reaction mixtures. Plates were heat sealed and left to shake overnight at 40° C. and 570 rpm.

Assay Protocol III.

Lysates were prepared as described for Assay Protocols I and II above. The reaction conditions comprised oxcarbazepine, 75 g/L; NADP$^+$, 0.05 g/L; IPA, 70% v/v; and lysate, 10 μL, 20 μL or 50 μL. Assays were carried out by dispensing 15 mg substrate solid into reaction assay blocks using solid dose template plate Millipore MACL09625. This was followed by 10 μL/well of 1 g/L NADP$^-$ prepared in 0.1M TEA-HCl with 1 mM MgSO$_4$ (pH 9.0). IPA of 140 μL/well of was then dispensed into the assay blocks. Clear lysates of 50 μL/well from lysate plates were respectively transferred to their reaction mixtures. Plates were heat sealed and left to shake overnight at 45° C. and 575 rpm.

Assay Protocol IV.

Cell pellets were lysed with 300 μL/well lysis buffer and then diluted 0.6× with 0.1M TEA-HCl with 1 mM MgSO$_4$ (pH 9.0) buffer, and worked up as described in Reactions I and II above. The reaction conditions comprised oxcarbazepine, 75 g/L; NADP$^+$ 0.05 g/L; IPA, 70% v/v; and lysate, 10 μL, 20 μL or 50 μL. Assays were carried out by dispensing 15-20 mg substrate solid into reaction assay blocks using solid dose template plate Millipore MACL09625. IPA was dispensed into the reaction assay blocks at 140 μL/well, followed by 50 μL/well of NADP 0.2 g/L prepared in 0.1M TEA-HCl with 1 mM MgSO$_4$ (pH 9.0). Clear lysates of 10 μL/well from lysate plates were respectively transferred to their reaction mixtures. Plates were heat sealed and left to shake overnight at 50° C. and 575 rpm.

Assay Protocol V.

Cell pellets were processed as described in Assay Protocol IV. The reaction condition comprised oxcarbazepine, 75 g/L; NADP$^+$ 0.05 g/L; IPA/Acetone, 70:0.5% v/v; and lysate 10 μL. Assays were carried out by dispensing 15-20 mg solid substrate into reaction assay blocks using solid dose template plate Millipore MACL09625, followed by 49 μL/well of 0.2 g/L NADP+ prepared in 0.1M TEA-HCl with 1 mM MgSO$_4$ (pH 9.0). IPA:acetone (99.3:0.7% v/v) of 141 μL/well was dispensed into reaction assay blocks containing the substrate to obtain a final concentrations of 70% IPA and 0.5% acetone in the reaction mixtures. Clear lysates of 10 μL/well from lysate plates were transferred to the reaction mixtures. Plates were heat sealed and left to shake overnight at 50° C. and 575 rpm.

Assay Protocol VI.

Cell pellets were processed as described in Assay Protocol IV. Reaction conditions comprised oxcarbazepine, 75 g/L; NADP+, 0.05 g/L; IPA, 70% v/v; and lysate, 10 μL, 20 μL or 50 μL. Assays were carried out by dispensing 15-20 mg solid substrate into reaction assay blocks using solid dose template plate Millipore MACL09625, followed by 40 μL/well of 0.25 g/L NADP+ prepared in 0.1M TEA-HCl with 1 mM MgSO$_4$ (pH 9.0). IPA of 140 μL/well was dispensed into reaction assay blocks. Clear lysates of 20 μL/well from lysate plates were transferred to the reaction mixtures. Plates were heat sealed and left to shake at 57° C. and 575 rpm for the following periods: (a) overnight, i.e., approximately 18 hrs, or (b) 4 hrs.

Assay Protocol VII.

Cell pellets were processed as described in Assay Protocol IV above. Reaction conditions comprised oxcarbazepine, 75 g/L; NADP$^+$, 0.05 g/L; IPA/Acetone, 70:1% v/v; and lysate, 10 μL. Assays were carried out by dispensing 15-20 mg solid substrate into reaction assay blocks using solid dose template plate Millipore MACL09625, followed by 48 μL/well of 0.21 g/L NADP$^+$ prepared in 0.1M TEA-HCl with 1 mM MgSO$_4$ (pH 9.0). IPA:acetone (98.6:1.4% v/v) of 142 μL/well were dispensed into reaction assay blocks containing substrate to obtain the final concentrations of 70% IPA and 1% acetone in the reaction mixtures. Clear lysates of 10 μL/well from lysate plates were respectively transferred to their reaction mixtures. Plates were heat sealed and left to shake overnight at 57° C. with a speed of 575 rpm.

Assay Protocol VIII.

Oxcarbazepine, 75 g/L; NADP+, 0.05 g/L; IPA/Acetone, 70:1% v/v; and lysate, 10 μL. Assays were carried out by dispensing 15-20 mg solid substrate into reaction assay blocks using solid dose template plate Millipore MACL09625, followed by 48 μL/well of 0.21 g/L NADP+ prepared in 0.1M TEA-HCl with 1 mM MgSO$_4$ (pH 9.0). IPA:acetone (98.6:1.4% v/v) of 142 μL/well was dispensed into reaction assay blocks containing substrate to obtain the final concentrations of 70% IPA and 1% acetone in the reaction mixtures. Clear lysates of 10 μL/well from lysate plates were transferred to their reaction mixtures. Plates were heat sealed and left to shake at 62° C. and 575 rpm for the following periods: (i) overnight i.e. approximately 18 hrs, or (ii) 6 hrs.

For reaction plates with substrate loaded as homogenous DMSO solution, after designated reaction times, plates were centrifuged at 4000 rpm for 1 min at 25° C. Acetonitrile at 800 μL/well were added into the reaction assay mixes. Plates were heat sealed and vigorously shaken for about 15 min at RT on titre-plate shaker (approximately 8 g) and visually inspected to ensure that there was no precipitation of substrates or products. Quenched plates were spun down at 4000 rpm for 10 min at 25° C.

For reaction plates with solid dosed substrate, after designated reaction times, plates were centrifuged at 4000 rpm for 1 min at 25° C. DMSO of 1200 μL/well was added into the reaction assay mixes. Plates were heat sealed and vigorously shaken for about 15 min at RT on titre-plate shaker (approximately 8 g). Plates with quenched reactions were visually inspected to ensure that all solid substrate were dissolved. When necessary, plates were shaken again for approximately 15 min until no solid substrate was observed. Quenched reactions were left to shake at 575 rpm for about 10 min at 45° C. to ensure that residual solid substrate in the mixtures was dissolved. Quenched plates were spun down at 4000 rpm for 10 min at 25° C.

HPLC Screening Assay for Reactions with Solid Dosed Substrate.

HTP reaction assays performed using substrate loaded as DMSO solution were prepared for analysis by taking 40 μL of quenched reaction mixtures and diluting with 160 μL of acetonitrile in Costar™ 96-wells round bottom plates.

HTP reaction assays performed using solid dosed substrate, i.e., high substrate loading of ~75 g/L substrate was prepared for analysis by taking 10 μL of quenched reaction mixtures and diluting with 190 μL of acetonitrile in Costar™ 96-wells round bottom plates. The samples were then analyzed by HPLC.

HPLC Protocol 1: HPLC chromatographic analysis used Agilent's Eclipse XDB C-18 column, 4.6×150 mm, 5 μm diameter column, at a temperature of 25° C., and a flowrate of 1.2 mL/min using a mobile phase of water containing 0.1% acetic acid/acetonitrile, 60/40% v/v, where the acetic acid is prepared in 18.2 MΩ cm-1 milli-Q™ water. The column detection wavelengths were 210 nm, 230 nm and 254 nm. Retention time for the ketone is ~2.1 min, and retention time for the alcohol is ~1.5 min, respectively. This protocol was primarily used for HTP screening assays in all rounds.

HPLC Protocol 2: HPLC chromatographic analysis used Agilent's Eclipse XDB C-8 column, 4.6×150 mm, 5 μm diameter column, at a temperature of 25° C. and a flowrate of 1.5 mL/min using a mobile phase of 10 mM ammonium acetate/acetonitrile, 45/55% v/v. The column detection wavelengths were 210 nm, 230 nm and 254 nm. Retention time for the ketone is ~1.3 min and retention time for the alcohol is ~1.1 min, respectively. This protocol was used for rapid screenings, e.g., in Round 1 libraries screenings.

Example 4

Biocatalytic Process I for Preparation of Compound (1c) from Compound (2c)—25 g Scale Reaction This example illustrates a first biocatalytic process using an engineered ketoreductase polypeptide of the disclosure to prepare compound (1c) on a 25 g scale. The reaction was carried out in an aqueous co-solvent system of 0.1 M TEA, 1 mM MgSO$_4$, pH 9.0, 70% IPA, and compound (2a) loading of 50 g/L. The engineered ketoreductase (SEQ ID NO:36) was at a loading of 3 g/L along with co-factor NADPH at 0.1 g/L. The engineered ketoreductase also has secondary alcohol dehydrogenase activity, acting as a recycling system with the IPA to regenerate the oxidized co-factor NADP+ to NADPH through the oxidation of the IPA to acetone. Execution of this procedure as described afforded 23.2 g (93% isolated yield) of crude desired product in one run with 96.2% chemical purity (w/w, HPLC Method 5).

Reaction Protocol.

A 1 L baffled jacketed reactor was charged sequentially with the following: 0.1 M TEA buffer solution (pH 9.0), 100 L; IPA, 350 mL; oxcarbazepine, 25 g charged as a solid. The reactor vessel was equipped with an overhead anchor stirrer. A temperature probe was inserted to check the internal solution temperature and a nitrogen inlet connected to a flow meter. An outlet tube with condenser was also attached. The reaction mixture was stirred at 45° C. (internal temperature) at 200 rpm with a nitrogen flow rate of 1 L/min for 10 min.

The reaction mixture was then charged sequentially with the following: NADP+(50 mg), 1 mL prepared in TEA buffer; ketoreductase polypeptide of SEQ ID NO: 36 (1.5 g of DSP Powder), and 10 mL prepared in TEA buffer. The reaction mixture at the start of the process is a white slurry with an initial pH of about 8. The reaction mixture was stirred at the above conditions for 24 hours. The reaction volume was maintained by the intermittent addition of deionized water (Total vol. added: 4×10 mL). After 8 hours, the nitrogen flow rate was turned off to prevent any significant overnight evaporation.

The reaction course was followed periodically by taking samples from the reaction mixture, quenching, and analyzing as described in Method 1. Samples were also frequently monitored for acetone content using the procedure described in Method 4. For the purposes of tracking the process, t=0 was set at the time at which the enzyme was added.

After in-process analyses indicated >99% conversion (24 hours), the reaction mixture was taken for subsequent workup and isolation. The solution was allowed to cool to room temperature then drained from the reactor into a 500 mL round-bottom flask. IPA was distilled by rotary evaporation (60 torr, 40° C. bath) until 5-10% IPA remained relative to the start of distillation (IPA concentration determined by Method 4).

The crude product was collected by filtration through a sintered funnel and washed with 20 mL of heptane. The solid was dried for 24 h under vacuum (3-20 mm Hg) at 30° C. Upon drying, 23.2 g (93% yield) of crude product was obtained with a chemical purity of 96.2% (as determined by HPLC Method 5) and >99.9% e.e (as determined by HPLC Method 3). The residual protein content in the crude isolated product measured 0.87% by weight. The level of residual protein was measured using a UV absorbance-based protein quantification assay (SPN™-Assay) commercially available from G-Biosciences (Maryland Heights, Mo., USA).

Analytical Methods for Example 3.

Five different methods were used for determining % conversion, purity of compound (1a), enantiomeric purity, IPA and acetone concentration, and % potency.

Method 1—In-Process % Conversion.

To prepare a sample for HPLC analysis, 100 μL of reaction mixture was quenched with 900 μL 1:1 DMSO:MeCN. The sample was centrifuged to remove precipitated enzyme. 10 μL of supernatant was added to 990 μL MeCN and used for chromatographic analysis.

Method 1 Chromatographic Parameters

| | |
|---|---|
| Instrument | Agilent 1200 HPLC system |
| Column | Agilent Eclipse XDB C18 4.6 × 150 mm, 5 μm |
| Mobile Phase | MeCN/0.1% HOAc in water (40/60) |
| Column temperature | 25° C. |
| Flow rate | 1.2 mL/min |
| Injection volume | 10 μL |
| UV Wavelength | 210 nm |
| Runtime | 3.2 min |
| Product | 1.8 min |
| Substrate | 2.5 min |
| Linearity | 0.99 ($R^2$ at 2-200 ppm substrate and product) |
| RF (Product to substrate) | 1.23 |

The percent (%) conversion was calculated as follows:

$$\% \text{ Conversion} = \frac{[\text{Peak Area of product}]}{[\text{Peak Area of product}] + [\text{Peak Area of substrate} * RF]} * 100\%$$

Method 2—Identification and Impurity Determination by HPLC.

20.0 mg of isolated eslicarbazepine was weighed into 100 mL volumetric flask and dissolved in approximately 80 mL in MeCN. The mixture was sonicated for 5 min and brought up to the final volume with MeCN.

Method 2 Chromatographic Parameters

| | | | |
|---|---|---|---|
| Instrument | Agilent 1200 HPLC system | | |
| Column | Agilent Eclipse XDB C18 4.6 × 150 mm, 5 μm | | |
| Mobile Phase (Premixed) | Gradient | | |
| | Eluent A: MeCN | | |
| | Eluent B: 0.1% HOAc in water | | |
| | Time (min) | Eluent A (%) | Eluent B (%) |
| | 0 | 20 | 80 |
| | 12 | 30 | 70 |
| | 18 | 50 | 50 |
| | 20 | 50 | 50 |
| | 22 | 20 | 80 |
| Detection Wavelength | 230 nm | | |
| Column Temperature | 25° C. | | |
| Injection Volume | 10 μL | | |
| Run time | 22 min (Post Time 8 min) | | |
| Product | 6.2 min | | |
| Substrate | 10.7 min | | |
| Flow rate | 1 mL/min | | |

Method 3—Enantiomeric Purity of (S)-Licarbazepine.

Samples were prepared by taking 40.0 mg of isolated (S)-licarbazepine weighed into a 100 mL volumetric flask and dissolving in 80 mL of MeCN. The mixture was sonicated for 5 min and brought up to the final volume with MeCN.

Method 3 Chromatographic Parameters

| | |
|---|---|
| Instrument | Agilent HPLC 1200 system |
| Column | Chiralcel OD-H, 4.6 × 250 mm, 5 μm |
| Mobile Phase (premixed) | 90% n-Hexane, 10% IPA |
| Flow Rate | 2.0 mL/min |
| Detection Wavelength | 230 nm |
| Column Temperature | 15° C. |
| Injection Volume | 10 μL |
| Run time | 35 min |
| (R)-Eslicarbazepine | 18.5 min |
| (S)-Eslicarbazepine | 27.3 min |

Enantiomeric purity was calculated as follows:

$$\% \text{ e.e.} = \frac{[\text{Peak Area of } (S)\text{-licarbazepine}] - [\text{Peak Area of } (R)\text{-licarbazepine}]}{[\text{Peak Area of } (S)\text{-licarbazepine}] + [\text{Peak Area of } (R)\text{-licarbazepine}]} \times 100$$

Method 4—Determining Acetone and IPA Concentration (GC).

Samples for GC analysis were prepared by taking 100 μL of reaction solution and adding it to 900 μL of methanol. Samples were centrifuged for 1-2 min and 200 μL of supernatant dispensed into a GC glass vial with insert.

Method 4 Chromatographic Parameters

| | |
|---|---|
| Instrument | Agilent GC 6890N |
| Column | Roticap WAX Capillary, 50 m × 250 μm (ID) × 0.25 μm (FT) |
| Gas flow | Helium with split ratio 60:1 |
| Inlet Pressure | 22.4 psi |
| Column Pressure | 6.0 psi |
| Helium flow rate | 1.1 mL/min (Constant Pressure Mode) |
| Inlet Temperature | 180° C. |
| Detector Temperature | 200° C. |
| FID Hydrogen Flow | 30 mL/min |
| FID Air Flow | 350 mL/min |
| FID Nitrogen Flow | 35 mL/min |
| Injection Volume | 1 μL |
| Run time | 6.71 min |
| Acetone Retention Time | 3.97 min |
| IPA Retention Time | 4.41 min |

Temperature Program:

| Oven Ramp | ° C./min | Next ° C. | Hold Time (min) | Run Time (min) |
|---|---|---|---|---|
| Initial | | 65 | 0 | 0 |
| Ramp | 7 | 105 | 1 | 6.71 |

Method 5—Determining (S)-Licarbazepine % Potency.

Samples were prepared by placing 1.0 mg of reference standard into a 5 mL volumetric flask and adding 4 mL MeCN to disperse the solid. The mixture was sonicated for 5 min, then made up to volume with MeCN. After passing through a 0.5 µm disc membrane, a sample was injected into the HPLC using the chromatographic conditions specified below. Isolated sample solution was prepared in the same way.

Method 5 Chromatographic Parameters

| | |
|---|---|
| Instrument | Agilent 1200 HPLC system |
| Column | Agilent Eclipse XDB C18 4.6 × 150 mm, 5 µm |
| Mobile Phase (Premixed) | MeCN/0.1% HOAc in water (25/75) |
| Detection Wavelength | 230 nm |
| Column Temperature | 25° C. |
| Injection Volume | 10 µL |
| Run time | 10 min |
| Flow rate | 1.0 mL/min |
| % Potency | 96.2 |
| LOD | <0.2 ppm (S/N~3) |
| LOQ | <0.6 ppm (S/N~10) |

Percent (%) potency was calculated as follows:

$$\% \text{ potency} = \frac{\text{Peak Area of Sample} \times \text{Weight of Std} \times \text{Potency of Std}}{\text{Peak Area of Std} \times \text{Weight of Sample}} \times 100$$

Example 5

Biocatalytic Process I for Preparation of Compound (1c) from Compound (2c)—50 g Scale Reaction This example illustrates a second biocatalytic process using an engineered ketoreductase polypeptide to prepare compound (1c) on a 50 g scale. The reaction is carried out in an aqueous co-solvent system of 0.1M TEA, 1 mM MgSO$_4$, pH 10, 60% IPA, and compound (2c) loading of 100 g/L. The engineered ketoreductase (SEQ ID NO: 36) was at a loading of 1 g/L along with co-factor NADPH at 0.1 g/L. This protocol afforded 48 g (96% isolated yield) of crude desired product in one run with 98.7% chemical purity (w/w, as determined by HPLC Method 5), >99.9% enantiomeric excess (as determined by HPLC Method 3) and a protein residue content of <100 ppm.

Biocatalytic Reaction Procedure.

A 1 L jacketed reactor was charged sequentially with the 300 mL of IPA, 190 mL of TEA buffer solution (pH 10.0), and oxcarbazepine 50.0 g (charged as solid under stirring). The reaction vessel was equipped with an overhead stirrer fitted with an anchor shaped stir blade, a temperature probe, a nitrogen inlet connected to a flow meter and an outlet for solvent collection. The reaction mixture was stirred at 200 rpm and heated until an internal temperature of 55° C. was attained. A stock solution of enzyme and NADP, prepared separately in buffer, was charged to the reaction mixture at 55° C. The reaction mixture was stirred at 55° C., 200 rpm under a nitrogen atmosphere with a flow rate of 0.8 liters per minute. The reaction volume was maintained by the intermittent addition of a pre-mixed solution of 60% IPA and 40% buffer (0.1 M TEA with 1 mM MgSO$_4$, pH 10.0). The reaction course was followed periodically by taking samples from the reaction mixture, quenching, and analyzing as described in Method 1. Samples were also frequently monitored for acetone content using the procedure described in Method 4. For the purposes of tracking the process, t=0 was set at the time at which the enzyme was added. After in-process analyses indicated >99% conversion in 24 h, the reaction mixture was taken for subsequent workup and isolation.

Following complete conversion (>99%), the reaction mixture was drained from the reactor into a 1 L round-bottom flask. IPA was distilled by rotary evaporation (75 torr, 50° C. bath). Upon partial distillation of reaction volume, 100 mL of water was added to the white slurry and the distillation continued to completely remove IPA.

The crude product was collected by filtration through a Buchner funnel and washed with water (100 mL) and heptane (200 mL). The solid was dried for 24 h in a vacuum oven (2 mbar) at 30° C. Upon drying, 48.0 g (96% yield) of crude product was obtained as an off white solid with a chemical purity of 98.7% (as determined by HPLC Method 5) with >99.9% e.e (as determined by HPLC Method 3) and a residual protein content of 80 ppm.

Purification of Compound (1c).

A 10 g suspension of crude product from above in 100 ml methanol was heated to 40° C. (internal temperature) to allow maximum dissolution of product. Celite (2.0 g) was added to the slightly turbid solution, and the mixture was stirred at 40° C. for 15-20 minutes. The slurry with Celite was then filtered through a sintered funnel, and the residue was washed with 20 mL of pre-heated (~40° C.) methanol. The clear filtrate obtained was then distilled under reduced pressure to reduce the volume to approximately 30 mL. The thick solution was gradually cooled to 5° C. using an ice-bath. Cold water (50 mL) was added dropwise to the white precipitate, and the resulting slurry was stirred at 5° C. for 30 minutes. The precipitated product was filtered through a sintered funnel, rinsed and washed with 20 mL of water before being dried in a vacuum oven for 16 h (30° C., 2 mbar). This resulted in 9.0 g (90% recovery) of purified product in a single run as a white solid with 99.6% chemical purity (as determined by HPLC Method 5) and a residual protein content of <10 ppm.

Analytical Methods Used in the Process of Example 4:

Chromatographic methods were employed to analyze the products of the ketoreductase mediated conversion of compound (2c) to compound (1c)

Method 1—Rapid Conversion Method.

1 mL of reaction mixture was quenched in 9 mL of pre-mixed solution of 1:1 DMSO:MeCN. The sample was sonicated to completely dissolve any undissolved substrate or product. The sample was then centrifuged to separate the enzyme from the solution. 50 µL of supernatant was added to 950 µL MeCN and submitted for analysis.

Method 1 Chromatographic Parameters

| | |
|---|---|
| Instrument | Agilent 1200 HPLC system |
| Column | Agilent Eclipse XDB C18 4.6 × 150 mm, 5 µm |
| Mobile Phase | MeCN/0.1% AcOH in water (40/60, Isocratic) |
| Column temperature | 25° C. |
| Flow rate | 1.4 mL/min |
| Injection volume | 10 µL |
| UV Wavelength | 210 nm |
| Runtime | 2.7 min |
| Substrate | 1.91 min |
| Linearity | 0.99 (R2 at 2-200 ppm substrate and product) |
| RF (product to substrate) | 1.23 |

The % conversion was calculated from the chromatogram as follows:

$$\% \text{ Conversion} = \frac{[\text{Peak Area of product}]}{[\text{Peak Area of product}] + [\text{Peak Area of substrate} \times RF]} \times 100\%$$

Method 2—Purity Method (HPLC).

To prepare the sample for analysis, 20.0 mg of isolated eslicarbazepine was weighed into 100 mL volumetric flask and dissolved in approximately 80 mL in MeCN. The mixture was sonicated for 5 min and topped up to volume with MeCN. Alternatively, the reaction sample prepared in Method 1 above can also be used in this method to determine in-process purity and % conversion.

Method 2 Chromatographic Parameters

| Instrument | Agilent 1200 HPLC system |
|---|---|
| Column | Agilent Eclipse XDB C18 4.6 × 150 mm, 5 μm |
| Mobile Phase (premixed) | Gradient |
| | Eluent A: MeCN |
| | Eluent B: 0.1% AcOH in water |

| Time (min) | Eluent A (%) | Eluent B (%) |
|---|---|---|
| 0 | 20 | 80 |
| 12 | 30 | 70 |
| 18 | 50 | 50 |
| 20 | 50 | 50 |
| 22 | 20 | 80 |

| Detection Wavelength | 210 nm |
|---|---|
| Column Temperature | 25° C. |
| Injection Volume | 10 μL |
| Run time | 22 min |
| Equilibration time | 5 min |
| Product | 7.03 min |
| Substrate | 11.34 min |
| Flow rate | 1.0 mL/min |

The % conversion was calculated by the same method described in Method 1 above.

Method 3—Chiral Method (HPLC).

To prepare the sample, 40.0 mg of isolated S-licarbazepine was weighed into a 100 mL volumetric flask and dissolved in 80 mL of MeCN. The mixture was sonicated for 5 min and topped up to volume with MeCN.

Method 3 Chromatographic Parameters

| Instrument | Agilent 1200 HPLC system |
|---|---|
| Column | ChiraDex ®, LiChroCART ® 250-4, 5 μm |
| Mobile Phase (premixed) | 95% $Na_2HPO_4$ (100 mM; pH 7.0) and 5% MeOH |
| Column temperature | 15° C. |
| Flow rate | 1.0 mL/min |
| Injection volume | 10 μL |
| Detection Wavelength | 254 nm |
| Runtime | 24 min |
| R-licarbazepine | 15.4 min |
| S-licarbazepine | 18.3 min |

$$\% \text{ e.e.} = \frac{[\text{Peak Area of } S\text{-licarbazepine}] - [\text{Peak Area of } R\text{-licarbazepine}]}{[\text{Peak Area of } S\text{-licarbazepine}] + [\text{Peak Area of } R\text{-licarbazepine}]} \times 100$$

Method 4—Residual Solvent Detection Method (GC).

Sample was prepared by diluting 1 mL of reaction mixture with 9 mL of methanol, prior to centrifugation for 1 min. The supernatant was removed for GC analysis.

Method 4 Chromatographic Parameters

| Instrument | Agilent GC 6890N |
|---|---|
| Column | Roticap WAX Capillary, 50 m × 250 μm (ID) × 0.25 μm (FT) |
| Gas flow | Helium with split ratio 60:1 |
| Inlet Pressure | 22.4 psi |
| Column Pressure | 6.0 psi |
| Helium flow rate | 1.1 mL/min (Constant Pressure Mode) |
| Inlet Temperature | 180° C. |
| Detector Temperature | 200° C. |
| FID Hydrogen Flow | 30 mL/min |
| FID Air Flow | 350 mL/min |
| FID Nitrogen Flow | 35 mL/min |
| Injection Volume | 1 μL |
| Run time | 6.7 min |
| Acetone Retention Time | 3.9 min |
| IPA Retention Time | 4.4 min |

Temperature Program

| Oven Ramp | ° C./min | Next ° C. | Hold Time (min) | Run Time (min) |
|---|---|---|---|---|
| Initial | | 65 | 0 | 0 |
| Ramp | 7 | 105 | 1 | 6.71 |

Method 5—Potency Method (HPLC).

1.0 mg of reference standard eslicarbazepine was dissolved with 4 mL MeCN in a 5 mL volumetric flask. The solution was sonicated for 5 min and made up to volume with MeCN. After filtering the solution through a 0.5 μm disc membrane, sample was used for HPLC analysis. Sample with isolated eslicarbazepine was prepared in a similar manner.

Method 5 Chromatographic Parameters

| Instrument | Agilent 1200 HPLC system |
|---|---|
| Column | Agilent Eclipse XDB C18 4.6 × 150 mm, 5 μm |
| Mobile Phase (Premixed) | MeCN/0.1% AcOH in water (25/75) |
| Detection Wavelength | 230 nm |
| Column Temperature | 25° C. |
| Injection Volume | 10 μL |
| Run time | 10 min |
| Flow rate | 1.0 mL/min |
| LOD | <0.2 ppm (S/N~3) |
| LOQ | <0.6 ppm (S/N~10) |

% potency of isolated product is calculated as follows:

$$\% \text{ potency} = \frac{\text{Peak Area of Sample} \times \text{Weight of Standard} \times \text{Potency of Standard}}{\text{Peak Area of Standard} \times \text{Weight of Sample}} \times 100$$

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A non-naturally occurring polynucleotide encoding a polypeptide capable of converting compound (2c)

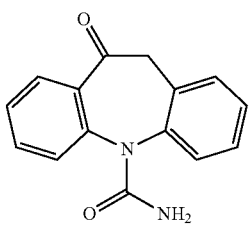

(2c)

to compound (1c)

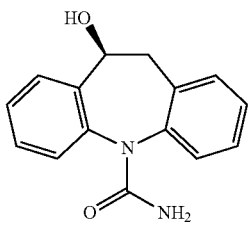

(1c)

in enantiomeric excess in presence of NADPH, the ketoreductase polypeptide comprising an amino acid sequence that has at least 80% sequence identity to SEQ ID NO:10 and has at least the following features:

X80 is T; X96 is V or R; X145 is L; X153 is T; X190 is P; X196 is L or M; and X226 is V.

2. The non-naturally occurring polynucleotide of claim 1, wherein the encoded polypeptide sequence has at least 93% sequence identity to SEQ ID NO: 36.

3. The non-naturally occurring polynucleotide of claim 1, wherein the encoded polypeptide sequence further comprises one or more of the following features: X17 is H; X29 is T; X43 is R; X71 is P or G; X87 is L; X95 is Y; X131 is C; X173 is L; and X199 is M.

4. The non-naturally occurring polynucleotide of claim 1, wherein the encoded polypeptide sequence further comprises one or more of the following features: X17 is M or H; X29 is T; X40 is R; X43 is R or V; X64 is V; X94 is G or A; X95 is Y or M; X147 is Q or M; X152 is L or A; X157 is C or S; X173 is L; X199 is M; and X200 is P.

5. The non-naturally occurring polynucleotide of claim 1, where the encoded polypeptide sequence further comprises one or more of the following features: X25 is T; X76 is A; X144 is V; X150 is L; X194 is R; X233 is G; and X249 is W or F.

6. The non-naturally occurring polynucleotide of claim 1, wherein the encoded polypeptide sequence comprises at least the following features: X64 is V; X71 is P or G; X80 is T; X87 is L; X94 is G or A; X96 is V or R; X145 is L; X147 is Q or M; X153 is T; X173 is L; X190 is P; X196 is M or L; X199 is M; and X226 is V.

7. The non-naturally occurring polynucleotide of claim 1, wherein the encoded polypeptide sequence further comprises one or more of the following features: X17 is M or H; X29 is T; X40 is R; X43 is R or V; X95 is M or Y; X131 is C; X152 is L or A; and X200 is P.

8. The non-naturally occurring polynucleotide of claim 1, wherein the encoded polypeptide sequence further comprises one or more of the following features: X25 is T; X76 is A; X144 is V; X150 is L; X157 is C or S; X194 is R; X233 is G; and X249 is W or F.

9. The non-naturally occurring polynucleotide of claim 1, wherein the encoded polypeptide sequence comprises at least the following features: X17 is H or M; X25 is T; X29 is T; X40 is R; X43 is R or V; X64 is V; X71 is G or P; X80 is T; X87 is L; X94 is G; X95 is Y or M; X96 is R or V; X131 is C; X145 is L; X147 is Q or M; X152 is A or L; X153 is T; X157 is S or C; X173 is L; X190 is P; X196 is M or L; X199 is M; X200 is P; and X226 is V.

10. The non-naturally occurring polynucleotide of claim 9, wherein the encoded polypeptide sequence further comprises one or more of the following features: X76 is A; X144 is V; X150 is L; X194 is R; X233 is G; and X249 is W or F.

11. The non-naturally occurring polynucleotide of claim 1, wherein the encoded polypeptide sequence comprises a sequence selected from SEQ ID NO: 6, 8, 10, 12, 14, 16, 18, 20, 22, 24, 26, 28, 30, 32, 34, 36, and 38.

12. A non-naturally occurring polynucleotide that encodes a polypeptide sequence comprising an amino acid sequence having at least 80% sequence identity to SEQ ID NO:2 and having one or more residue differences as compared to the reference sequence of SEQ ID NO:2 at residue positions corresponding to X71, X87, and X131, wherein the polypeptide has ketoreductase activity.

13. The non-naturally occurring polynucleotide of claim 12, wherein encoded polypeptide sequence comprises one or more of the following features: X71 is P or G; X87 is L, and X131 is C.

14. The non-naturally occurring polynucleotide of claim 1, wherein the encoded polypeptide sequence is immobilized on a solid support.

15. The non-naturally occurring polynucleotide of claim 12, wherein the encoded polypeptide sequence is immobilized on a solid support.

16. An isolated polynucleotide encoding the polypeptide of claim 12.

17. An isolated polynucleotide comprising a nucleotide sequence selected from the group consisting of SEQ ID NO: 3, 5, 7, 9, 11, 13, 15, 17, 19, 21, 23, 25, 27, 29, 31, 33, 35, and 37.

18. An expression vector comprising the polynucleotide of claim 1.

19. An expression vector comprising the polynucleotide of claim 16.

20. An expression vector comprising the polynucleotide of claim 17.

* * * * *

SEQUENCE LISTING

<160> NUMBER OF SEQ ID NOS: 38

<210> SEQ ID NO 1
<211> LENGTH: 759
<212> TYPE: DNA
<213> ORGANISM: Artificial Sequence
<220> FEATURE:
<223> OTHER INFORMATION: Codon-optimized L. kefir ketoreductase gene

<400> SEQUENCE: 1

```
atgaccgatc gtctgaaggg caaagtagcc atcgtaaccg gcgggactct gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg catccgatga agcaggctgg acgaaactgt tcgacaccac cgaggaggca     240
ttcggcccgg ttacgaccgt cgtgaacaat gcagggattg cagtttccaa agcgttgaa     300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagta ttgagggtt cgtaggcgat ccgacgctgg gggcatacaa cgcttccaag     480
ggggcggtac gtatcatgtc gaaaagcgca gcgctggatt gcgcactgaa ggactacgat     540
gtgcgtgtca acacagtaca tccgggctat atcaagaccc cgctggtcga tgatctggaa     600
ggtgctgagg aaatgatgtc acagcgtacg aaaaccccta tgggccacat tggcgaaccg     660
aatgacatcg catggatctg tgtgtacctg gcatctgacg aatcgaaatt tgcgacgggt     720
gcagaatttg tggtcgacgg cgggtatacc gcacagtga                           759
```

<210> SEQ ID NO 2
<211> LENGTH: 252
<212> TYPE: PRT
<213> ORGANISM: Lactobacillus kefir

<400> SEQUENCE: 2

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Ala
65                  70                  75                  80

Phe Gly Pro Val Thr Thr Val Val Asn Asn Ala Gly Ile Ala Val Ser
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Thr Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175
```

```
Lys Asp Tyr Asp Val Arg Val Asn Thr Val His Pro Gly Tyr Ile Lys
            180                 185                 190

Thr Pro Leu Val Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Ile Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 3
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 3
atgaccgatc gtctgaaggg caaagtagcc atcgtaaccg gcgggacact gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgatga agcaggctgg acgaaactgt tcgacaccac cgaggagaca    240
ttcggcccgg ttacgaccgt cgtgaacaat gcagggattg gggttgttaa agcgttgaa     300 gacactacca cggaggaatg gcgtaaactg ctgtccgtta atctggatgg tgttttttc     360 ggcacccgtc tgggcattca gcgcatgaaa aataaaggct gggcgctag catcatcaat    420 atgagcagta ttctgggggtt cgtaggcgat ccgacgacgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgctgctcga tgatctggaa    600
ggtgctgagg aaatgatgtc acagcgtacg aaaaccccta tgggccacat tggcgaaccg    660
aatgacatcg catgggtctg tgtgtacctg gcatctgacg aatcgaaatt tgcgacgggt    720
gcagaatttg tggtcgacgg cgggtggacc gcacagtga                          759

<210> SEQ ID NO 4
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 4

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Thr
65                  70                  75                  80

Phe Gly Pro Val Thr Thr Val Val Asn Asn Ala Gly Ile Gly Val Val
                85                  90                  95
```

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Leu Gly Phe Val Gly Asp Pro Thr Thr Gly Ala Tyr Asn Ala Ser Lys
145                 150                 155                 160

Gly Ala Val Arg Ile Met Ser Lys Ser Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 5
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 5

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggagaca     240
ttcggcccgg ttacgaccgt cgtgaacaat gcaggattg gggttgttaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagta ttctggggtt cgtaggcgat ccgacgacgg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgctgctcga tgatctggaa     600
ggtgctgagg aaatgatgtc acagcgtacg aaaaccccta tgggtcacat ggcgaaccg      660
aatgacatcg catgggtctg tgtgtacctg gcatctgacg aatcgaaatt tgcgacgggt     720
gcagaatttg tggtcgacgg cgggtggacc gcacagtga                            759
```

<210> SEQ ID NO 6
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 6

Met Thr Asp Arg Leu Lys Gly Lys Val Ala Ile Val Thr Gly Gly Thr
1               5                   10                  15

-continued

Leu Gly Ile Gly Leu Ala Ile Ala Asp Lys Phe Val Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Thr
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Leu Gly Phe Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 7
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 7
atgaccgatc gtctgaaggg caaagtagcc atcgtaaccg gcgggacact gggtatcggt        60
ttggcaatcg ccgataaatt tgtagaggag ggtgcgaaag tagttattac tggtcgtcac       120
gcggatgtag gtgaaaaggc cgccaaatca atcggcggca ctgatgttat tcgctttgtc       180
cagcacgatg cgtccgatga agcaggctgg acgaaactgt tcgacaccac cgaggagaca       240
ttcggcccgg ttacgaccgt cgtgaacaat gcagggattg ggttgttaa aagcgttgaa        300
gacactacca cggaggaatg gcgtaaactg ctgtccgtta atctggatgg tgttttttc        360
ggcacccgtc tgggcattca gcgcatgaaa aataaaggct gggcgctag catcatcaat       420
atgagcagta ttctggggca ggtaggcgat ccgacgacgg gggcatacaa cgcttccaag       480
ggggcggtac gtatcatgtc gaaaagcgca gcgctggatt gcgcactgaa ggactacgat       540
gtgcgtgtca acacagtaca tccgggcccc atcaagaccc cgctgctcga tgatctggaa       600
ggtgctgagg aaatgatgtc acagcgtacg aaaaccccta tgggtcacat tggcgaaccg       660
aatgacatcg catgggtctg tgtgtacctg gcatctgacg aatcgaaatt tgcgacgggt       720
gcagaatttg tggtcgacgg cgggtggacc gcacagtga            759

<210> SEQ ID NO 8
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 8

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Thr
65                  70                  75                  80

Phe Gly Pro Val Thr Thr Val Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
130                 135                 140

Leu Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Trp Thr Ala Gln
                245                 250

<210> SEQ ID NO 9
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 9
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggagaca     240
ttcggcccgg ttacgaccgt cgtgaacaat gcagggattg gggttgttaa aagcgttgaa     300

-continued

```
gacactacca cggaggaatg gcgtaaactg ctgtccgtta atctggatgg tgttttttc      360
ggcacccgtc tgggcattca gcgcatgaaa aataaaggct tgggcgctag catcatcaat    420
atgagcagta ttctgggggtt cgtaggcgat ccgacgacgg gggcatacaa cgcttccaag   480
ggggcggtac gtatcatgtc gaaaagcgca gcgctggatt gcgcactgaa ggactacgat    540
gtgcgtgtca acacagtaca tccgggcccc atcaagaccc cgctgctcga tgatctggaa   600
ggtgctgagg aaatgatgtc acagcgtacg aaaaccccta tgggtcacat ggcgaaccg    660
aatgacatcg catgggtctg tgtgtacctg gcatctgacg aatcgaaatt tgcgacgggt   720
gcagaatttg tggtcgacgg cgggtatacc gcacagtga                          759
```

<210> SEQ ID NO 10
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 10

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Thr
65                  70                  75                  80
Phe Gly Pro Val Thr Thr Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Leu Gly Phe Val Gly Asp Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Leu Leu Asp Asp Leu Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
Trp Val Cys Val Tyr Leu Ala Ser Asp Glu Ser Lys Phe Ala Thr Gly
225                 230                 235                 240
Ala Glu Phe Val Val Asp Gly Gly Tyr Thr Ala Gln
                245                 250
```

<210> SEQ ID NO 11
<211> LENGTH: 759
<212> TYPE: DNA

-continued

<213> ORGANISM: Artificial Sequence
<220> FEATURE:
<223> OTHER INFORMATION: Engineered variant of L. kefir ketoreductase

<400> SEQUENCE: 11

```
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggagaca     240
ttcggcccgg ttacgaccgt cgtgaacaat gcagggattg ggttgttaa aagcgttgaa      300
gacactacca cggaggaatg gcgtaaactg ctgtccgtta atctggatgg tgttttttc     360
ggcacccgtc tgggcattca gcgcatgaaa aataaaggct gggcgctag catcatcaat     420
atgagcagta ttctggggtt cgtaggctta ccgacgacgg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc cgctgatgga tgatatggaa     600
ggtgctgagg aaatgatgtc acagcgtacg aaaacccccta tgggtcacat tggcgaaccg     660
aatgacatcg catgggtctg tgtgtacctg gcatctgacg aatcgaaatt tgcgacgggt     720
gcagaatttg tggtcgacgg cgggtatacc gcacagtga                            759
```

<210> SEQ ID NO 12
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 12

```
Met Thr Asp Arg Leu Lys Gly Lys Val Ala Ile Val Thr Gly Gly Thr
1               5                   10                  15
Leu Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Thr
65                  70                  75                  80
Phe Gly Pro Val Thr Thr Val Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Ile
    130                 135                 140
Leu Gly Phe Val Gly Leu Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Pro Leu Met Asp Asp Met Glu Gly Ala Glu Glu Met Met Ser Gln
```

```
                195                 200                 205
Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 13
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 13

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgatga agcaggctgg acgaaactgt tcgacaccac cgaggagaca   240
ttcggcccgg ttacgaccgt cgtgaacaat gcagggattg ccgtggttaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagtt ttctggggtt cgtaggcgat ccgacgacgg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgttaatgga tgatatggaa   600
ggtgctgagg aaatgatgtc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggttcacc gcacagtga                          759
```

<210> SEQ ID NO 14
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 14

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Thr
65                  70                  75                  80

Phe Gly Pro Val Thr Thr Val Val Asn Asn Ala Gly Ile Ala Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
```

```
                115                 120                 125
Met Lys Asn Lys Gly Leu Gly Ala Ser Ile Ile Asn Met Ser Ser Val
            130                 135                 140

Leu Gly Phe Val Gly Asp Pro Thr Thr Gly Ala Tyr Asn Ala Ser Lys
145                 150                 155                 160

Gly Ala Val Arg Ile Met Ser Lys Ser Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Met Glu Gly Ala Glu Met Met Ser Gln
                195                 200                 205

Arg Thr Lys Thr Pro Met Gly His Ile Gly Glu Pro Asn Asp Ile Ala
            210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250
```

<210> SEQ ID NO 15
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 15

```
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg cgtccgatga agcaggctgg acgaaactgt tcgacaccac cgaggagaca   240
ttcggcccgg ttacgaccgt cgtgaacaat gcagggattg cgtggttaa aagcgttgaa   300
gacactacca cggaggaatg cgtaaactg ctgtccgtta atctggatgg tgttttttc   360
ggcacccgtc tgggcattca gcgcatgaaa aataaaggct tgggcgctag catcatcaat   420
atgagcagta ttctggggca ggtaggcgat ccgacgactg gggcatacaa cgcttccaag   480
ggggcggtac gtatcatgtc gaaaagcgca gcgctggatt gcgcactgaa ggactacgat   540
gtgcgtgtca acacagtaca tccgggcccc atcaagaccc cgttaatgga tgatatggaa   600
ggtgctgagg aaatgatgtc acagcgtacg aaaacccta tgggtcacat ggcgaaccg    660
aatgacatcg catgggtctg tgtgtacctg gcatctgacg aatcgaaatt tgcgacgggt   720
gcagaatttg tggtcgacgg cgggtatacc gcacagtga                        759
```

<210> SEQ ID NO 16
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 16

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
```

```
                 35                  40                  45
Lys Ser Ile Gly Gly Thr Asp Val Ile Arg Phe Val Gln His Asp Ala
 50                  55                  60

Ser Asp Glu Ala Gly Trp Thr Lys Leu Phe Asp Thr Thr Glu Glu Thr
 65                  70                  75                  80

Phe Gly Pro Val Thr Thr Val Val Asn Asn Ala Gly Ile Gly Val Val
                 85                  90                  95

Lys Ser Val Glu Asp Thr Thr Glu Glu Trp Arg Lys Leu Leu Ser
                100                 105                 110

Val Asn Leu Asp Gly Val Phe Phe Gly Thr Arg Leu Gly Ile Gln Arg
                115                 120                 125

Met Lys Asn Lys Gly Leu Gly Ala Ser Ile Ile Asn Met Ser Ser Ile
                130                 135                 140

Leu Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
                180                 185                 190

Thr Pro Leu Met Asp Asp Met Glu Gly Ala Glu Met Met Ser Gln
                195                 200                 205

Arg Thr Lys Thr Pro Met Gly His Ile Gly Glu Pro Asn Asp Ile Ala
210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 17
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 17

```
atgaccgatc gtctgaaggg caaagtagcc atcgtaaccg cgggacact  gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggagaca     240
ttcggcccgg ttacgaccgt cgtgaacaat gcagggattg gcatggttaa agcgttgaa      300
gacactacca cggaggaatg gcgtaaactg ctgtccgtta atctggatgg tgttttttc      360
ggcacccgtc tgggcattca gcgcatgaaa ataaaggct tgggcgctag catcatcaat      420
atgagcagtg ttctgggca ggtaggcgat ccgacgacgg gggcatacaa cgcttccaag      480
ggggcggtac gtatcatgtc gaaaagcgca gcgctggatt gcgcactgaa ggactacgat     540
gtgcgtgtca acacagtaca tccgggcccc atcaagaccc cgttaatgga tgatctggaa     600
ggtgctgagg aaatgatgtc acagcgtacg aaaaccccta tgggtcacat ggcgaaccg      660
aatgacatcg catgggtctg tgtgtacctg gcatctgacg aatcgaaatt tgcgacgggt     720
gcagaatttg tggtcgacgg cgggttcacc gcacagtga                           759
```

<210> SEQ ID NO 18

<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 18

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Thr
65                  70                  75                  80

Phe Gly Pro Val Thr Thr Val Val Asn Asn Ala Gly Ile Gly Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Leu Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Leu Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Phe Thr Ala Gln
                245                 250

<210> SEQ ID NO 19
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 19
atgaccgatc gtctgaaggg caaagtagcc atcgtaaccg gcgggacact gggtatcggt     60
ttggcaatcg ccgataaatt tgtagaggag ggtgcgaaag tagttattac tggtcgtcac    120
gcggatgtag gtgaaaaggc cgccaaatca atcggcggca ctgatgttat tcgctttgtc    180
cagcacgatg cgtccgatga agcaggctgg acgaaactgt tcgacaccac cgaggagaca    240
ttcggcccgg ttacgaccgt cgtgaacaat gcaggattg gcatggttaa aagcgttgaa     300
gacactacca cggaggaatg gcgtaaactg ctgtccgtta atctggatgg tgttttttc     360 ggcacccgtc tgggcattca gcgcatgaaa aataaaggct tgggcgctag catcatcaat    420

```
atgagcagtg ttctggggtt cgtaggcgat ccgacgacgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgttactgga tgatatggaa    600
ggtgctgagg aaatgatgtc acagcgtacg aaaaccccta tgggtcacat tggcgaaccg    660
aatgacatcg catgggtctg tgtgtacctg gcatctgacg aatcgaaatt tgcgacgggt    720
gcagaatttg tggtcgacgg cgggtatacc gcacagtga                          759
```

<210> SEQ ID NO 20
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 20

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Val Gly Glu Lys Ala Ala
        35                  40                  45

Lys Ser Ile Gly Gly Thr Asp Val Ile Arg Phe Val Gln His Asp Ala
    50                  55                  60

Ser Asp Glu Ala Gly Trp Thr Lys Leu Phe Asp Thr Thr Glu Glu Thr
65                  70                  75                  80

Phe Gly Pro Val Thr Thr Val Val Asn Asn Ala Gly Ile Ala Met Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Val
    130                 135                 140

Leu Gly Phe Val Gly Asp Pro Thr Thr Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Pro Ile Lys
            180                 185                 190

Thr Pro Leu Leu Asp Asp Met Glu Gly Ala Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 21
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 21

```
atgaccgatc gtctgaaggg caaagtagcc atcgtaaccg gcgggacaat gggtatcggt      60
ttggcaatcg ccgataaatt tgtagaggag ggtgcgaaag tagttattac tggtcgtcac     120
gcggatgtag gtgaaaaggc cgccaaatca atcggcggca ctgatgttat tcgctttgtc     180
cagcacgatg cgtccgatga agcaggctgg acgaaactgt tcgacaccac cgaggagaca     240
ttcggcccgg ttacgaccgt cgtgaacaat gcagggattg gcgtggttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat      420
atgagcagtg ttctggggat ggtaggcttg ccgaccactg gggcatacaa cgcttccaag     480
ggggcggtac gtatcatgtc gaaaagcgca gcgctggatt gcgcactgaa ggactacgat     540
gtgcgtgtca acacagtaca tccgggcccc atcaagaccc gtttaatgga tgatatggaa     600
ggtgctgagg aaatgatgtc acagcgtacg aaaacccta tgggtcacat tggcgaaccg      660
aatgacatcg catgggtctg tgtgtacctg gcatctgacg aatcgaaatt tgcgacgggt     720
gcagaatttg tggtcgacgg cgggtatacc gcacagtga                            759
```

<210> SEQ ID NO 22
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 22

```
Met Thr Asp Arg Leu Lys Gly Lys Val Ala Ile Val Thr Gly Gly Thr
1               5                   10                  15
Met Gly Ile Gly Leu Ala Ile Ala Asp Lys Phe Val Glu Glu Gly Ala
            20                  25                  30
Lys Val Val Ile Thr Gly Arg His Ala Asp Val Gly Glu Lys Ala Ala
        35                  40                  45
Lys Ser Ile Gly Gly Thr Asp Val Ile Arg Phe Val Gln His Asp Ala
    50                  55                  60
Ser Asp Glu Ala Gly Trp Thr Lys Leu Phe Asp Thr Thr Glu Glu Thr
65                  70                  75                  80
Phe Gly Pro Val Thr Thr Val Asn Asn Ala Gly Ile Gly Val Val
                85                  90                  95
Lys Ser Val Glu Asp Thr Thr Thr Glu Glu Trp Arg Lys Leu Leu Ser
            100                 105                 110
Val Asn Leu Asp Gly Val Phe Phe Gly Thr Arg Leu Gly Ile Gln Arg
        115                 120                 125
Met Lys Asn Lys Gly Leu Gly Ala Ser Ile Ile Asn Met Ser Ser Val
    130                 135                 140
Leu Gly Met Val Gly Leu Pro Thr Thr Gly Ala Tyr Asn Ala Ser Lys
145                 150                 155                 160
Gly Ala Val Arg Ile Met Ser Lys Ser Ala Ala Leu Asp Cys Ala Leu
                165                 170                 175
Lys Asp Tyr Asp Val Arg Val Asn Thr Val His Pro Gly Pro Ile Lys
            180                 185                 190
Thr Arg Leu Met Asp Asp Met Glu Gly Ala Glu Glu Met Met Ser Gln
        195                 200                 205
Arg Thr Lys Thr Pro Met Gly His Ile Gly Glu Pro Asn Asp Ile Ala
    210                 215                 220
```

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 23
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 23

```
atgaccgatc gtctgaaggg caaagtagcc atcgtaaccg gcgggacact gggtatcggt     60
ttggcaatcg ccgataaatt tgtagaggag ggtgcgaaag tagttattac tggtcgtcac    120
gcggatcgcg gtgaaaaggc cgccaaatca atcggcggca ctgatgttat tcgctttgtc    180
cagcacgatg tttccgatga agcaggctgg ccaaaactgt tcgacaccac cgaggagaca    240
ttcggcccgg ttacgaccct ggtgaacaat gcagggattg gcgtggttaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttctggggca ggtaggcgat ccgacgactg gggcatacaa cgcttccaag    480
ggggcggtac gtatcatgtc gaaaagcgca gcgctgctgt gcgcactgaa ggactacgat    540
gtgcgtgtca acacagtaca tccgggcccc atcaagaccc cgttaatgga tgatatggaa    600
ggtgctgagg aaatgatgtc acagcgtacg aaaacccta tgggtcacat ggcgaaccg    660
aatgacatcg catgggtctg tgtgtacctg gcatctgacg aatcgaaatt tgcgacgggt    720
gcagaatttg tggtcgacgg cgggtatacc gcacagtga                          759
```

<210> SEQ ID NO 24
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 24

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Arg Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Thr
65                  70                  75                  80

Phe Gly Pro Val Thr Thr Leu Val Asn Asn Ala Gly Ile Gly Val Val
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Leu Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
            165                 170                 175

Lys Asp Tyr Asp Val Arg Val Asn Thr Val His Pro Gly Pro Ile Lys
            180                 185                 190

Thr Pro Leu Met Asp Asp Met Glu Gly Ala Glu Glu Met Met Ser Gln
            195                 200                 205

Arg Thr Lys Thr Pro Met Gly His Ile Gly Glu Pro Asn Asp Ile Ala
        210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 25
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 25
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcac     120
gcggatcgcg gtgaaaaggc cgccaaatca atcggcggca ctgatgttat tcgctttgtc     180
cagcacgatg tttccgatga agcaggctgg acgaaactgt tcgacaccac cgaggagaca     240
ttcggcccgg ttacgaccgt cgtgaacaat gcagggattg gcgtggttaa aagcgttgaa     300
gacactacca cggaggaatg cgtaaactg ctgtccgtta atctggatgg tgttttttc     360 ggcacccgtc tgggcattca gcgcatgaaa aataaaggct gggcgctag catcatcaat     420 atgagcagta ttctggggca ggtaggcgat ccgacgactg gggcatacaa cgcttccaag     480
ggggcggtac gtatcatgtc gaaaagcgca gcgctgctgt gcgcactgaa ggactacgat     540
gtgcgtgtca acacagtaca tccgggcccc atcaagaccc cgttaatgga tgatatggaa     600
ggtgctgagg aaatgatgtc acagcgtacg aaaaccccta tgggtcacat tggcgaaccg     660
aatgacatcg catgggtctg tgtgtacctg gcatctggcg aatcgaaatt tgcgacgggt     720
gcagaatttg tggtcgacgg cgggtatacc gcacagtga                           759

<210> SEQ ID NO 26
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 26

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Glu Glu Gly Ala
            20                  25                  30

Lys Val Val Ile Thr Gly Arg His Ala Asp Arg Gly Glu Lys Ala Ala
        35                  40                  45

Lys Ser Ile Gly Gly Thr Asp Val Ile Arg Phe Val Gln His Asp Val
    50                  55                  60

```
Ser Asp Glu Ala Gly Trp Thr Lys Leu Phe Asp Thr Thr Glu Glu Thr
 65                  70                  75                  80

Phe Gly Pro Val Thr Thr Val Val Asn Asn Ala Gly Ile Gly Val Val
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
            115                 120                 125

Met Lys Asn Lys Gly Leu Gly Ala Ser Ile Ile Asn Met Ser Ser Ile
130                 135                 140

Leu Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Met Glu Gly Ala Glu Glu Met Met Ser Gln
            195                 200                 205

Arg Thr Lys Thr Pro Met Gly His Ile Gly Glu Pro Asn Asp Ile Ala
210                 215                 220

Trp Val Cys Val Tyr Leu Ala Ser Gly Glu Ser Lys Phe Ala Thr Gly
225                 230                 235                 240

Ala Glu Phe Val Val Asp Gly Gly Tyr Thr Ala Gln
                245                 250

<210> SEQ ID NO 27
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 27
atgaccgatc gtctgaaggg caaagtagcc atcgtaaccg cgggacact gggtatcggt    60 ttggcaatcg ccgataaatt tgtagaggag ggtgcgaaag tagttattac tggtcgtcgc   120
gcggatcgcg tgaaaaggc cgccaaatca atcggcggca ctgatgttat tcgctttgtc   180
cagcacgatg tttccgatga agcaggctgg ccaaaactgt cgacaccac cgaggagaca   240 ttcggcccgg ttacgaccct ggtgaacaat gcagggattg gcgtggttaa aagcgttgaa   300
gacactacca cggaggaatg gcgtaaactg ctgtccgtta atctggatgg tgttttttc    360 ggcacccgtc tgggcattca gcgcatgaaa aataaaggct gggcgctag catcatcaat   420 atgagcagta ttctggggca ggtaggcgat ccgacgactg ggcatacaa cgcttccaag   480 ggggcggtac gtatcatgtc gaaaagcgca gcgctgctgt gcgcactgaa ggactacgat   540
gtgcgtgtca acacagtaca tccgggcccc atcaagaccc cgttaatgga tgatatggaa   600
ggtgctgagg aaatgatgtc acagcgtacg aaaaccccta tgggtcacat tggcgaaccg   660
aatgacatcg catgggtctg tgtgtacctg gcatctgacg aatcgaaatt tgcgacgggt   720
gcagaatttg tggtcgacgg cgggtatacc gcacagtga                         759

<210> SEQ ID NO 28
<211> LENGTH: 252
<212> TYPE: PRT
<213> ORGANISM: Artificial Sequence
<220> FEATURE:
```

<223> OTHER INFORMATION: Engineered variant of L. kefir ketoreductase

<400> SEQUENCE: 28

| | | | | | | | | | | | | | | | |
|---|---|---|---|---|---|---|---|---|---|---|---|---|---|---|---|
| Met | Thr | Asp | Arg | Leu | Lys | Gly | Lys | Val | Ala | Ile | Val | Thr | Gly | Gly | Thr |
| 1 | | | | 5 | | | | | 10 | | | | | 15 | |

Leu Gly Ile Gly Leu Ala Ile Ala Asp Lys Phe Val Glu Glu Gly Ala
              20                  25                  30

Lys Val Val Ile Thr Gly Arg Arg Ala Asp Arg Gly Glu Lys Ala Ala
          35                  40                  45

Lys Ser Ile Gly Gly Thr Asp Val Ile Arg Phe Val Gln His Asp Val
      50                  55                  60

Ser Asp Glu Ala Gly Trp Pro Lys Leu Phe Asp Thr Thr Glu Glu Thr
65                  70                  75                  80

Phe Gly Pro Val Thr Thr Leu Val Asn Asn Ala Gly Ile Gly Val Val
                  85                  90                  95

Lys Ser Val Glu Asp Thr Thr Thr Glu Glu Trp Arg Lys Leu Leu Ser
              100                 105                 110

Val Asn Leu Asp Gly Val Phe Phe Gly Thr Arg Leu Gly Ile Gln Arg
          115                 120                 125

Met Lys Asn Lys Gly Leu Gly Ala Ser Ile Ile Asn Met Ser Ser Ile
      130                 135                 140

Leu Gly Gln Val Gly Asp Pro Thr Thr Gly Ala Tyr Asn Ala Ser Lys
145                 150                 155                 160

Gly Ala Val Arg Ile Met Ser Lys Ser Ala Ala Leu Leu Cys Ala Leu
                  165                 170                 175

Lys Asp Tyr Asp Val Arg Val Asn Thr Val His Pro Gly Pro Ile Lys
              180                 185                 190

Thr Pro Leu Met Asp Asp Met Glu Gly Ala Glu Glu Met Met Ser Gln
          195                 200                 205

Arg Thr Lys Thr Pro Met Gly His Ile Gly Glu Pro Asn Asp Ile Ala
      210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                  245                 250

<210> SEQ ID NO 29
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 29

```
atgaccgatc gtctgaaggg caaagtagcc atcgtaaccg gcgggacact gggtatcggt      60
ttggcaatcg ccgataaatt tgtaacagag ggtgcgaaag tagttattac tggtcgtcgc     120
gcggatcgcg gtgaaaaggc cgccaaatca atcggcggca ctgatgttat tcgctttgtc     180
cagcacgatg tttccgatga agcaggctgg ccaaaactgt tcgacgccac cgaggagaca     240
ttcggcccgg tcacgaccct ggtgaacaat gcagggattg ctatcgcaa aagcgttgaa      300 gacactacca cggaggaatg gcgtaaactg ctgtccgtta atctggatgg tgttttttc      360 ggcacccgtc tgggcattca gcgcatgaaa aataaaggct tgggcgctag catcatcaat     420
atgagcagta ttctggggca ggtaggcgat ccgttaactg ggcatactg tgcttccaag      480 ggggcggtac gtatcatgtc gaaaagcgca gcgctgctgt gcgcactgaa ggactacgat     540
```

```
gtgcgtgtca acacagtaca tccgggcccc atcaagaccc cgttaatgga tgatatgccg      600
ggtgctgagg aaatgatgtc acagcgtacg aaaacccta tgggtcacat ggcgaaccg        660 aatgacatcg catgggtctg tgtgtacctg gcatctgacg aatcgaaatt tgcgacgggt     720
gcagaatttg tggtcgacgg cgggtatacc gcacagtga                             759
```

<210> SEQ ID NO 30
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 30

```
Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Thr Glu Gly Ala
            20                  25                  30

Lys Val Val Ile Thr Gly Arg Arg Ala Asp Arg Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Ala Thr Glu Glu Thr
65                  70                  75                  80

Phe Gly Pro Val Thr Thr Leu Val Asn Asn Ala Gly Ile Gly Tyr Arg
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Leu Gly Gln Val Gly Asp Pro Leu Thr Gly Ala Tyr Cys Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Met Pro Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 31
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 31

```
atgaccgatc gtctgaaggg caaagtagcc atcgtaaccg gcgggacact gggtatcggt      60
```

-continued

```
ttggcaatcg ccgataaatt tgtaacagag ggtgcgaaag tagttattac tggtcgtcgc    120
gcggatcgcg gtgaaaaggc cgccaaatca atcggcggca ctgatgttat tcgctttgtc    180
cagcacgatg tttccgatga agcaggctgg ccaaaactgt tcgacaccac cgaggagaca    240
ttcggcccgg ttacgaccct ggtgaacaat gcagggattg gctatcgcaa aagcgttgaa    300
gacactacca cggaggaatg gcgtaaactg ctgtccgtta atctggatgg tgttttttc    360 ggcacccgtc tgggcattca gcgcatgaaa tgtaaaggct gggcgctag catcatcaat    420 atgagcagta ttctggggca ggtaggcgat ccggcgactg gggcatacaa cgcttccaag    480
ggggcggtac gtatcatgtc gaaaagcgca gcgctgctgt gcgcactgaa ggactacgat    540
gtgcgtgtca acacagtaca tccgggcccc atcaagaccc cgttaatgga tgatatggaa    600
ggtgctgagg aaatgatgtc acagcgtacg aaaaccccta tgggtcacat ggcgaaccg    660 aatgacatcg catgggtctg tgtgtacctg gcatctgacg aatcgaaatt tgcgacgggt    720
gcagaatttg tggtcgacgg cgggtatacc gcacagtga                            759
```

<210> SEQ ID NO 32
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 32

```
Met Thr Asp Arg Leu Lys Gly Lys Val Ala Ile Val Thr Gly Gly Thr
  1               5                  10                  15

Leu Gly Ile Gly Leu Ala Ile Ala Asp Lys Phe Val Thr Glu Gly Ala
             20                  25                  30

Lys Val Val Ile Thr Gly Arg Arg Ala Asp Arg Gly Glu Lys Ala Ala
         35                  40                  45

Lys Ser Ile Gly Gly Thr Asp Val Ile Arg Phe Val Gln His Asp Val
     50                  55                  60

Ser Asp Glu Ala Gly Trp Pro Lys Leu Phe Asp Thr Thr Glu Glu Thr
 65                  70                  75                  80

Phe Gly Pro Val Thr Thr Leu Val Asn Asn Ala Gly Ile Gly Tyr Arg
                 85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Cys Lys Gly Leu Gly Ala Ser Ile Ile Asn Met Ser Ser Ile
130                 135                 140

Leu Gly Gln Val Gly Asp Pro Ala Thr Gly Ala Tyr Asn Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Met Glu Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240
```

Ala Glu Phe Val Val Asp Gly Gly Tyr Thr Ala Gln
                245                 250

<210> SEQ ID NO 33
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 33

```
atgaccgatc gtctgaaggg caaagtagcc atcgtaaccg gcgggacact gggtatcggt      60
ttggcaatcg ccgataaatt tgtaacagag ggtgcgaaag tagttattac tggtcgtcgc     120
gcggatgttg gtgaaaaggc cgccaaatca atcggcggca ctgatgttat tcgctttgtc     180
cagcacgatg tttccgatga agcaggctgg ccaaaactgt tcgacaccac cgaggagaca     240
ttcggcccgg ttacgaccct ggtgaacaat gcagggattg gctatcgcaa aagcgttgaa     300
gacactacca cggaggaatg gcgtaaactg ctgtccgtta atctggatgg tgttttttc     360
ggcacccgtc tgggcattca gcgcatgaaa tgtaaaggct gggcgctag catcatcaat     420
atgagcagta ttctggggca ggtaggcgat ccggcgactg gggcatacaa cgcttccaag     480
ggggcggtac gtatcatgtc gaaaagcgca gcgctgctgt gcgcactgaa ggactacgat     540
gtgcgtgtca acacagtaca tccgggccc atcaagaccc cgttaatgga tgatatgccg     600
ggtgctgagg aaatgatgtc acagcgtacg aaaacccta tgggtcacat ggcgaaccg      660
aatgacatcg catgggtctg tgtgtacctg gcatctgacg aatcgaaatt tgcgacgggt     720
gcagaatttg tggtcgacgg cgggtatacc gcacagtga                             759
```

<210> SEQ ID NO 34
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 34

Met Thr Asp Arg Leu Lys Gly Lys Val Ala Ile Val Thr Gly Gly Thr
1               5                   10                  15

Leu Gly Ile Gly Leu Ala Ile Ala Asp Lys Phe Val Thr Glu Gly Ala
                20                  25                  30

Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Pro Lys Leu Phe Asp Thr Thr Glu Glu Thr
65                  70                  75                  80

Phe Gly Pro Val Thr Thr Leu Val Asn Asn Ala Gly Ile Gly Tyr Arg
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Cys Lys Gly Leu Gly Ala Ser Ile Ile Asn Met Ser Ser Ile
        130                 135                 140

Leu Gly Gln Val Gly Asp Pro Ala Thr Gly Ala Tyr Asn Ala Ser Lys
145                 150                 155                 160

```
Gly Ala Val Arg Ile Met Ser Lys Ser Ala Leu Leu Cys Ala Leu
            165                 170                 175

Lys Asp Tyr Asp Val Arg Val Asn Thr Val His Pro Gly Pro Ile Lys
        180                 185                 190

Thr Pro Leu Met Asp Asp Met Pro Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250

<210> SEQ ID NO 35
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 35
atgaccgatc gtctgaaggg caaagtagcc atcgtaaccg gcgggacaca cggtatcggt      60
ttggcaatcg ccactaaatt tgtaacagag ggtgcgaaag tagttattac tggtcgtcgc     120
gcggatgttg gtgaaaaggc cgccaaatca atcggcggca ctgatgttat tcgctttgtc     180
cagcacgatg tttccgatga agcaggctgg ggcaaactgt tcgacaccac cgaggagaca     240
ttcggcccgg ttacgaccct ggtgaacaat gcagggattg gctatcgcaa aagcgttgaa     300
gacactacca cggaggaatg gcgtaaactg ctgtccgtta atctggatgg tgttttttc      360 ggcacccgtc tgggcattca gcgcatgaaa tgtaaaggct gggcgctag catcatcaat     420 atgagcagta ttctggggca ggtaggcgat ccggcgactg ggcatactc cgcttccaag     480 ggggcggtac gtatcatgtc gaaaagcgca gcgctgctgt gcgcactgaa ggactacgat     540
gtgcgtgtca acacagtaca tccgggcccc atcaagaccc cgttaatgga tgatatgccg     600
ggtgctgagg aaatgatgtc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtatacc gcacagtga                           759

<210> SEQ ID NO 36
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 36

Met Thr Asp Arg Leu Lys Gly Lys Val Ala Ile Val Thr Gly Gly Thr
1               5                   10                  15

His Gly Ile Gly Leu Ala Ile Ala Thr Lys Phe Val Thr Glu Gly Ala
            20                  25                  30
```

```
Lys Val Val Ile Thr Gly Arg Arg Ala Asp Val Gly Glu Lys Ala Ala
            35                  40                  45

Lys Ser Ile Gly Gly Thr Asp Val Ile Arg Phe Val Gln His Asp Val
        50                  55                  60

Ser Asp Glu Ala Gly Trp Gly Lys Leu Phe Asp Thr Thr Glu Glu Thr
65                  70                  75                  80

Phe Gly Pro Val Thr Thr Leu Val Asn Asn Ala Gly Ile Gly Tyr Arg
                85                  90                  95

Lys Ser Val Glu Asp Thr Thr Thr Glu Glu Trp Arg Lys Leu Leu Ser
            100                 105                 110

Val Asn Leu Asp Gly Val Phe Phe Gly Thr Arg Leu Gly Ile Gln Arg
        115                 120                 125

Met Lys Cys Lys Gly Leu Gly Ala Ser Ile Ile Asn Met Ser Ser Ile
    130                 135                 140

Leu Gly Gln Val Gly Asp Pro Ala Thr Gly Ala Tyr Ser Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Met Pro Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```

<210> SEQ ID NO 37
<211> LENGTH: 759
<212> TYPE: DNA
<213> ORGANISM: Artificial Sequence
<220> FEATURE:
<223> OTHER INFORMATION: Engineered variant of L. kefir ketoreductase

<400> SEQUENCE: 37

```
atgaccgatc gtctgaaggg caaagtagcc atcgtaaccg gcgggacaca cggtatcggt      60
ttggcaatcg ccgataaatt tgtaacagag ggtgcgaaag tagttattac tggtcgtcgc     120
gcggatgttg gtgaaaaggc cgccaaatca atcggcggca ctgatgttat tcgctttgtc     180
cagcacgatg tttccgatga agcaggctgg ccaaaactgt tcgacaccac cgaggagaca     240
ttcggcccgg ttacgaccct ggtgaacaat gcagggattg gctatcgcaa aagcgttgaa     300
gacactacca cggaggaatg gcgtaaactg ctgtccgtta atctggatgg tgttttttc      360
ggcacccgtc tgggcattca gcgcatgaaa tgtaaaggct gggcgctag catcatcaat     420
atgagcagta ttctggggca ggtaggcgat ccggcgactg ggcatactc cgcttccaag     480
ggggcggtac gtatcatgtc gaaaagcgca gcgctgctgt gcgcactgaa ggactacgat     540
gtgcgtgtca acacagtaca tccgggcccc atcaagaccc cgttaatgga tgatatgccg     600
ggtgctgagg aaatgatgtc acagcgtacg aaaaccccta tgggtcacat tggcgaaccg     660
aatgacatcg catgggtctg tgtgtacctg gcatctgacg aatcgaaatt tgcgacgggt     720
gcagaatttg tggtcgacgg cgggtatacc gcacagtga                            759
```

<210> SEQ ID NO 38
<211> LENGTH: 252
<212> TYPE: PRT
<213> ORGANISM: Artificial Sequence
<220> FEATURE:
<223> OTHER INFORMATION: Engineered variant of L. kefir ketoreductase

<400> SEQUENCE: 38

```
Met Thr Asp Arg Leu Lys Gly Lys Val Ala Ile Val Thr Gly Gly Thr
1               5                   10                  15

His Gly Ile Gly Leu Ala Ile Ala Asp Lys Phe Val Thr Glu Gly Ala
            20                  25                  30

Lys Val Ile Thr Gly Arg Arg Ala Asp Val Gly Glu Lys Ala Ala
        35                  40                  45

Lys Ser Ile Gly Gly Thr Asp Val Ile Arg Phe Val Gln His Asp Val
    50                  55                  60

Ser Asp Glu Ala Gly Trp Pro Lys Leu Phe Asp Thr Thr Glu Glu Thr
65                  70                  75                  80

Phe Gly Pro Val Thr Thr Leu Val Asn Asn Ala Gly Ile Gly Tyr Arg
                85                  90                  95

Lys Ser Val Glu Asp Thr Thr Thr Glu Glu Trp Arg Lys Leu Leu Ser
                100                 105                 110

Val Asn Leu Asp Gly Val Phe Phe Gly Thr Arg Leu Gly Ile Gln Arg
            115                 120                 125

Met Lys Cys Lys Gly Leu Gly Ala Ser Ile Ile Asn Met Ser Ser Ile
    130                 135                 140

Leu Gly Gln Val Gly Asp Pro Ala Thr Gly Ala Tyr Ser Ala Ser Lys
145                 150                 155                 160

Gly Ala Val Arg Ile Met Ser Lys Ser Ala Ala Leu Leu Cys Ala Leu
                165                 170                 175

Lys Asp Tyr Asp Val Arg Val Asn Thr Val His Pro Gly Pro Ile Lys
            180                 185                 190

Thr Pro Leu Met Asp Asp Met Pro Gly Ala Glu Glu Met Met Ser Gln
        195                 200                 205

Arg Thr Lys Thr Pro Met Gly His Ile Gly Glu Pro Asn Asp Ile Ala
    210                 215                 220

Trp Val Cys Val Tyr Leu Ala Ser Asp Glu Ser Lys Phe Ala Thr Gly
225                 230                 235                 240

Ala Glu Phe Val Val Asp Gly Gly Tyr Thr Ala Gln
                245                 250
```